US010421813B2

(12) United States Patent
Arnett et al.

(10) Patent No.: US 10,421,813 B2
(45) Date of Patent: *Sep. 24, 2019

(54) ONCOSTATIN M RECEPTOR ANTIGEN BINDING PROTEINS

(71) Applicant: Kiniksa Pharmaceuticals, Ltd., Wellesley, MA (US)

(72) Inventors: Heather A. Arnett, Seattle, WA (US); Sabine S. Escobar, Sammamish, WA (US); Chadwick T. King, North Vancouver (CA); Ai Ching Lim, Mercer Island, WA (US); Saravanakumar Narayanan, Brookline, MA (US); Paul H. Weinreb, Weston, MA (US); Nels E. Pederson, Mansfield, MA (US)

(73) Assignee: Kiniksa Pharmaceuticals, Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,699

(22) Filed: Jul. 11, 2017

(65) Prior Publication Data
US 2018/0002429 A1    Jan. 4, 2018

Related U.S. Application Data

(62) Division of application No. 15/486,094, filed on Apr. 12, 2017, now Pat. No. 9,738,721, which is a division of application No. 14/891,491, filed as application No. PCT/US2014/040360 on May 30, 2014, now Pat. No. 9,663,571.

(60) Provisional application No. 61/829,082, filed on May 30, 2013.

(51) Int. Cl.
C07K 16/28 (2006.01)
C07K 16/24 (2006.01)
A61K 39/395 (2006.01)

(52) U.S. Cl.
CPC ........ C07K 16/2866 (2013.01); A61K 39/395 (2013.01); C07K 16/244 (2013.01); C07K 16/248 (2013.01); C07K 16/28 (2013.01); C07K 2317/21 (2013.01); C07K 2317/515 (2013.01); C07K 2317/56 (2013.01); C07K 2317/565 (2013.01); C07K 2317/76 (2013.01); C07K 2317/92 (2013.01)

(58) Field of Classification Search
CPC .............. C07K 16/2866; C07K 16/244; C07K 16/248; C07K 2317/56; A61K 39/395
See application file for complete search history.

(56) References Cited

U.S. PATENT DOCUMENTS

| 5,783,672 | A | 7/1998 | Mosley et al. |
|---|---|---|---|
| 5,907,033 | A | 5/1999 | Radka et al. |
| 5,925,740 | A | 7/1999 | Mosley et al. |
| 7,943,132 | B2 | 5/2011 | Yao et al. |
| 9,475,876 | B2 * | 10/2016 | Morikawa .......... C07K 16/2866 |
| 9,593,163 | B2 | 1/2017 | Arnett et al. |
| 2003/0054497 | A1 | 3/2003 | Co et al. |
| 2003/0096339 | A1 | 5/2003 | Sprecher et al. |
| 2003/0215838 | A1 | 11/2003 | Sprecher et al. |
| 2003/0224487 | A1 | 12/2003 | Sprecher et al. |
| 2004/0081650 | A1 | 4/2004 | Life et al. |
| 2006/0171951 | A1 | 8/2006 | Mather et al. |
| 2006/0182743 | A1 | 8/2006 | Bilsborough |
| 2006/0275296 | A1 | 12/2006 | Siadak et al. |
| 2007/0160611 | A1 | 7/2007 | Yao et al. |
| 2007/0286861 | A1 | 12/2007 | Ellis et al. |
| 2009/0208494 | A1 | 8/2009 | Bondensgaard et al. |
| 2009/0252732 | A1 | 10/2009 | Siadak et al. |
| 2010/0008909 | A1 | 1/2010 | Siadak et al. |
| 2010/0055092 | A1 | 3/2010 | Hasegawa et al. |
| 2010/0172900 | A1 | 7/2010 | Korman et al. |
| 2015/0093391 | A1 | 4/2015 | Jorcyk et al. |
| 2015/0132303 | A1 | 5/2015 | Morikawa et al. |

FOREIGN PATENT DOCUMENTS

| CN | 1056713 A | 3/1990 |
|---|---|---|
| WO | WO-2005/095457 A2 | 10/2005 |
| WO | WO2013/168829 A1 | 11/2013 |

OTHER PUBLICATIONS

Rudikoff et al., Single amino acid substitution altering antigen-binding specificity. Proc. Natl. Acad. Sci. USA 79:1979-1983, 1982.*
Brown et al., Tolerance of single, but not multiple, amino acid replacements in antibody VH CDR 2: a means of minimizing B cell wastage from somatic hypermutation? J Immunol. May 1, 1996;156(9):3285-3291.*
Vajdos et al., Comprehensive functional maps of the antigen-binding site of an anti-ErbB2 antibody obtained with shotgun scanning mutagenesis. J. Mol. Biol. 320:415-428, 2002.*
Paul, Fundamental Immunology, 3rd Edition, 1993, pp. 292-295.*
U.S. Appl. No. 14/891,491, filed May 19, 2016, Arnett et al.
U.S. Appl. No. 15/486,094, filed Apr. 12, 2017, Arnett et al.
Anonymous, SA1290581 align light chain, Sep. 2014, retrieved from the Internet at URL:q/ibis, retrieved on Sep. 29, 2014, 1 page.

(Continued)

Primary Examiner — Ruixiang Li
(74) Attorney, Agent, or Firm — Proskauer Rose LLP; Fangli Chen; Julio J. Mendez

(57) ABSTRACT

The invention provides anti-oncostatin M receptor-β (OSMR) antigen binding proteins, e.g., antibodies and functional fragments, derivatives, muteins, and variants thereof. OSMR antigen binding proteins interfere with binding of OSM and/or IL-31 to OSMR. In some embodiments, anti-OSMR antigen binding proteins are useful tools in studying diseases and disorders associated with OSMR and are particularly useful in methods of treating diseases and disorders associated with OSMR and binding of OSM and/or IL-31 to OSMR.

12 Claims, No Drawings

Specification includes a Sequence Listing.

(56) References Cited

OTHER PUBLICATIONS

Anonymous, SA1290581 Heavy chain align, Sep. 2014, retrieved from the Internet at URL:q/ibis, retrieved on Sep. 29, 2014, 1 page.
Anonymous, SA1290581 Identity of SEQ ID No. 29, Sep. 2014, retrieved from the Internet at URL:q/ibis, retrieved on Sep. 29, 2014, 2 pages.
Arita, et al., Oncostatin M Receptor-β Mutations Underlie Familial Primary Localized Cutaneous Amyloidosis, The American Journal of Human Genetics 82, 73-80, Jan. 2008.
Bilsborough, et al., IL-31 Receptor (IL-31RA) Knockout Mice Exhibit Elevated Responsiveness to Oncostatin M, J Immunol 2010; 185:6023-6030.
Boniface, K., et al., Oncostatin M Secreted by Skin Infiltrating T Lymphocytes Is a Potent Keratinocyte Activator Involved in Skin Inflammation, J Immunol 2007; 178:4615-4622.
Canady, et al, Increased KGF Expression Promotes Fibroblast Activation in a Double Paracrine Manner Resulting in Cutaneous Fibrosis, Journal of Investigative Dermatology (2013), vol. 133, pp. 647-657.
Careta, et al., Localized scleroderma: clinical spectrum and therapeutic update, An Bras Dermatol. 2015;90(1):62-73.
Cawston et al., The role of oncostatin M in animal and human connective tissue collagen turnover and its localization within the rheumatoid joint, Arthritis Rheum., Oct. 1998, 41(10):1760-71.
Chattopadhyay, et al., Interleukin-31 and Oncostatin-M Mediate Distinct Signaling Reactions and Response Patterns in Lung Epithelial Cells, The Journal of Biological Chemistry vol. 282, No. 5, pp. 3014-3026, Feb. 2, 2007.
Cheung, et al., Activation of human eosinophils and epidermal keratinocytes by $T_h2$ cytokine IL-31: implication for the immunopathogenesis of atopic dermatitis, International Immunology, vol. 22, No. 6, 2010, pp. 453-467.
Choy, et al., Safety, tolerability, pharmacokinetics and pharmacodynamics of an anti-oncostatin M monoclonal antibody in rheumatoid arthritis: results from phase II randomized, placebo-controlled trials, Arthritis Research & Therapy 2013, 15:R132, pp. 1-10.
Clements, et al, Scleroderma lung study (SLS): differences in the presentation and course of patients with limited versus diffuse systemic sclerosis, Ann Rheum Dis 2007;66:1641-1647.
Cornelissen, et al., Signaling by IL-31 and functional consequences, European Journal of Cell Biology 91 (2012) 552-566.
Dambacher et al., Interleukin 31 mediates MAP kinase and STATI/3 activation in intestinal epithelial cells and its expression is upregulated in inflammatory bowel disease, Gut, 2007, 56(9): 1257-65.
Davidson, et al., The multiple pathways for itch and their interactions with pain, Trends in Neurosciences, Dec. 2010, vol. 33, No. 12, pp. 550-558.
De Hooge et al., Adenoviral transfer of murine oncostatin M elicits periosteal bone apposition in knee joints of mice, despite synovial inflammation and up-regulated expression of interleukin-6 and receptor activator of nuclear factor-kappa B ligand, Am J. Pathol., 2002, 160(5): 1733-43.
Denton, C. P., Therapeutic targets in systemic sclerosis, Arthritis Research & Therapy 2007, 9(Suppl 2):S6, pp. 1-5.
Dey, et al., Signaling network of Oncostatin M pathway, J. Cell Commun. Signal. (2013) 7:103-108.
Dillon et al., Interleukin 31, a cytokine produced by activated T cells, induces dermatitis in mice, Nat. Immunol. 2004, 5(7):752-60.
Diveu et al., Predominant express of the long isoform of GP-130-like (GPL) receptor is required for interleukin-31 signaling, European Cytokine Network, 2004, 15(4):291-302.
Diveu, C., GPL, a Novel Cytokine Receptor Related to GP130 and Leukemia Inhibitory Factor Receptor, The Journal of Biological Chemistry, vol. 278, No. 50, Issue of Dec. 12, pp. 49850-49859, 2003.
Dousset, et al., A Th2 Cytokine Interleukin-31 Signature in a Case of Sporadic Lichen Amyloidosis, Acta Derm Venereol 2015; 95: 223-224.

Drechsler, et al., Characterization of the Rat Oncostatin M Receptor Complex Which Resembles the Human, but Differs from the Murine Cytokine Receptor, PLOS ONE, Aug. 2012, vol. 7, Issue 8.
Dreuw et al., Characterization of the signaling capacities of the novel gp130-like cytokine receptor, J. Biol. Chem., 2004, 279(34):36112-20.
Edukulla, et al., Th2 Cytokines Augment IL31/IL31RA Interactions via STAT6-dependent IL-31RA Expression, J Biol Chem. May 22, 2015; 290(21): 13510-13520.
Frech, et al., Treatment of early diffuse systemic sclerosis skin disease, Clin Exp Rheumatol. 2013; 31(2 0 76): 166-171.
Gatsios et al., Oncostatin M differentially regulates tissue inhibitors of metalloproteinases TIMP-1 and TIMP-3 gene expression in human synovial lining cells, Eur. J. Biochem., Oct. 1996, 241(1):56-63.
Hams, et al., Oncostatin M Receptor-β Signaling imits Monocytic Cell Recruitment in Acute Inflammation, The J Immunol 2008; 181:2174-2180.
Han, et al., A subpopulation of nociceptors specifically linked to itch, Nat Neurosci. Feb. 2013; 16(2): 174-182.
Hasegawa et al., Enhanced production of interleukin-6 (IL-6), oncostatin M and soluble IL-6 Rheumatology (Oxford), 1999, 38(7):612-7.
Hasegawa et al., Serum levels of interleukin 6 (IL-6), oncostatin M, soluble IL-6 receptor, and soluble gp130 in patients with systemic sclerosis, J. Rheumatol, Feb. 1998, 25(2):308-13.
Hermanns, et al., Contribution of Leukemia Inhibitory Factor Receptor and Oncostatin M Receptor to Signal Transduction in Heterodimeric Complexes with Glycoprotein 130, J Immunol 1999; 163:6651-6658.
Hui et al., Oncostatin M in combination with tumor necrosis factor α induces cartilage damage and matrix metalloproteinase expression in vitro and in vivo, Arthritis Rheum., Dec. 2003, 48(12):3404-18.
Hummers, Laura K., The Current State of Biomarkers in Systemic Sclerosis, Curr Rheumatol Rep. Feb. 2010; 12(1): 34-39.
Ikoma, et al., The neurobiology of itch, Neuroscience, vol. 7, Jul. 2006, pp. 535-547.
International Preliminary Report on Patentability in International Application No. PCT/US2014/040360, dated Dec. 1, 2015, 14 pages.
International Search Report and Written Opinion in International Application No. PCT/US2014/040360, dated Jan. 21, 2015, 22 pages.
Invitation to Pay Additional Fees in International Application No. PCT/US2014/040360, dated Oct. 13, 2014, 8 pages.
Ip, et al., Interleukin-31 induces cytokine and chemokine production from human bronchial epithelial cells through activation of mitogenactivated protein kinase signalling pathways: implications for the allergic response, 2007, Immunology, 122, 532-541.
Jawa et al., Regulated Expression of the IL-31 Receptor in Bronchial and Alveolar Epithelial Cells, Pulmonary Fibroblasts, and Pulmonary Macrophages, J. Interferon Cytokine Res., Apr. 2008, 28(4):207-19.
Jazayeri et al., Targeting the glycoprotein 130 receptor subunit to control pain and inflammation, Journal of Interferon and Cytokine Research, 2010, 30(12):865-873.
Kasraie, et al., Interleukin (IL)-31 activates signal transducer and activator of transcription (STAT)-1, STAT-5 and extracellular signal-regulated kinase 1/2 and down-regulates IL-12p40 production in activated human macrophages, Allergy 68 (2013) 739-747.
Khanna, D., et al., Evidence-based Management of Rapidly Progressing Systemic Sclerosis, Best Pract Res Clin Rheumatol. Jun. 2010; 24(3): 387-400.
Kim, et al., IL-31 Serum Protein and Tissue mRNA Levels in Patients with Atopic Dermatitis, Ann Dermatol vol. 23, No. 4, 2011, pp. 468-473.
Ko, et al., Interleukin-31 is associated with uremic pruritus in patients receiving hemodialysis, J Am Acad Dermatol Dec. 2014, pp. 1151-1159.
Kong et al., In vivo activities of cytokine oncostatin M in the regulation of plasma lipid levels, J. Lipid Res., 2005, 46(6): 1163-71.

(56) References Cited

OTHER PUBLICATIONS

Kurzinski, et al., Cytokine profiles in localized scleroderma and relationship to clinical features, Cytokine. Aug. 2011; 55(2): 157-164.
Kuypers, D. RJ, Skin problems in chronic kidney disease, Nature Clinical Practice, Mar. 2009 vol. 5 No. 3, pp. 157-170.
Lauria, et al., European Federation of Neurological Societies/Peripheral Nerve Society Guideline on the use of skin biopsy in the diagnosis of small fiber neuropathy. Report of a joint task force of the European Federation of Neurological Societies and the Peripheral Nerve Society, European Journal of Neurology 2010, 17: 903-912.
Leask et al., TGF-signaling and the fibrotic response, FASEB J, 2004, 18(7):816-27.
Lee, et al., Mechanistic correlations between two itch biomarkers, IL-31 cytokine and beta-endorphin europeptide, via STAT3/calcium axis in atopic dermatitis, Br J Dermatol. Oct. 2012; 167(4): 794-803.
Levy et al., Oncostatin M: a cytokine upregulated in human cirrhosis, increases collagen production by human hepatic stellate cells, J. Hematol., 2000, 32(2):218-26.
Luzina, I. G., et al., Occurrence of an Activated, Profibrotic Pattern of Gene Expression in Lung CD8+ T Cells From Scleroderma Patients; Arthritis & Rheumatism, vol. 48, No. 8, Aug. 2003, pp. 2262-2274.
Manicourt et al., Synovial fluid levels of tumor necrosis factor alpha and oncostatin M correlate with levels of markers of the degradation of crosslinked collagen and cartilage aggrecan in rheumatoid arthritis but not in osteoarthritis, Arthritis. Rheum., Feb. 2000, 43(2):281-8.
Matucci-Cerinic, M., et al., Clinical trials in systemic sclerosis: lessons learned and outcomes, Arthritis Research & Therapy 2007,9(Suppl 2):S7, pp. 1-9.
Misery et al., Neuropathic pruritus, Nat. Rev. Neurol. 10, 408-416 (2014).
Morikawa et al., Essential function of oncostatin m in nociceptive neurons of dorsal root ganglia, J. Neurosci. Feb. 2004, 24(8):1941-7.
Mozaffarian, et al., Mechanisms of Oncostatin M-Induced Pulmonary Inflammation and Fibrosis, The Journal of Immunology, 2008, 181: 7243-7253.
Musolino, et al., Possible Role of Interleukin-31/33 Axis in Imatinib Mesylate-Associated Skin Toxicity, Turk J Hematol 2015; 32:168-171.
Nobbe, et al., IL-31 Expression by Inflammatory Cells is Preferentially Elevated in Atopic Dermatitis, Acta Derm Venereol 2012; 92: 24-28.
Panka et al., Variable region framework differences result in decreased or increased affinity of variant anti-digoxin antibodies, Proceedings of the National Academy of Sciences, May 1988, 85(9):3080-3084.
Phan, et al., Assessment of Pruritus Intensity: Prospective Study on Validity and Reliability of the Visual Analogue Scale, Numerical Rating Scale and Verbal Rating Scale in 471 Patients with Chronic Pruritus, Acta Derm Venereol 2012; 92: 502-507.
Quillinan, et al., Treatment of diffuse systemic sclerosis with hyperimmune caprine serum (AIMSPRO): a phase II double-blind placebo-controlled trial, Ann Rheum Dis 2014; 73:56-61.
Rabenhorst, et al., Interleukin-31: A Novel Diagnostic Marker of Allergic Diseases, Curr Allergy Asthma Rep (2014) 14:423.
Repovic et al., Oncostatin-M induction of vascular endothelial growth factor expression in astroglioma cells, Oncogene, Nature Publishing Group, 2003, 22(50):8117-8124.
Richards et al., Modulation of extracellular matrix using adenovirus vectors, Biochem. Soc. Trans., 2002, 30(part 2):107-I I.
Richards, Carl D., The Enigmatic Cytokine Oncostatin M and Roles in Disease, ISRN Inflammation vol. 2013, Article ID 512103, 23 pages.
Rowan et al., Adenoviral Gene Transfer of Interleukin-I in Combination with Oncostatin M Induces Significant Joint Damage in a Murine Model, Am. J. Pathol., Jun. 2003, 162(6):1975-84.
Rudikoff et al., Single amino acid substitution altering antigen-binding specificity, Proceedings of the National Academy of Sciences, Mar. 1982, vol. 79: 1979-1983.
Shah, et al., My Approach to the Treatment of Scleroderma, Mayo Clin Proc. Apr. 2013; 88(4): 377-393.
Solomon, et al., Scleroderma lung disease, Eur Respir Rev. Mar. 1, 2013; 22(127): 6-19.
Sonkoly, E., et al., IL-31: A new link between T cells and pruritus in atopic skin inflammation, J Allergy Clin Immunol, Feb. 2006, pp. 411-417.
Stander, et al, Emerging drugs for the treatment of pruritus, Expert Opin. Emerging Drugs (2015) 20(3):515-521.
Stander, et al., Pruritus Assessment in Clinical Trials: Consensus Recommendations from the International Forum for the Study of Itch (IFSI) Special Interest Group Scoring Itch in Clinical Trials, Acta Derm Venereol 2013; 93: 509-514.
Tamura et al., Expression of oncostatin M receptor in a specific subset of nociceptive sensory neurons, European Journal of Neuroscience 17:2287-2298 (2003).
Tanaka, et al., The molecular skin pathology of familial primary localized cutaneous amyloidosis, Experimental Dermatology, 2010, 19, 416-423.
Usoskin, et al., Unbiased classification of sensory neuron types by large-scale single-cell RNA sequencing, Nature Neuroscience, vol. 18, No. 1, Jan. 2015, pp. 145-155.
Vavrova, K., Emerging small-molecule compounds for treatment of atopic dermatitis: a review, Expert Opin. Ther. Patents (2016) 26(1):21-34.
Yosipovitch, et al., Chronic Pruritus, N. Engl J Med, Apr. 25, 2013; 368:1625-34.
Yosipovitch, et al., What Causes Itch in Atopic Dermatitis? Current Allergy and Asthma Reports 2008, 8: 306-311.
Zhang, et al., Structures and biological functions of IL-31 and IL-31 receptors, Cytokine Growth Factor Rev. 2008; 19(5-6): 347-356.
Gregoritza et al., "Design of hydrogels for delayed antibody release utilizing hydrophobic association and Diels—Alder chemistry in tandem", J. Mater. Chem. B, 4: 3398-3408 (2016).
Lee et al., "Injectable Biodegradable Hydrogels from Vitamin D-Functionalized Polycarbonates for the Delivery of Avastin with Enhanced Therapeutic Efficiency against Metastatic Colorectal Cancer", Biomacromolecules, 16: 465-475 (2015).
Qian et al., "Expression and significance of OSM and OSMR in HCC and paracancerous tissues" Journal of Hepatobiliary Surgery, 17(2): 147-148 (2009).
Yi et al., "Pharmacokinetic properties and antitumor efficacy of the 5-fluorouracil loaded PEG-hydrogel", BMC Cancer, 10:211 (2010).
Zhang et al., "Research progress of IL-31 and its receptors", Progress in Modern Biomedicine, 8(5) 958-960, 964 (2008).
Jalal A. Jazayeri et al., " Targeting the Glycoprotein 130 Receptor Subunit to Control Pain and Inflammation", Journal of Interferon & Cytokine Research, (Dec. 1, 2010) vol. 30, No. 12, ISSN 1079-9907, pp. 865-873.
Repovic Pavle et al., "Oncostatin-M induction of vascular endothelial growth factor expression in astroglioma cells", Oncogene, Nature Publishing Group, GB, (Nov. 6, 2003), vol. 22, No. 50, ISSN 0950-9232, pp. 8117-8124.
"Vanda's PhII 'itch' trial fails on 'high placebo effect'". Scrip. Mar. 9, 2015.
"Melano Therapeutics Announces Results from a Phase 2 Trial of Serlopitant for Pruritus Associated with Atopic Dermatitis" GlobalNewswire. Apr. 8, 2018.
"Anti-interleukin-31-antibodies ameliorate scratching behaviour in NC/Nga mice: a model of atopic dermatitis" Experimental Dermatology 2009, 18, 35-43.

\* cited by examiner

SEQUENCE LISTING

```
<160> NUMBER OF SEQ ID NOS: 54

<210> SEQ ID NO 1
<211> LENGTH: 979
<212> TYPE: PRT
<213> ORGANISM: Homo sapiens
<220> FEATURE:
<221> NAME/KEY: MISC_FEATURE
<223> OTHER INFORMATION: Human OSMR

<400> SEQUENCE: 1

Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
                20                  25                  30

Thr Pro Val Ser Leu Lys Val Ser Thr Asn Ser Thr Arg Gln Ser Leu
            35                  40                  45

His Leu Gln Trp Thr Val His Asn Leu Pro Tyr His Gln Glu Leu Lys
        50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
                100                 105                 110

Arg Ile Lys Ser Leu Val Asp Asp Ala Lys Phe Pro Glu Pro Asn Phe
            115                 120                 125

Trp Ser Asn Trp Ser Ser Trp Glu Glu Val Ser Val Gln Asp Ser Thr
        130                 135                 140
```

```
Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
        355                 360                 365

Glu Leu His Gly Glu Gly Lys Met Met Gln Tyr Asn Val Ser Ile Lys
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
            420                 425                 430

Ala Pro Asp Val Trp Arg Ile Val Ser Leu Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Glu Asn Leu Asp Lys Pro Ser Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ile Ser Ala Asp Pro Glu Asn
        515                 520                 525

Lys Glu Val Glu Glu Glu Arg Ile Ala Gly Thr Glu Gly Gly Phe Ser
    530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
```

```
                565                 570                 575
Val Gly Pro Asn Thr Thr Ser Thr Val Ile Ser Thr Asp Ala Phe Arg
            580                 585                 590

Pro Gly Val Arg Tyr Asp Phe Arg Ile Tyr Gly Leu Ser Thr Lys Arg
            595                 600                 605

Ile Ala Cys Leu Leu Glu Lys Lys Thr Gly Tyr Ser Gln Glu Leu Ala
            610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
                660                 665                 670

Pro Arg Phe Glu Lys Ala Val Leu Ser Asp Gly Ser Glu Cys Cys Lys
                675                 680                 685

Tyr Lys Ile Asp Asn Pro Glu Glu Lys Ala Leu Ile Val Asp Asn Leu
            690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser Met Leu Ile His Ile Leu Leu Pro Met Val Phe Cys Val
                740                 745                 750

Leu Leu Ile Met Val Met Cys Tyr Leu Lys Ser Gln Trp Ile Lys Glu
                755                 760                 765

Thr Cys Tyr Pro Asp Ile Pro Asp Pro Tyr Lys Ser Ser Ile Leu Ser
            770                 775                 780

Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
                805                 810                 815

Lys Ile Gln Phe Leu Gly Thr Arg Lys Ser Leu Thr Glu Thr Glu Leu
                820                 825                 830

Thr Lys Pro Asn Tyr Leu Tyr Leu Leu Pro Thr Glu Lys Asn His Ser
            835                 840                 845

Gly Pro Gly Pro Cys Ile Cys Phe Glu Asn Leu Thr Tyr Asn Gln Ala
            850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
                885                 890                 895

Leu Glu Lys Asn Tyr Met Asn Ser Leu Gly Glu Ile Pro Ala Gly Glu
                900                 905                 910

Thr Ser Leu Asn Tyr Val Ser Gln Leu Ala Ser Pro Met Phe Gly Asp
            915                 920                 925

Lys Asp Ser Leu Pro Thr Asn Pro Val Glu Ala Pro His Cys Ser Glu
930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975

His Tyr Cys
```

```
<210> SEQ ID NO 2
<211> LENGTH: 977
<212> TYPE: PRT
<213> ORGANISM: Macaca fascicularis
<220> FEATURE:
<221> NAME/KEY: MISC_FEATURE
<223> OTHER INFORMATION: Cynomolgus monkey OSMR

<400> SEQUENCE: 2

Met Ala Leu Phe Val Val Phe Gln Thr Thr Phe Phe Leu Ile Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Ile His Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Val
65                  70                  75                  80

Trp Val Gly Asn Tyr Ser Thr Pro Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Val Ile Asp Asp Ala Ser Phe Pro Glu Pro Asn Phe
        115                 120                 125

Trp Ser Asn Trp Ser Ser Trp Glu Glu Val Ser Val Gln Asp Tyr Leu
    130                 135                 140

Gly Arg Gly Thr Leu Phe Val Phe Pro Lys Asp Lys Leu Val Glu Glu
145                 150                 155                 160

Gly Ser Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Arg Gly Thr Asn Ile Tyr Cys Glu Ala Ser Gln Gly Asn Val Ser Lys
    210                 215                 220

Gly Ile Glu Gly Ile Val Leu Phe Val Ser Lys Val Leu Glu Glu Pro
225                 230                 235                 240

Lys Asp Phe Ser Cys Glu Ser Gln Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Met Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Met Arg Asn Asn Phe Thr Tyr Leu Cys Gln Ile
        355                 360                 365
```

```
Glu Leu His Gly Glu Gly Lys Met Met Gln Tyr Asp Val Ser Ile Asn
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Thr
                405                 410                 415

Glu Trp Ser Gly Gln Asn Phe Thr Thr Leu Glu Ala Ala Pro Ser Glu
            420                 425                 430

Ala Pro Asp Val Trp Arg Ser Val Asn Ser Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Glu Asn Leu Asp Lys Pro Ser Arg
465                 470                 475                 480

Ser Glu Leu Arg Ser Ile Pro Ala Pro Ala Asn Ser Thr Lys Leu Ile
                485                 490                 495

Leu Asp Arg Cys Ser Tyr Gln Ile Cys Val Thr Ala Asn Asn Ser Val
            500                 505                 510

Gly Ala Ser Pro Ala Ser Ile Ile Val Ile Ser Ala Asp Pro Glu Asn
        515                 520                 525

Lys Glu Val Glu Glu Glu Arg Ile Ala Gly Thr Glu Gly Gly Phe Ser
    530                 535                 540

Leu Ser Trp Lys Pro Gln Pro Gly Asp Val Ile Gly Tyr Val Val Asp
545                 550                 555                 560

Trp Cys Asp His Pro Gln Asp Val Leu Gln Trp Lys Asn Val Gly Pro
                565                 570                 575

Asn Thr Thr Ser Thr Val Ile Ser Thr Asp Ala Phe Arg Pro Gly Val
            580                 585                 590

Arg Tyr Asp Phe Arg Ile Tyr Gly Leu Ser Thr Lys Arg Ile Ala Cys
        595                 600                 605

Leu Leu Glu Lys Lys Thr Gly Tyr Ser Gln Glu Leu Ala Pro Ser Asp
    610                 615                 620

Asn Pro His Val Leu Val Asp Met Leu Thr Ser His Ser Phe Thr Leu
625                 630                 635                 640

Ser Trp Lys Asp Tyr Ser Thr Glu Ser Gln Pro Gly Phe Ile Gln Gly
                645                 650                 655

Tyr His Val Tyr Leu Lys Ser Lys Ala Arg Gln Cys His Pro Arg Phe
            660                 665                 670

Gln Lys Ala Val Leu Ser Asp Gly Ser Glu Cys Cys Arg Tyr Lys Ile
        675                 680                 685

Asp Asn Pro Glu Glu Lys Ala Leu Ile Val Asp Asn Leu Lys Pro Glu
    690                 695                 700

Ser Phe Tyr Glu Phe Phe Val Thr Pro Phe Thr Ser Ala Gly Glu Gly
705                 710                 715                 720

Pro Asn Ala Thr Phe Thr Lys Val Thr Thr Pro Asp Glu His Ser Ser
                725                 730                 735

Met Leu Ile Arg Ile Leu Leu Pro Met Val Phe Cys Val Leu Leu Ile
            740                 745                 750

Met Ile Val Cys Tyr Leu Lys Ser Gln Trp Ile Lys Glu Thr Cys Tyr
        755                 760                 765

Pro Asp Ile Pro Asp Pro Tyr Lys Ser Ser Ile Leu Ser Leu Ile Lys
    770                 775                 780
```

Phe Lys Glu Asn Pro His Leu Thr Ile Met Asn Val Ser Asp Cys Ile
785                 790                 795                 800

Pro Asp Ala Ile Glu Val Val Ser Lys Pro Glu Gly Thr Lys Ile Gln
            805                 810                 815

Leu Leu Gly Thr Arg Lys Ser Leu Thr Glu Thr Glu Leu Thr Lys Pro
        820                 825                 830

Asn Tyr Leu Tyr Leu Leu Pro Thr Glu Lys Asn His Ser Gly Pro Gly
    835                 840                 845

Pro Cys Ile Cys Phe Glu Asn Phe Thr Tyr Asn Gln Ala Ala Ser Asp
850                 855                 860

Ala Gly Ser Cys Gly His Val Pro Val Pro Lys Ala Pro Pro Ser
865                 870                 875                 880

Met Leu Gly Leu Met Thr Ser Pro Glu Asn Val Leu Lys Ala Leu Glu
                885                 890                 895

Lys Asn Tyr Met Asn Ser Leu Gly Glu Val Pro Ala Gly Glu Thr Ser
            900                 905                 910

Leu Asn Tyr Val Ser Gln Leu Ala Ser Pro Met Ser Gly Asp Lys Asp
        915                 920                 925

Ser Leu Pro Thr Asn Pro Val Glu Pro Pro His Cys Ser Glu Tyr Lys
    930                 935                 940

Met Gln Met Ala Val Pro Leu Arg Leu Ala Leu Pro Pro Pro Thr Glu
945                 950                 955                 960

Asn Ser Ser Leu Ser Ser Ile Thr Leu Leu Asp Pro Gly Glu His Tyr
                965                 970                 975

Arg

<210> SEQ ID NO 3
<211> LENGTH: 1356
<212> TYPE: DNA
<213> ORGANISM: Homo sapiens
<220> FEATURE:
<221> NAME/KEY: misc_feature
<223> OTHER INFORMATION: Ab1 Heavy chain

<400> SEQUENCE: 3

```
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacagg ggcttgagtg gatgggatgg atgaacccta tagtggtaa cacagactat     180 gcacagaagt tccagggcag agtcaccatg accaggaaca tttccataag cacggcctac     240
attgagctga gcagcctgag atctgaggac acggccgttt attactgtgc gagagatatg     300
gtggctgcga atacggatta ctacttctac tacggtatgg acgtctgggg ccaagggacc     360
acggtcaccg tctcctcagc tagcaccaag ggcccatcgg tcttccccct ggcgccctgc     420
tccaggagca cctccgagag cacagcggcc ctgggctgcc tggtcaagga ctacttcccc     480
gaaccggtga cggtgtcgtg gaactcaggc gctctgacca gcggcgtgca ccttccca      540 gctgtcctac agtcctcagg actctactcc ctcagcagcg tggtgaccgt gccctccagc     600
aacttcggca cccagaccta cacctgcaac gtagatcaca agcccagcaa caccaaggtg     660
gacaagacag ttgagcgcaa atgttgtgtc gagtgcccac cgtgcccagc accacctgtg     720
gcaggaccgt cagtcttcct cttccccca aaacccaagg acaccctcat gatctcccgg     780
acccctgagg tcacgtgcgt ggtggtggac gtgagccacg aagaccccga ggtccagttc     840
aactggtacg tggacggcgt ggaggtgcat aatgccaaga caaagccacg ggaggagcag     900
```

| | |
|---|---|
| ttcaacagca cgttccgtgt ggtcagcgtc ctcaccgttg tgcaccagga ctggctgaac | 960 |
| ggcaaggagt acaagtgcaa ggtctccaac aaaggcctcc cagccccat cgagaaaacc | 1020 |
| atctccaaaa ccaaagggca gccccgagaa ccacaggtgt acaccctgcc cccatcccgg | 1080 |
| gaggagatga ccaagaacca ggtcagcctg acctgcctgg tcaaaggctt ctaccccagc | 1140 |
| gacatcgccg tggagtggga gagcaatggg cagccggaga caactacaa gaccacacct | 1200 |
| cccatgctgg actccgacgg ctccttcttc ctctacagca agctcaccgt ggacaagagc | 1260 |
| aggtggcagc aggggaacgt cttctcatgc tccgtgatgc atgaggctct gcacaaccac | 1320 |
| tacacgcaga agagcctctc cctgtctccg ggtaaa | 1356 |

<210> SEQ ID NO 4
<211> LENGTH: 1356
<212> TYPE: DNA
<213> ORGANISM: Homo sapiens
<220> FEATURE:
<221> NAME/KEY: misc_feature
<223> OTHER INFORMATION: Ab2 Heavy chain

<400> SEQUENCE: 4

| | |
|---|---|
| caggtgcagc tggtgcagtc tggggctgag gtgaagaagc ctggggcctc agtgaaggtc | 60 |
| tcctgcaagg cttctggata caccttcacc agttatgaaa tcaactgggt gcgacaggcc | 120 |
| actggacaag gcttgagtg gatgggatgg atgaaccta acagtggtta cacaggctat | 180 |
| gcacagaagt tccagggcag agtcaccatg accaggaaca cctccataag cacagcctac | 240 |
| atggaaatga gcagcctgag atctgaggac acggccgtgt attactgtgc gagagatata | 300 |
| gtggctgcga atacggatta ctacttctat tatggtatgg acgtctgggg ccaagggacc | 360 |
| acggtcaccg tctcctcagc tagcaccaag ggcccatcgg tcttccccct ggcgccctgc | 420 |
| tccaggagca cctccgagag cacagcggcc ctgggctgcc tggtcaagga ctacttcccc | 480 |
| gaaccggtga cggtgtcgtg gaactcaggc gctctgacca gcggcgtgca ccttccca | 540 |
| gctgtcctac agtcctcagg actctactcc ctcagcagcg tggtgaccgt gccctccagc | 600 |
| aacttcggca cccagaccta cacctgcaac gtagatcaca gcccagcaa caccaaggtg | 660 |
| gacaagacag ttgagcgcaa atgttgtgtc gagtgcccac cgtgcccagc accacctgtg | 720 |
| gcaggaccgt cagtcttcct cttccccca aacccaagg acaccctcat gatctcccgg | 780 |
| acccctgagg tcacgtgcgt ggtggtggac gtgagccacg aagaccccga ggtccagttc | 840 |
| aactggtacg tggacggcgt ggaggtgcat aatgccaaga caaagccacg ggaggagcag | 900 |
| ttcaacagca cgttccgtgt ggtcagcgtc ctcaccgttg tgcaccagga ctggctgaac | 960 |
| ggcaaggagt acaagtgcaa ggtctccaac aaaggcctcc cagccccat cgagaaaacc | 1020 |
| atctccaaaa ccaaagggca gccccgagaa ccacaggtgt acaccctgcc cccatcccgg | 1080 |
| gaggagatga ccaagaacca ggtcagcctg acctgcctgg tcaaaggctt ctaccccagc | 1140 |
| gacatcgccg tggagtggga gagcaatggg cagccggaga caactacaa gaccacacct | 1200 |
| cccatgctgg actccgacgg ctccttcttc ctctacagca agctcaccgt ggacaagagc | 1260 |
| aggtggcagc aggggaacgt cttctcatgc tccgtgatgc atgaggctct gcacaaccac | 1320 |
| tacacgcaga agagcctctc cctgtctccg ggtaaa | 1356 |

<210> SEQ ID NO 5
<211> LENGTH: 1335
<212> TYPE: DNA
<213> ORGANISM: Homo sapiens
<220> FEATURE:

<221> NAME/KEY: misc_feature
<223> OTHER INFORMATION: Ab3 Heavy chain

<400> SEQUENCE: 5

```
caggttcatc tggtgcagtc tggagctgag gtgaagaagc ctggggcctc agtgaaggtc      60
tcctgcaagg cttctggtta ccctttacc agctatggta tcagctgggt gcgacaggcc     120
cctggacaag gcttgagtg atgggatgg ctcagcactt acagtggtaa cacaaactat      180
gcacagaagc tccagggcag agtcaccatg accacagaca catccacgag cacagcctac     240
atggagctga ggagcctgag atctgacgac acggccgtgt attactgtgc gagagggaac     300
ttctactact acggtatgga cgtctggggc caggggacca cggtcaccgt ctcctcagct     360
agcaccaagg gcccatcggt cttccccctg gcgccctgct ccaggagcac ctccgagagc     420
acagcggccc tgggctgcct ggtcaaggac tacttccccg aaccggtgac ggtgtcgtgg     480
aactcaggcg ctctgaccag cggcgtgcac accttcccag ctgtcctaca gtcctcagga     540
ctctactccc tcagcagcgt ggtgaccgtg ccctccagca acttcggcac ccagacctac     600
acctgcaacg tagatcacaa gcccagcaac accaaggtgg acaagacagt tgagcgcaaa     660
tgttgtgtcg agtgcccacc gtgcccagca ccacctgtgg caggaccgtc agtcttcctc     720
ttccccccaa aacccaagga caccctcatg atctcccgga cccctgaggt cacgtgcgtg     780
gtggtggacg tgagccacga agaccccgag gtccagttca actggtacgt ggacggcgtg     840
gaggtgcata atgccaagac aaagccacgg gaggagcagt tcaacagcac gttccgtgtg     900
gtcagcgtcc tcaccgttgt gcaccaggac tggctgaacg gcaaggagta caagtgcaag     960
gtctccaaca aaggcctccc agcccccatc gagaaaacca tctccaaaac caaagggcag    1020
ccccgagaac acaggtgta caccctgccc ccatcccggg aggagatgac caagaaccag    1080
gtcagcctga cctgcctggt caaaggcttc taccccagcg acatcgccgt ggagtgggag    1140
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                     1335
```

<210> SEQ ID NO 6
<211> LENGTH: 452
<212> TYPE: PRT
<213> ORGANISM: Homo sapiens
<220> FEATURE:
<221> NAME/KEY: MISC_FEATURE
<223> OTHER INFORMATION: Ab1 Heavy chain

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Asp Tyr Ala Gln Lys Phe
    50                  55                  60

Gln Gly Arg Val Thr Met Thr Arg Asn Ile Ser Ile Ser Thr Ala Tyr
65                  70                  75                  80

Ile Glu Leu Ser Ser Leu Arg Ser Glu Asp Thr Ala Val Tyr Tyr Cys
                85                  90                  95
```

```
Ala Arg Asp Met Val Ala Ala Asn Thr Asp Tyr Tyr Phe Tyr Tyr Gly
                100                 105                 110

Met Asp Val Trp Gly Gln Gly Thr Thr Val Thr Val Ser Ser Ala Ser
            115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 7
<211> LENGTH: 452
<212> TYPE: PRT
<213> ORGANISM: Homo sapiens
<220> FEATURE:
<221> NAME/KEY: MISC_FEATURE
<223> OTHER INFORMATION: Ab2 Heavy chain
```

```
<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Glu Ile Asn Trp Val Arg Gln Ala Thr Gly Gln Gly Leu Glu Trp Met
        35                  40                  45

Gly Trp Met Asn Pro Asn Ser Gly Tyr Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Met Ser Ser Leu Arg Ser Glu Asp Thr Ala Val Tyr Tyr Cys
                85                  90                  95

Ala Arg Asp Ile Val Ala Ala Asn Thr Asp Tyr Tyr Phe Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 8
<211> LENGTH: 445
<212> TYPE: PRT
<213> ORGANISM: Homo sapiens
<220> FEATURE:
<221> NAME/KEY: MISC_FEATURE
<223> OTHER INFORMATION: Ab3 Heavy chain

<400> SEQUENCE: 8

Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Leu Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asn Phe Tyr Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys

```
                305                 310                 315                 320
Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 9
<211> LENGTH: 126
<212> TYPE: PRT
<213> ORGANISM: Homo sapiens
<220> FEATURE:
<221> NAME/KEY: MISC_FEATURE
<223> OTHER INFORMATION: Ab1 Heavy chain variable region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Asp Tyr Ala Gln Lys Phe
    50                  55                  60

Gln Gly Arg Val Thr Met Thr Arg Asn Ile Ser Ile Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Asp Met Val Ala Ala Asn Thr Asp Tyr Tyr Phe Tyr Tyr Gly
                100                 105                 110

Met Asp Val Trp Gly Gln Gly Thr Thr Val Thr Val Ser Ser
            115                 120                 125

<210> SEQ ID NO 10
<211> LENGTH: 126
<212> TYPE: PRT
<213> ORGANISM: Homo sapiens
<220> FEATURE:
<221> NAME/KEY: MISC_FEATURE
<223> OTHER INFORMATION: Ab2 Heavy chain variable region

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Glu Ile Asn Trp Val Arg Gln Ala Thr Gly Gln Gly Leu Glu Trp Met
```

```
                    35                  40                  45
Gly Trp Met Asn Pro Asn Ser Gly Tyr Thr Gly Tyr Ala Gln Lys Phe
         50                  55                  60

Gln Gly Arg Val Thr Met Thr Arg Asn Thr Ser Ile Ser Thr Ala Tyr
 65                  70                  75                  80

Met Glu Met Ser Ser Leu Arg Ser Glu Asp Thr Ala Val Tyr Tyr Cys
                 85                  90                  95

Ala Arg Asp Ile Val Ala Ala Asn Thr Asp Tyr Tyr Phe Tyr Tyr Gly
             100                 105                 110

Met Asp Val Trp Gly Gln Gly Thr Thr Val Thr Val Ser Ser
         115                 120                 125

<210> SEQ ID NO 11
<211> LENGTH: 119
<212> TYPE: PRT
<213> ORGANISM: Homo sapiens
<220> FEATURE:
<221> NAME/KEY: MISC_FEATURE
<223> OTHER INFORMATION: Ab3 Heavy chain variable region

<400> SEQUENCE: 11

Gln Val His Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Leu Ser Thr Tyr Ser Gly Asn Thr Asn Tyr Ala Gln Lys Leu
     50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Asn Phe Tyr Tyr Tyr Gly Met Asp Val Trp Gly Gln Gly
             100                 105                 110

Thr Thr Val Thr Val Ser Ser
         115

<210> SEQ ID NO 12
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab1 Heavy chain CDR1

<400> SEQUENCE: 12

Ser Tyr Asp Ile Asn
 1               5

<210> SEQ ID NO 13
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab2 Heavy chain CDR1

<400> SEQUENCE: 13

Ser Tyr Glu Ile Asn
 1               5
```

```
<210> SEQ ID NO 14
<211> LENGTH: 5
<212> TYPE: PRT
<213> ORGANISM: Homo sapiens
<220> FEATURE:
<221> NAME/KEY: MISC_FEATURE
<223> OTHER INFORMATION: Ab3 Heavy chain CDR1

<400> SEQUENCE: 14

Ser Tyr Gly Ile Ser
1               5

<210> SEQ ID NO 15
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab1 Heavy chain CDR2

<400> SEQUENCE: 15

Trp Met Asn Pro Asn Ser Gly Asn Thr Asp Tyr Ala Gln Lys Phe Gln
1               5                   10                  15

Gly

<210> SEQ ID NO 16
<211> LENGTH: 20
<212> TYPE: PRT
<213> ORGANISM: Homo sapiens
<220> FEATURE:
<221> NAME/KEY: MISC_FEATURE
<223> OTHER INFORMATION: Ab2 Heavy chain CDR2

<400> SEQUENCE: 16

Trp Met Gly Trp Met Asn Pro Asn Ser Gly Tyr Thr Gly Tyr Ala Gln
1               5                   10                  15

Lys Phe Gln Gly
            20

<210> SEQ ID NO 17
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab3 Heavy chain CDR2

<400> SEQUENCE: 17

Trp Leu Ser Thr Tyr Ser Gly Asn Thr Asn Tyr Ala Gln Lys Leu Gln
1               5                   10                  15

Gly

<210> SEQ ID NO 18
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab1 Heavy chain CDR3

<400> SEQUENCE: 18

Asp Met Val Ala Ala Asn Thr Asp Tyr Tyr Phe Tyr Tyr Gly Met Asp
1               5                   10                  15

Val
```

<210> SEQ ID NO 19
<211> LENGTH: 17
<212> TYPE: PRT
<213> ORGANISM: Homo sapiens
<220> FEATURE:
<221> NAME/KEY: MISC_FEATURE
<223> OTHER INFORMATION: Ab2 Heavy chain CDR3

<400> SEQUENCE: 19

Asp Ile Val Ala Ala Asn Thr Asp Tyr Tyr Phe Tyr Tyr Gly Met Asp
1               5                   10                  15
Val

<210> SEQ ID NO 20
<211> LENGTH: 10
<212> TYPE: PRT
<213> ORGANISM: Homo sapiens
<220> FEATURE:
<221> NAME/KEY: MISC_FEATURE
<223> OTHER INFORMATION: Ab3 Heavy chain CDR3

<400> SEQUENCE: 20

Gly Asn Phe Tyr Tyr Tyr Gly Met Asp Val
1               5                   10

<210> SEQ ID NO 21
<211> LENGTH: 648
<212> TYPE: DNA
<213> ORGANISM: Homo sapiens
<220> FEATURE:
<221> NAME/KEY: misc_feature
<223> OTHER INFORMATION: Ab1 Light chain

<400> SEQUENCE: 21
cagtctgtgc tgactcagcc accctcagca tctgggaccc ccgggcagag ggtcaccatc      60
tcttgttctg gaagcagctc aacgtcgga agtaatactg taagctggta ccaacagctc     120
ccaggaacgg cccccaaact cctcatctat actaataatc ggcggccctc cggggtccct    180
gaccgattct ctggctccaa gtctggcacc tcagcctccc tggccatcag tgggctccag    240
tctgaggatg aggctgatta tttctgtgca gcgttagatg acagtctgaa tggtgtggta    300
ttcggcggag ggaccaaact gaccgtccta ggccaaccga aagcggcgcc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac acctccaaa caaagcaaca caagtacgc ggccagcagc     540 tatctgagcc tgacgcctga gcagtggaag tcccacagaa gctacagctg ccaggtcacg    600
catgaaggga gcaccgtgga agacagtg gcccctacag aatgttca                  648

<210> SEQ ID NO 22
<211> LENGTH: 648
<212> TYPE: DNA
<213> ORGANISM: Homo sapiens
<220> FEATURE:
<221> NAME/KEY: misc_feature
<223> OTHER INFORMATION: Ab2 Light chain

<400> SEQUENCE: 22
cagtctgtgc tgactcagcc accctcagcg tctgggaccc ccgggcagag ggtcaccatc      60
tcttgttctg gaagcaactc caacatcgga agtaatactg tcaactggta ccaccagctc    120
ccaggaacgg cccccaaact cctcatctat aatattaata agcggccctc agggggtccct    180 gaccgattct ctggctccaa gtctggctcc tcagcctccc tggccatcag tgggctccag    240
tctgaggatg aggctgatta ttactgttca acatgggatg acagcctgga tggtgtggta    300
ttcggcggag ggaccaagct gaccgtccta ggccaaccga aagcggcgcc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca caagtacgc ggccagcagc    540 tatctgagcc tgacgcctga gcagtggaag tcccacagaa gctacagctg ccaggtcacg    600
catgaaggga gcaccgtgga agagacagtg gcccctacag aatgttca    648

<210> SEQ ID NO 23
<211> LENGTH: 648
<212> TYPE: DNA
<213> ORGANISM: Homo sapiens
<220> FEATURE:
<221> NAME/KEY: misc_feature
<223> OTHER INFORMATION: Ab3 Light chain

<400> SEQUENCE: 23
gaaattgtgt tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatcttt ggtgcttcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcgcctcc gatcaccttc    300
ggccaaggga cacgactgga gattaaacgt acggtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt    648

<210> SEQ ID NO 24
<211> LENGTH: 216
<212> TYPE: PRT
<213> ORGANISM: Homo sapiens
<220> FEATURE:
<221> NAME/KEY: MISC_FEATURE
<223> OTHER INFORMATION: Ab1 Light chain

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Val Gly Ser Asn
            20                  25                  30

Thr Val Ser Trp Tyr Gln Gln Leu Pro Gly Thr Ala Pro Lys Leu Leu
        35                  40                  45

Ile Tyr Thr Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Leu Asp Asp Ser Leu
                85                  90                  95

Asn Gly Val Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 25
<211> LENGTH: 216
<212> TYPE: PRT
<213> ORGANISM: Homo sapiens
<220> FEATURE:
<221> NAME/KEY: MISC_FEATURE
<223> OTHER INFORMATION: Ab2 Light chain

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Thr Val Asn Trp Tyr His Gln Leu Pro Gly Thr Ala Pro Lys Leu Leu
            35                  40                  45

Ile Tyr Asn Ile Asn Lys Arg Pro Ser Gly Val Pro Asp Arg Phe Ser
        50                  55                  60

Gly Ser Lys Ser Gly Ser Ser Ala Ser Leu Ala Ile Ser Gly Leu Gln
65                  70                  75                  80

Ser Glu Asp Glu Ala Asp Tyr Tyr Cys Ser Thr Trp Asp Asp Ser Leu
            85                  90                  95

Asp Gly Val Val Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

-continued

```
<210> SEQ ID NO 26
<211> LENGTH: 216
<212> TYPE: PRT
<213> ORGANISM: Homo sapiens
<220> FEATURE:
<221> NAME/KEY: MISC_FEATURE
<223> OTHER INFORMATION: Ab3 light chain

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Ile Thr Phe Gly Gln Gly Thr Arg Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 27
<211> LENGTH: 111
<212> TYPE: PRT
<213> ORGANISM: Homo sapiens
<220> FEATURE:
<221> NAME/KEY: MISC_FEATURE
<223> OTHER INFORMATION: Ab1 Light chain variable

<400> SEQUENCE: 27

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Val Gly Ser Asn
            20                  25                  30

Thr Val Ser Trp Tyr Gln Gln Leu Pro Gly Thr Ala Pro Lys Leu Leu
        35                  40                  45

Ile Tyr Thr Asn Asn Arg Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Ala Leu Asp Asp Ser Leu
```

```
                     85                  90                  95
Asn Gly Val Val Phe Gly Gly Gly Thr Lys Leu Thr Val Leu Gly
                100                 105                 110
```

<210> SEQ ID NO 28
<211> LENGTH: 111
<212> TYPE: PRT
<213> ORGANISM: Homo sapiens
<220> FEATURE:
<221> NAME/KEY: MISC_FEATURE
<223> OTHER INFORMATION: Ab2 Light chain variable

<400> SEQUENCE: 28

```
Gln Ser Val Leu Thr Gln Pro Pro Ser Ala Ser Gly Thr Pro Gly Gln
  1               5                  10                  15

Arg Val Thr Ile Ser Cys Ser Gly Ser Asn Ser Asn Ile Gly Ser Asn
                 20                  25                  30

Thr Val Asn Trp Tyr His Gln Leu Pro Gly Thr Ala Pro Lys Leu Leu
             35                  40                  45

Ile Tyr Asn Ile Asn Lys Arg Pro Ser Gly Val Pro Asp Arg Phe Ser
         50                  55                  60

Gly Ser Lys Ser Gly Ser Ser Ala Ser Leu Ala Ile Ser Gly Leu Gln
 65                  70                  75                  80

Ser Glu Asp Glu Ala Asp Tyr Tyr Cys Ser Thr Trp Asp Asp Ser Leu
                 85                  90                  95

Asp Gly Val Val Phe Gly Gly Gly Thr Lys Leu Thr Val Leu Gly
                100                 105                 110
```

<210> SEQ ID NO 29
<211> LENGTH: 110
<212> TYPE: PRT
<213> ORGANISM: Homo sapiens
<220> FEATURE:
<221> NAME/KEY: MISC_FEATURE
<223> OTHER INFORMATION: Ab3 Light chain variable

<400> SEQUENCE: 29

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Phe Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Ile Thr Phe Gly Gln Gly Thr Arg Leu Glu Ile Lys Arg
                100                 105                 110
```

<210> SEQ ID NO 30
<211> LENGTH: 13
<212> TYPE: PRT
<213> ORGANISM: Homo sapiens
<220> FEATURE:
<221> NAME/KEY: MISC_FEATURE
<223> OTHER INFORMATION: Ab1 Light chain CDR1

<400> SEQUENCE: 30

```
Ser Gly Ser Ser Ser Asn Val Gly Ser Asn Thr Val Ser
1               5                   10

<210> SEQ ID NO 31
<211> LENGTH: 13
<212> TYPE: PRT
<213> ORGANISM: Homo sapiens
<220> FEATURE:
<221> NAME/KEY: MISC_FEATURE
<223> OTHER INFORMATION: Ab2 Light chain CDR1

<400> SEQUENCE: 31

Ser Gly Ser Asn Ser Asn Ile Gly Ser Asn Thr Val Asn
1               5                   10

<210> SEQ ID NO 32
<211> LENGTH: 12
<212> TYPE: PRT
<213> ORGANISM: Homo sapiens
<220> FEATURE:
<221> NAME/KEY: MISC_FEATURE
<223> OTHER INFORMATION: Ab3 Light chain CDR1

<400> SEQUENCE: 32

Arg Ala Ser Gln Ser Val Ser Ser Ser Tyr Leu Ala
1               5                   10

<210> SEQ ID NO 33
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab1 Light chain CDR2

<400> SEQUENCE: 33

Thr Asn Asn Arg Arg Pro Ser
1               5

<210> SEQ ID NO 34
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab2 Light chain CDR2

<400> SEQUENCE: 34

Asn Ile Asn Lys Arg Pro Ser
1               5

<210> SEQ ID NO 35
<211> LENGTH: 7
<212> TYPE: PRT
<213> ORGANISM: Homo sapiens
<220> FEATURE:
<221> NAME/KEY: MISC_FEATURE
<223> OTHER INFORMATION: Ab3 Light chain CDR2

<400> SEQUENCE: 35

Gly Ala Ser Ser Arg Ala Thr
1               5

<210> SEQ ID NO 36
<211> LENGTH: 11
<212> TYPE: PRT
<213> ORGANISM: Homo sapiens
```

```
<220> FEATURE:
<221> NAME/KEY: MISC_FEATURE
<223> OTHER INFORMATION: Ab1 Light chain CDR3

<400> SEQUENCE: 36

Ala Ala Leu Asp Asp Ser Leu Asn Gly Val Val
1               5                   10

<210> SEQ ID NO 37
<211> LENGTH: 11
<212> TYPE: PRT
<213> ORGANISM: Homo sapiens
<220> FEATURE:
<221> NAME/KEY: MISC_FEATURE
<223> OTHER INFORMATION: Ab2 Light chain CDR3

<400> SEQUENCE: 37

Ser Thr Trp Asp Asp Ser Leu Asp Gly Val Val
1               5                   10

<210> SEQ ID NO 38
<211> LENGTH: 10
<212> TYPE: PRT
<213> ORGANISM: Homo sapiens
<220> FEATURE:
<221> NAME/KEY: MISC_FEATURE
<223> OTHER INFORMATION: Ab3 Light chain CDR3

<400> SEQUENCE: 38

Gln Gln Tyr Gly Ser Ser Pro Pro Ile Thr
1               5                   10

<210> SEQ ID NO 39
<211> LENGTH: 252
<212> TYPE: PRT
<213> ORGANISM: Homo sapiens
<220> FEATURE:
<221> NAME/KEY: MISC_FEATURE
<223> OTHER INFORMATION: Human OSM

<400> SEQUENCE: 39

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
```

```
                        165                 170                 175
Thr Pro Thr Pro Ala Ser Asp Ala Phe Gln Arg Lys Leu Glu Gly Cys
                180                 185                 190

Arg Phe Leu His Gly Tyr His Arg Phe Met His Ser Val Gly Arg Val
            195                 200                 205

Phe Ser Lys Trp Gly Glu Ser Pro Asn Arg Ser Arg Arg His Ser Pro
        210                 215                 220

His Gln Ala Leu Arg Lys Gly Val Arg Thr Arg Pro Ser Arg Lys
225                 230                 235                 240

Gly Lys Arg Leu Met Thr Arg Gly Gln Leu Pro Arg
                245                 250

<210> SEQ ID NO 40
<211> LENGTH: 196
<212> TYPE: PRT
<213> ORGANISM: Macaca fascicularis
<220> FEATURE:
<221> NAME/KEY: MISC_FEATURE
<223> OTHER INFORMATION: Cynomolgus monkey OSM protein

<400> SEQUENCE: 40

Ala Ala Met Gly Ser Cys Ser Lys Glu Tyr Arg Met Leu Leu Gly Gln
1               5                   10                  15

Leu Gln Lys Gln Thr Asp Leu Met Gln Asp Thr Ser Arg Leu Leu Asp
                20                  25                  30

Pro Tyr Ile Arg Ile Gln Gly Leu Asp Ile Pro Lys Leu Arg Glu His
            35                  40                  45

Cys Arg Glu Ser Pro Gly Ala Phe Pro Ser Glu Thr Leu Arg Gly
        50                  55                  60

Leu Gly Arg Arg Gly Phe Leu Gln Thr Leu Asn Ala Thr Leu Gly Arg
65                  70                  75                  80

Ile Leu His Arg Leu Ala Asp Leu Glu Gln His Leu Pro Lys Ala Gln
                85                  90                  95

Asp Leu Glu Arg Ser Gly Leu Asn Ile Glu Asp Leu Glu Lys Leu Gln
            100                 105                 110

Met Ala Arg Pro Asn Val Leu Gly Leu Arg Asn Asn Val Tyr Cys Met
        115                 120                 125

Ala Gln Leu Leu Asp Asn Ser Asp Met Thr Glu Pro Thr Lys Ala Gly
130                 135                 140

Arg Gly Thr Pro Gln Pro Pro Thr Pro Thr Pro Thr Ser Asp Val Phe
145                 150                 155                 160

Gln Arg Lys Leu Glu Gly Cys Ser Phe Leu Arg Gly Tyr His Arg Phe
                165                 170                 175

Met His Ser Val Gly Arg Val Phe Ser Lys Trp Gly Glu Ser Pro Asn
            180                 185                 190

Arg Ser Arg Arg
        195

<210> SEQ ID NO 41
<211> LENGTH: 164
<212> TYPE: PRT
<213> ORGANISM: Homo sapiens
<220> FEATURE:
<221> NAME/KEY: MISC_FEATURE
<223> OTHER INFORMATION: Human IL-31

<400> SEQUENCE: 41

Met Ala Ser His Ser Gly Pro Ser Thr Ser Val Leu Phe Leu Phe Cys
```

```
            1               5                  10                 15
        Cys Leu Gly Gly Trp Leu Ala Ser His Thr Leu Pro Val Arg Leu Leu
                        20                 25                 30

Arg Pro Ser Asp Asp Val Gln Lys Ile Val Glu Glu Leu Gln Ser Leu
                    35                 40                 45

Ser Lys Met Leu Leu Lys Asp Val Glu Glu Lys Gly Val Leu Val
                50                 55                 60

Ser Gln Asn Tyr Thr Leu Pro Cys Leu Ser Pro Asp Ala Gln Pro Pro
         65                 70                 75                 80

Asn Asn Ile His Ser Pro Ala Ile Arg Ala Tyr Leu Lys Thr Ile Arg
                        85                 90                 95

Gln Leu Asp Asn Lys Ser Val Ile Asp Glu Ile Ile Glu His Leu Asp
                    100                105                110

Lys Leu Ile Phe Gln Asp Ala Pro Glu Thr Asn Ile Ser Val Pro Thr
                    115                120                125

Asp Thr His Glu Cys Lys Arg Phe Ile Leu Thr Ile Ser Gln Gln Phe
            130                135                140

Ser Glu Cys Met Asp Leu Ala Leu Lys Ser Leu Thr Ser Gly Ala Gln
        145                150                155                160

Gln Ala Thr Thr
```

<210> SEQ ID NO 42
<211> LENGTH: 138
<212> TYPE: PRT
<213> ORGANISM: Macaca fascicularis
<220> FEATURE:
<221> NAME/KEY: MISC_FEATURE
<223> OTHER INFORMATION: Cynomolgus monkey IL-31

<400> SEQUENCE: 42

```
        Thr Leu Pro Val His Phe Leu Gln Pro Ser Asp Ile Gln Lys Ile Val
         1               5                  10                 15

Glu Glu Leu Gln Ser Leu Ser Lys Met Leu Leu Lys Asp Val Lys Glu
                        20                 25                 30

Asp Lys Gly Val Leu Val Ser Gln Asn Tyr Thr Leu Pro Cys Leu Thr
                    35                 40                 45

Pro Asp Ala Gln Pro Pro Asn Ile Ile His Ser Pro Ala Ile Arg Ala
                50                 55                 60

Tyr Leu Lys Thr Ile Arg Gln Leu Asp Asn Lys Ser Val Ile Asp Glu
         65                 70                 75                 80

Ile Ile Glu His Leu Asp Lys Leu Ile Phe Gln Asp Ala Pro Glu Thr
                        85                 90                 95

Asn Ile Ser Val Pro Thr Asp Thr His Glu Cys Lys Arg Phe Ile Leu
                    100                105                110

Thr Ile Ser Gln Gln Phe Ser Glu Cys Met Asp Leu Ala Leu Lys Ser
                    115                120                125

Leu Thr Ser Gly Ala Gln Gln Ala Thr Thr
                130                135
```

<210> SEQ ID NO 43
<211> LENGTH: 662
<212> TYPE: PRT
<213> ORGANISM: Homo sapiens
<220> FEATURE:
<221> NAME/KEY: MISC_FEATURE
<223> OTHER INFORMATION: Human IL-31RA

<400> SEQUENCE: 43

```
Met Lys Leu Ser Pro Gln Pro Ser Cys Val Asn Leu Gly Met Met Trp
1               5                   10                  15
Thr Trp Ala Leu Trp Met Leu Pro Ser Leu Cys Lys Phe Ser Leu Ala
            20                  25                  30
Ala Leu Pro Ala Lys Pro Glu Asn Ile Ser Cys Val Tyr Tyr Tyr Arg
            35                  40                  45
Lys Asn Leu Thr Cys Thr Trp Ser Pro Gly Lys Glu Thr Ser Tyr Thr
50                  55                  60
Gln Tyr Thr Val Lys Arg Thr Tyr Ala Phe Gly Lys His Asp Asn
65                  70                  75                  80
Cys Thr Thr Asn Ser Ser Thr Ser Glu Asn Arg Ala Ser Cys Ser Phe
                85                  90                  95
Phe Leu Pro Arg Ile Thr Ile Pro Asp Asn Tyr Thr Ile Glu Val Glu
            100                 105                 110
Ala Glu Asn Gly Asp Gly Val Ile Lys Ser His Met Thr Tyr Trp Arg
            115                 120                 125
Leu Glu Asn Ile Ala Lys Thr Glu Pro Pro Lys Ile Phe Arg Val Lys
            130                 135                 140
Pro Val Leu Gly Ile Lys Arg Met Ile Gln Ile Glu Trp Ile Lys Pro
145                 150                 155                 160
Glu Leu Ala Pro Val Ser Ser Asp Leu Lys Tyr Thr Leu Arg Phe Arg
                165                 170                 175
Thr Val Asn Ser Thr Ser Trp Met Glu Val Asn Phe Ala Lys Asn Arg
            180                 185                 190
Lys Asp Lys Asn Gln Thr Tyr Asn Leu Thr Gly Leu Gln Pro Phe Thr
            195                 200                 205
Glu Tyr Val Ile Ala Leu Arg Cys Ala Val Lys Glu Ser Lys Phe Trp
210                 215                 220
Ser Asp Trp Ser Gln Glu Lys Met Gly Met Thr Glu Glu Ala Pro
225                 230                 235                 240
Cys Gly Leu Glu Leu Trp Arg Val Leu Lys Pro Ala Glu Ala Asp Gly
                245                 250                 255
Arg Arg Pro Val Arg Leu Leu Trp Lys Lys Ala Arg Gly Ala Pro Val
            260                 265                 270
Leu Glu Lys Thr Leu Gly Tyr Asn Ile Trp Tyr Tyr Pro Glu Ser Asn
            275                 280                 285
Thr Asn Leu Thr Glu Thr Met Asn Thr Thr Asn Gln Gln Leu Glu Leu
            290                 295                 300
His Leu Gly Gly Glu Ser Phe Trp Val Ser Met Ile Ser Tyr Asn Ser
305                 310                 315                 320
Leu Gly Lys Ser Pro Val Ala Thr Leu Arg Ile Pro Ala Ile Gln Glu
            325                 330                 335
Lys Ser Phe Gln Cys Ile Glu Val Met Gln Ala Cys Val Ala Glu Asp
            340                 345                 350
Gln Leu Val Val Lys Trp Gln Ser Ser Ala Leu Asp Val Asn Thr Trp
            355                 360                 365
Met Ile Glu Trp Phe Pro Asp Val Asp Ser Glu Pro Thr Thr Leu Ser
            370                 375                 380
Trp Glu Ser Val Ser Gln Ala Thr Asn Trp Thr Ile Gln Gln Asp Lys
385                 390                 395                 400
Leu Lys Pro Phe Trp Cys Tyr Asn Ile Ser Val Tyr Pro Met Leu His
                405                 410                 415
```

-continued

Asp Lys Val Gly Glu Pro Tyr Ser Ile Gln Ala Tyr Ala Lys Glu Gly
                420                 425                 430

Val Pro Ser Glu Gly Pro Glu Thr Lys Val Glu Asn Ile Gly Val Lys
            435                 440                 445

Thr Val Thr Ile Thr Trp Lys Glu Ile Pro Lys Ser Glu Arg Lys Gly
        450                 455                 460

Ile Ile Cys Asn Tyr Thr Ile Phe Tyr Gln Ala Glu Gly Gly Lys Gly
465                 470                 475                 480

Phe Ser Lys Thr Val Asn Ser Ser Ile Leu Gln Tyr Gly Leu Glu Ser
                485                 490                 495

Leu Lys Arg Lys Thr Ser Tyr Ile Val Gln Val Met Ala Ser Thr Ser
            500                 505                 510

Ala Gly Gly Thr Asn Gly Thr Ser Ile Asn Phe Lys Thr Leu Ser Phe
        515                 520                 525

Ser Val Phe Glu Ile Ile Leu Ile Thr Ser Leu Ile Gly Gly Gly Leu
530                 535                 540

Leu Ile Leu Ile Ile Leu Thr Val Ala Tyr Gly Leu Lys Lys Pro Asn
545                 550                 555                 560

Lys Leu Thr His Leu Cys Trp Pro Thr Val Pro Asn Pro Ala Glu Ser
                565                 570                 575

Ser Ile Ala Thr Trp His Gly Asp Asp Phe Lys Asp Lys Leu Asn Leu
            580                 585                 590

Lys Glu Ser Asp Asp Ser Val Asn Thr Glu Asp Arg Ile Leu Lys Pro
        595                 600                 605

Cys Ser Thr Pro Ser Asp Lys Leu Val Ile Asp Lys Leu Val Val Asn
610                 615                 620

Phe Gly Asn Val Leu Gln Glu Ile Phe Thr Asp Glu Ala Arg Thr Gly
625                 630                 635                 640

Gln Glu Asn Asn Leu Gly Gly Glu Lys Asn Gly Thr Arg Ile Leu Ser
                645                 650                 655

Ser Cys Pro Thr Ser Ile
            660

<210> SEQ ID NO 44
<211> LENGTH: 649
<212> TYPE: PRT
<213> ORGANISM: Macaca fascicularis
<220> FEATURE:
<221> NAME/KEY: MISC_FEATURE
<223> OTHER INFORMATION: Cynomolgus monkey IL-21RA

<400> SEQUENCE: 44

Met Met Trp Thr Trp Ala Leu Trp Met Phe Pro Leu Leu Cys Lys Phe
1               5                   10                  15

Gly Leu Ala Ala Leu Pro Ala Lys Pro Glu Asn Ile Ser Cys Val Tyr
            20                  25                  30

Tyr Tyr Arg Lys Asn Leu Thr Cys Thr Trp Ser Pro Gly Lys Glu Thr
        35                  40                  45

Ser Tyr Thr Gln Tyr Thr Ala Lys Arg Thr Tyr Ala Phe Gly Lys Lys
    50                  55                  60

His Asp Asn Cys Thr Thr Ser Ser Thr Ser Glu Asn Arg Ala Ser
65                  70                  75                  80

Cys Ser Phe Phe Leu Pro Arg Ile Thr Ile Pro Asp Asn Tyr Thr Ile
                85                  90                  95

Glu Val Glu Ala Glu Asn Gly Asp Gly Val Ile Lys Ser Asp Met Thr
            100                 105                 110

Cys Trp Arg Leu Glu Asp Ile Ala Lys Thr Glu Pro Pro Glu Ile Phe
            115                 120                 125

Ser Val Lys Pro Val Leu Gly Ile Lys Arg Met Ile Arg Ile Glu Trp
            130                 135                 140

Ile Lys Pro Glu Leu Ala Pro Val Ser Ser Asp Leu Lys Tyr Ala Leu
145                 150                 155                 160

Arg Phe Arg Thr Val Asn Ser Thr Ser Trp Met Glu Val Asn Phe Ala
                165                 170                 175

Lys Asn Arg Lys Asp Thr Asn Gln Thr Tyr Asn Leu Met Gly Leu Gln
                180                 185                 190

Ala Phe Thr Glu Tyr Val Val Ala Leu Arg Cys Ala Val Lys Glu Ser
                195                 200                 205

Lys Phe Trp Ser Asp Trp Ser Gln Glu Lys Met Gly Met Thr Glu Glu
                210                 215                 220

Glu Ala Pro Cys Gly Leu Glu Leu Trp Arg Val Leu Lys Pro Thr Glu
225                 230                 235                 240

Val Asp Gly Arg Arg Pro Val Arg Leu Leu Trp Lys Lys Ala Arg Gly
                245                 250                 255

Ala Pro Val Leu Glu Lys Thr Leu Gly Tyr Asn Ile Trp Tyr Phe Pro
                260                 265                 270

Glu Asn Asn Thr Asn Leu Thr Glu Thr Val Asn Thr Thr Asn Gln Gln
                275                 280                 285

Leu Glu Leu His Leu Gly Gly Glu Ser Tyr Trp Val Ser Met Ile Ser
                290                 295                 300

Tyr Asn Ser Leu Gly Lys Ser Pro Val Thr Thr Leu Arg Ile Pro Ala
305                 310                 315                 320

Ile Gln Glu Lys Ser Phe Arg Cys Ile Glu Val Met Gln Ala Cys Leu
                325                 330                 335

Ala Glu Asp Gln Leu Val Val Lys Trp Gln Ser Ser Ala Leu Asp Val
                340                 345                 350

Asn Thr Trp Met Ile Glu Trp Phe Pro Asp Met Asp Ser Glu His Pro
                355                 360                 365

Thr Leu Ser Trp Glu Ser Val Ser Gln Ala Thr Asn Trp Thr Ile Gln
                370                 375                 380

Gln Asp Lys Leu Lys Pro Phe Trp Cys Tyr Asn Ile Ser Val Tyr Pro
385                 390                 395                 400

Met Leu His Asp Lys Val Gly Glu Pro Tyr Ser Ile Gln Ala Tyr Ala
                405                 410                 415

Lys Glu Gly Ile Pro Ser Lys Gly Pro Glu Thr Lys Val Glu Asn Ile
                420                 425                 430

Gly Val Lys Thr Val Thr Ile Thr Trp Lys Glu Ile Pro Lys Ser Glu
                435                 440                 445

Arg Lys Gly Ile Ile Cys Asn Tyr Thr Ile Phe Tyr Gln Ala Glu Gly
                450                 455                 460

Gly Thr Gly Phe Ser Lys Thr Val Asn Ser Ser Ile Leu Gln Tyr Gly
465                 470                 475                 480

Leu Glu Ser Leu Lys Arg Lys Thr Ser Tyr Thr Val Arg Val Met Ala
                485                 490                 495

Ser Thr Ser Ala Gly Gly Ile Asn Gly Thr Ser Ile Asn Phe Lys Thr
                500                 505                 510

Leu Ser Phe Ser Val Phe Glu Ile Ile Leu Ile Thr Ser Leu Ile Gly
                515                 520                 525

```
Gly Gly Leu Leu Ile Leu Ile Ile Leu Thr Val Ala Tyr Gly Leu Lys
            530                 535                 540

Lys Pro Asn Lys Leu Thr His Leu Cys Trp Pro Ser Val Pro Asn Pro
545                 550                 555                 560

Ala Glu Ser Ser Ile Ala Thr Trp Arg Gly Asp Asp Phe Lys Asp Lys
                565                 570                 575

Leu Asn Leu Lys Glu Ser Asp Ser Val Asn Thr Glu Asp Arg Ile
            580                 585                 590

Leu Lys Pro Cys Ser Thr Pro Ser Asp Lys Leu Val Ile Asp Lys Ser
                595                 600                 605

Val Val Asn Phe Gly Asn Val Leu Gln Glu Met Phe Thr Asp Glu Ala
            610                 615                 620

Arg Thr Gly Gln Glu Asn Asn Leu Gly Gly Glu Lys Asn Glu Asn Arg
625                 630                 635                 640

Ile Leu Ser Ser Cys Pro Thr Ser Ile
                645
```

<210> SEQ ID NO 45
<211> LENGTH: 918
<212> TYPE: PRT
<213> ORGANISM: Homo sapiens
<220> FEATURE:
<221> NAME/KEY: MISC_FEATURE
<223> OTHER INFORMATION: Human gp130

<400> SEQUENCE: 45

```
Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240
```

```
Lys Leu Thr Trp Thr Asn Pro Ser Ile Lys Ser Val Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
                275                 280                 285

Leu Lys Pro Phe Thr Glu Tyr Val Phe Arg Ile Arg Cys Met Lys Glu
            290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
                355                 360                 365

Thr Leu Thr Arg Trp Lys Ser His Leu Gln Asn Tyr Thr Val Asn Ala
                370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
                435                 440                 445

Ser Val Lys Lys Tyr Ile Leu Glu Trp Cys Val Leu Ser Asp Lys Ala
                450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
                500                 505                 510

Tyr Leu Lys Gln Ala Pro Pro Ser Lys Gly Pro Thr Val Arg Thr Lys
                515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
                580                 585                 590

Ala Ala Tyr Thr Asp Glu Gly Gly Lys Asp Gly Pro Glu Phe Thr Phe
                595                 600                 605

Thr Thr Pro Lys Phe Ala Gln Gly Glu Ile Glu Ala Ile Val Val Pro
            610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655
```

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Ser Asn Phe
            675                 680                 685

Thr Asp Val Ser Val Val Glu Ile Val Ala Asn Asp Lys Lys Pro Phe
            690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
            725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
            770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
            805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
            885                 890                 895

Thr Asp Glu Gly Met Pro Lys Ser Tyr Leu Pro Gln Thr Val Arg Gln
            900                 905                 910

Gly Gly Tyr Met Pro Gln
            915

<210> SEQ ID NO 46
<211> LENGTH: 918
<212> TYPE: PRT
<213> ORGANISM: Macaca fascicularis
<220> FEATURE:
<221> NAME/KEY: MISC_FEATURE
<223> OTHER INFORMATION: Cynomolgus monkey gp130

<400> SEQUENCE: 46

Met Leu Thr Leu Gln Thr Trp Val Val Gln Ala Leu Phe Ile Phe Leu
1               5                   10                  15

Thr Thr Glu Ser Ile Gly Glu Leu Leu Asp Pro Cys Gly Tyr Ile Ser
            20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ser Ser
                85                  90                  95

```
Leu Asn Ile Gln Leu Thr Cys Asn Ile Leu Thr Phe Gly Gln Leu Glu
                100                 105                 110

Gln Asn Val Tyr Gly Ile Thr Ile Ile Ser Gly Leu Pro Pro Glu Lys
            115                 120                 125

Pro Lys Asn Leu Ser Cys Ile Val Asn Glu Gly Lys Lys Met Arg Cys
        130                 135                 140

Glu Trp Asn Arg Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Arg Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Cys Cys Met Lys Glu
    290                 295                 300

Asp Gly Lys Gly Tyr Trp Ser Asp Trp Ser Glu Glu Ala Asn Gly Ile
305                 310                 315                 320

Thr Tyr Glu Asp Arg Pro Ser Lys Ala Pro Ser Phe Trp Tyr Lys Ile
                325                 330                 335

Asp Pro Ser His Ala Gln Gly Tyr Arg Thr Val Gln Leu Met Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Asp
    370                 375                 380

Thr Lys Leu Thr Val Asn Leu Thr Asn Asp Arg Tyr Val Ala Thr Leu
385                 390                 395                 400

Thr Ala Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Ala Asp Trp Gln Gln Glu Asp Gly Thr Val His Arg Thr
465                 470                 475                 480

His Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510
```

```
Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Ser Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Ser Asp Asp Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Glu
850                 855                 860

Met Lys Met Phe Gln Glu Val Ser Ala Ala Asp Pro Phe Gly Pro Gly
865                 870                 875                 880

Thr Glu Gly Gln Val Glu Arg Phe Glu Thr Ile Gly Met Glu Ala Ala
                885                 890                 895

Ile Asp Glu Gly Met Pro Lys Ser Tyr Leu Pro Gln Thr Val Arg Gln
            900                 905                 910

Gly Gly Tyr Met Pro Gln
            915
```

<210> SEQ ID NO 47
<211> LENGTH: 1353
<212> TYPE: DNA
<213> ORGANISM: Artificial Sequence
<220> FEATURE:
<223> OTHER INFORMATION: Synthetic polynucleotide

<400> SEQUENCE: 47

```
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacagg ggcttgagtg gatgggatgg atgaaccctg atagtggtaa cacagactat     180
gcacagaagt tccagggcag agtcaccatg accagggaca tttccataag cacggcctac     240
attgagctga gcagcctgag atctgaggac acggccgttt attactgtgc gagagatatg     300
gtggctgcga atacggatta ctacttctac tacggtatgg acgtctgggg ccaagggacc     360
acggtcaccg tctcctcagc tagcaccaag ggcccatcgg tcttccccct ggcgccctgc     420
tccaggagca cctccgagag cacagcggcc ctgggctgcc tggtcaagga ctacttcccc     480
gaaccggtga cggtgtcgtg gaactcaggc gctctgacca gcggcgtgca caccttccca     540
gctgtcctac agtcctcagg actctactcc ctcagcagcg tggtgaccgt gccctccagc     600
aacttcggca cccagaccta cacctgcaac gtagatcaca agcccagcaa caccaaggtg     660
gacaagacag ttgagcgcaa atgttgtgtc gagtgcccac cgtgcccagc accacctgtg     720
gcaggaccgt cagtcttcct cttccccccA aaacccaagg acaccctcat gatctcccgg     780
acccctgagg tcacgtgcgt ggtggtggac gtgagccacg aagaccccga ggtccagttc     840
aactggtacg tggacggcgt ggaggtgcat aatgccaaga caaagccacg ggaggagcag     900
ttcaacagca cgttccgtgt ggtcagcgtc ctcaccgttg tgcaccagga ctggctgaac     960
ggcaaggagt acaagtgcaa ggtctccaac aaaggcctcc cagcccccat cgagaaaacc    1020
atctccaaaa ccaaagggca gccccgagaa ccacaggtgt acaccctgcc cccatcccgg    1080
gaggagatga ccaagaacca ggtcagcctg acctgcctgg tcaaaggctt ctaccccagc    1140
gacatcgccg tggagtggga gagcaatggg cagccggaga acaactacaa gaccacacct    1200
cccatgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggt                                 1353
```

<210> SEQ ID NO 48
<211> LENGTH: 1353
<212> TYPE: DNA
<213> ORGANISM: Artificial Sequence
<220> FEATURE:
<223> OTHER INFORMATION: Synthetic polynucleotide

<400> SEQUENCE: 48

```
caggtgcagc tggtgcagtc tggggctgag gtgaagaagc ctggggcctc agtgaaggtc      60
tcctgcaagg cttctggata caccttcacc agttatgaaa tcaactgggt gcgacaggcc     120
actggacaag ggcttgagtg gatgggatgg atgaaccctg acagtggtta cacaggctat     180
gcacagaagt tccagggcag agtcaccatg accagggaca cctccataag cacagcctac     240
atggaaatga gcagcctgag atctgaggac acggccgtgt attactgtgc gagagatata     300
gtggctgcga atacggatta ctacttctat tatggtatgg acgtctgggg ccaagggacc     360
acggtcaccg tctcctcagc tagcaccaag ggcccatcgg tcttccccct ggcgccctgc     420
```

```
tccaggagca cctccgagag cacagcggcc ctgggctgcc tggtcaagga ctacttcccc      480
gaaccggtga cggtgtcgtg gaactcaggc gctctgacca cggcgtgca cccttccca       540 gctgtcctac agtcctcagg actctactcc ctcagcagcg tggtgaccgt gccctccagc      600
aacttcggca cccagaccta cacctgcaac gtagatcaca agcccagcaa caccaaggtg      660
gacaagacag ttgagcgcaa atgttgtgtc gagtgcccac cgtgcccagc accacctgtg      720
gcaggaccgt cagtcttcct cttccccca aaacccaagg acaccctcat gatctcccgg       780 accctgagg tcacgtgcgt ggtggtggac gtgagccacg aagaccccga ggtccagttc       840
aactggtacg tggacggcgt ggaggtgcat aatgccaaga caaagccacg ggaggagcag      900
ttcaacagca cgttccgtgt ggtcagcgtc ctcaccgttg tgcaccagga ctggctgaac      960
ggcaaggagt acaagtgcaa ggtctccaac aaaggcctcc cagcccccat cgagaaaacc     1020
atctccaaaa ccaaagggca gccccgagaa ccacaggtgt acaccctgcc cccatcccgg     1080
gaggagatga ccaagaacca ggtcagcctg acctgcctgg tcaaaggctt ctaccccagc     1140
gacatcgccg tggagtggga gagcaatggg cagccggaga caactacaa gaccacacct      1200 cccatgctgg actccgacgg ctccttcttc ctctacagca agctcaccgt ggacaagagc     1260
aggtggcagc aggggaacgt cttctcatgc tccgtgatgc atgaggctct gcacaaccac     1320
tacacgcaga gagcctctc cctgtctccg ggt                                   1353

<210> SEQ ID NO 49
<211> LENGTH: 1332
<212> TYPE: DNA
<213> ORGANISM: Artificial Sequence
<220> FEATURE:
<223> OTHER INFORMATION: Synthetic polynucleotide

<400> SEQUENCE: 49
caggttcatc tggtgcagtc tggagctgag gtgaagaagc ctggggcctc agtgaaggtc       60
tcctgcaagg cttctggtta ccctttacc agctatggta tcagctgggt gcgacaggcc      120
cctggacaag gcttgagtg gatgggatgg ctcagcactt acagtggtaa cacaaactat      180
gcacagaagc tccagggcag agtcaccatg accacagaca catccacgag cacagcctac      240
atggagctga ggagcctgag atctgacgac acggccgtgt attactgtgc gagagggaac      300
ttctactact acggtatgga cgtctggggc caggggacca cggtcaccgt ctcctcagct      360
agcaccaagg gcccatcggt cttccccctg gcgccctgct ccaggagcac ctccgagagc      420
acagcggccc tgggctgcct ggtcaaggac tacttcccg aaccggtgac ggtgtcgtgg       480
aactcaggcg ctctgaccag cggcgtgcac accttcccag ctgtcctaca gtcctcagga      540
ctctactccc tcagcagcgt ggtgaccgtg ccctccagca acttcggcac ccagacctac      600
acctgcaacg tagatcacaa gcccagcaac accaaggtgg acaagacagt tgagcgcaaa      660
tgttgtgtcg agtgcccacc gtgcccagca ccacctgtgg caggaccgtc agtcttcctc      720 ttcccccca aacccaagga caccctcatg atctcccgga ccctgaggt cacgtgcgtg        780 gtggtggacg tgagccacga agaccccgag gtccagttca actggtacgt ggacggcgtg      840
gaggtgcata atgccaagac aaagccacgg gaggagcagt tcaacagcac gttccgtgtg      900
gtcagcgtcc tcaccgttgt gcaccaggac tggctgaacg gcaaggagta caagtgcaag      960
gtctccaaca aaggcctccc agcccccatc gagaaaacca tctccaaaac caaagggcag     1020
ccccgagaac cacaggtgta caccctgccc ccatcccggg aggagatgac caagaaccag     1080
gtcagcctga cctgcctggt caaaggcttc taccccagcg acatcgccgt ggagtgggag     1140
```

-continued

```
agcaatgggc agccggagaa caactacaag accacacctc ccatgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gt                                                         1332
```

<210> SEQ ID NO 50
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Asp Tyr Ala Gln Lys Phe
    50                  55                  60

Gln Gly Arg Val Thr Met Thr Arg Asp Ile Ser Ile Ser Thr Ala Tyr
65                  70                  75                  80

Ile Glu Leu Ser Ser Leu Arg Ser Glu Asp Thr Ala Val Tyr Tyr Cys
                85                  90                  95

Ala Arg Asp Met Val Ala Asn Thr Asp Tyr Tyr Phe Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320
```

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 51
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Glu Ile Asn Trp Val Arg Gln Ala Thr Gly Gln Gly Leu Glu Trp Met
        35                  40                  45

Gly Trp Met Asn Pro Asn Ser Gly Tyr Thr Gly Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Met Ser Ser Leu Arg Ser Glu Asp Thr Ala Val Tyr Tyr Cys
                85                  90                  95

Ala Arg Asp Ile Val Ala Ala Asn Thr Asp Tyr Tyr Phe Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Gln Phe Asn Trp Tyr Val Asp Gly Val Glu
    275                 280                 285

Val His Asn Ala Lys Thr Lys Pro Arg Glu Glu Gln Phe Asn Ser Thr
290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
            325                 330                 335

Ile Glu Lys Thr Ile Ser Lys Thr Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly
450

<210> SEQ ID NO 52
<211> LENGTH: 444
<212> TYPE: PRT
<213> ORGANISM: Artificial Sequence
<220> FEATURE:
<223> OTHER INFORMATION: Synthetic polypeptide

<400> SEQUENCE: 52

Gln Val His Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Leu Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asn Phe Tyr Tyr Tyr Gly Met Asp Val Trp Gly Gln Gly
            100                 105                 110

Thr Thr Val Thr Val Ser Ser Ala Ser Thr Lys Gly Pro Ser Val Phe
        115                 120                 125

```
Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 53
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45
```

```
Gly Trp Met Asn Pro Asn Ser Gly Asn Thr Asp Tyr Ala Gln Lys Phe
    50                  55                  60

Gln Gly Arg Val Thr Met Thr Arg Asp Ile Ser Ile Ser Thr Ala Tyr
 65             70                  75                  80

Ile Glu Leu Ser Ser Leu Arg Ser Glu Asp Thr Ala Val Tyr Tyr Cys
                85                  90                  95

Ala Arg Asp Met Val Ala Ala Asn Thr Asp Tyr Tyr Phe Tyr Tyr Gly
            100                 105                 110

Met Asp Val Trp Gly Gln Gly Thr Thr Val Thr Val Ser Ser
            115                 120                 125

<210> SEQ ID NO 54
<211> LENGTH: 126
<212> TYPE: PRT
<213> ORGANISM: Artificial Sequence
<220> FEATURE:
<223> OTHER INFORMATION: Synthetic polypeptide

<400> SEQUENCE: 54

Gln Val Gln Leu Val Gln Ser Gly Ala Glu Val Lys Lys Pro Gly Ala
  1              5                  10                  15

Ser Val Lys Val Ser Cys Lys Ala Ser Gly Tyr Thr Phe Thr Ser Tyr
             20                  25                  30

Glu Ile Asn Trp Val Arg Gln Ala Thr Gly Gln Gly Leu Glu Trp Met
            35                  40                  45

Gly Trp Met Asn Pro Asn Ser Gly Tyr Thr Gly Tyr Ala Gln Lys Phe
    50                  55                  60

Gln Gly Arg Val Thr Met Thr Arg Asp Thr Ser Ile Ser Thr Ala Tyr
 65             70                  75                  80

Met Glu Met Ser Ser Leu Arg Ser Glu Asp Thr Ala Val Tyr Tyr Cys
                85                  90                  95

Ala Arg Asp Ile Val Ala Ala Asn Thr Asp Tyr Tyr Phe Tyr Tyr Gly
            100                 105                 110

Met Asp Val Trp Gly Gln Gly Thr Thr Val Thr Val Ser Ser
            115                 120                 125
```

ONCOSTATIN M RECEPTOR ANTIGEN BINDING PROTEINS

CROSS-REFERENCE TO RELATED APPLICATIONS

This application is a division of U.S. patent application Ser. No. 15/486,094, which is a division of U.S. patent application Ser. No. 14/891,491, which is the U.S. National Stage Entry under 35 U.S.C. § 371 of International Application No. PCT/US2014/040360, which claims the benefit of priority to U.S. Provisional Appl. No. 61/829,082, filed May 30, 2013, the content of each of which is incorporated by reference in its entirety herein.

This application contains a sequence listing created on Jul. 11, 2017 and named SL_KPL-001US4.txt. The sequence listing is 108,900 bytes in size and its contents are hereby incorporated by reference.

BACKGROUND OF THE INVENTION

Oncostatin M (OSM) and Interleukin-31 (IL-31) are members of the IL-6 superfamily and share a receptor subunit, oncostatin M receptor-β (OSMR) (Dillon et al., Nat. Immunol. 5(7): 752-60, 2004). All of the members of this family, except IL-31, share the common chain of glycoprotein 130 (gp130) in their multimeric receptor complexes. OSM signals through a heterodimeric receptor complex containing OSMR and gp130, while IL-31 utilizes a gp130-like receptor, IL-31R, in combination with OSMR (Dillon et al., supra; Dreuw et al., J. Biol. Chem. 279(34): 36112-20, 2004). In general, OSMR and gp130 are expressed fairly ubiquitously across tissues and cell types, and can be induced under a variety of stimulation conditions. IL-31R expression appears to be relatively more restricted and tightly regulated. In human and mice alike, IL-31R mRNA expression is detectable at low levels in tissues such as trachea, skeletal muscle, thymus and bone marrow (Dillon et al., supra). Although the level of expression is starkly different, both IL-31R and OSMR are co-expressed on a multitude of tissues, including skin and intestinal epithelial cells, suggesting those tissues should respond to IL-31 (Dillon et al., supra; Dambacher et al., Gut 56(9): 1257-65, 2007). While OSMR is expressed constitutively in the lung on epithelial cells, IL-31R expression is at negligible to low levels in the lung tissue, but upregulated upon various methods of airway challenge (Dillon et al., supra; Jawa et al., J. Interferon Cytokine Res. 28(4): 207-19, 2008).

Secreted primarily by T lymphocytes, macrophages, and neutrophils, OSM and IL-31 are both upregulated in a variety of disease states that involve inflammation. OSM has been implicated in diverse biological roles including bone formation, cartilage degradation, cholesterol uptake, pain and inflammation (Cawston et al., Arthritis Rheum. 41(10): 1760-71, 1998; Hasegawa et al., Rheumatology (Oxford) 38(7): 612-7, 1999; Levy et al., J. Hepatol. 32(2): 218-26, 2000; Manicourt et al., Arthritis. Rheum. 43(2): 281-8, 2000; de Hooge et al., Am J. Pathol. 160(5): 1733-43, 2002; Luzina et al., Arthritis Rheum 48(8): 2262-74, 2003; Morikawa et al., J. Neurosci. 24(8): 1941-7, 2004; Kong et al., J. Lipid Res. 46(6): 1163-71, 2005). OSM has been demonstrated to be a potent modulator of extracellular matrix (ECM) in a variety of contexts, suggesting that OSM is able to mediate seemingly opposite pathological consequences, including fibrosis (an excess of ECM) and cartilage degradation (a breakdown of ECM). Depending on tissue type and environmental milieu, both of these effects have been observed when OSM has been overexpressed or exogenously administered into lungs or joints of mice, respectively (Richards et al., Biochem. Soc. Trans. 30(2): 107-11, 2002; Hui et al., Arthritis Rheum. 48(12): 3404-18, 2003; Rowan et al., Am. J. Pathol. 162(6): 1975-84, 2003). In addition, OSM has previously been shown to be upregulated in human pathologies where these types of consequences exist (Cawston et al., supra; Hasegawa et al., supra; Levy et al., supra; Manicourt et al., supra; Luzina et al., supra). Predominantly, a locally-acting cytokine, OSM is upregulated in the synovial fluid from joints of patients with rheumatoid arthritis (RA) (Cawston et al., supra; Manicourt et al., supra), in the broncheoalevolar lavage (BAL) fluid of patients with scleroderma-associated interstitial lung disease (Luzina et al., supra), idiopathic pulmonary fibrosis (IPF), and in the livers of patients with cirrhosis (Levy et al., supra). The proposed impact on ECM by OSM can be attributed in part to the ability of OSM to shift the balance between matrix metalloproteinases (MMPs) and tissue inhibitors of MMPs (TIMPs). TIMPs bind to MMPs in a 1:1 ratio with a high affinity that results in a loss of MMP proteolytic activity. TIMP-1 and TIMP-3 have been previously shown to be differentially regulated by OSM, resulting in an increase in TIMP-1 and a decrease in TIMP-3 (Gatsios et al., Eur. J. Biochem. 241(1): 56-63, 1996). In addition to regulating the digestion of extracellular matrix components, MMPs are also implicated in the cleaving and subsequent activation of a number of proteins, including TGF-β, a potent pro-fibrotic cytokine (Leask et al., FASEB J. 18(7): 816-27, 2004). OSM has also been reported to be capable of directly inducing the transcription of type I collagen in vitro (Hasegawa et al., J. Rheumatol. 25(2): 308-13, 1998).

Expression of both OSM and IL-31 has been found in the skin of patients with psoriasis and atopic dermatitis, and mutations in OSMR and IL-31R have been linked to systemic cutaneous amyloidosis. System-wide transgenic overexpression of IL-31 induced a pruritic inflammatory response in the skin of mice. Both OSM and IL-31 both signal through OSMR on neurons where they have been suggested to promote nociceptive and pruritic responses.

Collectively, these links to human diseases and the ability of OSM and IL-31 to promote a diverse array of pathologies, including at least inflammation, extracellular matrix remodeling, pain, and pruritis, suggest blockade of OSMR is a useful target for therapeutic intervention in many diseases and disorders associated with OSMR.

SUMMARY OF THE INVENTION

The invention provides anti-OSMR antigen binding proteins, e.g., antibodies and functional fragments thereof, having properties amenable to commercial production and therapeutic use in humans. The anti-OSMR antigen binding proteins are useful in methods of treating diseases and disorders associated with OSMR and, particularly, those associated with the binding of OSM or IL-31 to OSMR. Provided herein are OSMR-binding antibodies that bind OSMR with high affinity and effectively block OSM and/or IL-31 binding to OSMR, thereby reducing OSMR-mediated signaling in the cell.

In a first aspect, the OSMR antigen binding protein comprises a) a light chain variable domain having at least 90% identity, at least 95% identity, or is identical to the amino acid sequence set forth in SEQ ID NO:27, SEQ ID NO:28, or SEQ ID NO:29; b) a heavy chain variable domain having at least 90% identity, at least 95% identity, or is identical to the amino acid sequence set forth in SEQ ID NO:9, SEQ ID NO:10, or SEQ ID NO:11; or c) the light chain variable domain of a) and the heavy chain variable domain of b).

Preferred antigen binding proteins of the first aspect include those comprising a light chain variable domain having at least 90%, at least 95%, or is identical to the amino acid sequence set forth in SEQ ID NO:27 and a heavy chain variable domain having at least 90%, at least 95%, or is identical to the amino acid sequence set forth in SEQ ID NO:9; those comprising a light chain variable domain having at least 90%, at least 95%, or is identical to the amino acid sequence set forth in SEQ ID NO:28 and a heavy chain variable domain having at least 90%, at least 95%, or is identical to the amino acid sequence set forth in SEQ ID NO:10; and those comprising a light chain variable domain having at least 90%, at least 95%, or is identical to the amino acid sequence set forth in SEQ ID NO:29 and a heavy chain variable domain having at least 90%, at least 95%, or is identical to the amino acid sequence set forth in SEQ ID NO:11.

OSMR antigen binding proteins comprising a heavy chain variable domain having the above-defined sequence relatedness to SEQ ID NO:9 can optionally contain an amino acid other than asparagine (for example, aspartic acid) at the position corresponding to position 73 in SEQ ID NO:9. In such embodiments, the heavy chain variable domain optionally comprises the amino acid sequence set forth in SEQ ID NO:53.

OSMR antigen binding proteins comprising a heavy chain variable domain having the above-defined sequence relatedness to SEQ ID NO: 10 can optionally contain an amino acid other than asparagine (for example, aspartic acid) at the position corresponding to position 73 in SEQ ID NO: 10. In such embodiments, the heavy chain variable domain optionally comprises the amino acid sequence set forth in SEQ ID NO:54.

In a second aspect, the OSMR antigen binding protein comprises a) a light chain variable domain having no more than ten or no more than five amino acid additions, deletions or substitutions from the amino acid sequence set forth in SEQ ID NO:27, SEQ ID NO:28, or SEQ ID NO:29; b) a heavy chain variable domain having no more than ten or no more than five amino acid additions, deletions or substitutions from the amino acid sequence set forth in SEQ ID NO:9, SEQ ID NO:10, or SEQ ID NO:11; or c) the light chain variable domain of a) and the heavy chain variable domain of b).

Preferred antigen binding proteins of the second aspect include those comprising a light chain variable domain having no more than ten or no more than five amino acid additions, deletions or substitutions from the amino acid sequence set forth in SEQ ID NO:27 and a heavy chain variable domain having no more than ten or no more than five amino acid additions, deletions or substitutions from the amino acid sequence set forth in SEQ ID NO:9; those comprising a light chain variable domain having no more than ten or no more than five amino acid additions, deletions or substitutions from the amino acid sequence set forth in SEQ ID NO:28 and a heavy chain variable domain having no more than ten or no more than five amino acid additions, deletions or substitutions from the amino acid sequence set forth in SEQ ID NO: 10; and those comprising a light chain variable domain having no more than ten or no more than five amino acid additions, deletions or substitutions from the amino acid sequence set forth in SEQ ID NO:29 and a heavy chain variable domain having no more than ten or no more than five amino acid additions, deletions or substitutions from the amino acid sequence set forth in SEQ ID NO:11.

OSMR antigen binding proteins comprising a heavy chain variable domain having the above-defined sequence relatedness to SEQ ID NO:9 can optionally contain an amino acid other than asparagine (for example, aspartic acid) at the position corresponding to position 73 in SEQ ID NO:9. In such embodiments, the heavy chain variable domain optionally comprises the amino acid sequence set forth in SEQ ID NO:53.

OSMR antigen binding proteins comprising a heavy chain variable domain having the above-defined sequence relatedness to SEQ ID NO: 10 can optionally contain an amino acid other than asparagine (for example, aspartic acid) at the position corresponding to position 73 in SEQ ID NO: 10. In such embodiments, the heavy chain variable domain optionally comprises the amino acid sequence set forth in SEQ ID NO:54.

In a third aspect, the OSMR antigen binding protein contains a light chain variable domain comprising a) an LCDR1 having no more than three amino acid additions, deletions, or substitutions from the LCDR1 sequence set forth in SEQ ID NO:30; an LCDR2 having no more than three amino acid additions, deletions, or substitutions from the LCDR2 sequence set forth in SEQ ID NO:33; and an LCDR3 having no more than three amino acid additions, deletions, or substitutions from the LCDR3 sequence set forth in SEQ ID NO:36; b) an LCDR1 having no more than three amino acid additions, deletions, or substitutions from the LCDR1 sequence set forth in SEQ ID NO:31; an LCDR2 having no more than three amino acid additions, deletions, or substitutions from the LCDR2 sequence set forth in SEQ ID NO:34; and an LCDR3 having no more than three amino acid additions, deletions, or substitutions from the LCDR3 sequence set forth in SEQ ID NO:37; or c) an LCDR1 having no more than three amino acid additions, deletions, or substitutions from the LCDR1 sequence set forth in SEQ ID NO:32; an LCDR2 having no more than three amino acid additions, deletions, or substitutions from the LCDR2 sequence set forth in SEQ ID NO:35; and an LCDR3 having no more than three amino acid additions, deletions, or substitutions from the LCDR3 sequence set forth in SEQ ID NO:38; and a heavy chain variable domain comprising d) an HCDR1 having no more than three amino acid additions, deletions, or substitutions from the HCDR1 sequence set forth in SEQ ID NO: 12; an HCDR2 having no more than three amino acid additions, deletions, or substitutions from the HCDR2 sequence set forth in SEQ ID NO:15; and an HCDR3 having no more than three amino acid additions, deletions, or substitutions from the HCDR3 sequence set forth in SEQ ID NO:18; e) an HCDR1 having no more than three amino acid additions, deletions, or substitutions from the HCDR1 sequence set forth in SEQ ID NO:13; an HCDR2 having no more than three amino acid additions, deletions, or substitutions from the HCDR2 sequence set forth in SEQ ID NO:16; and an HCDR3 having no more than three amino acid additions, deletions, or substitutions from the HCDR3 sequence set forth in SEQ ID NO: 19; or f) an HCDR1 having no more than three amino acid additions, deletions, or substitutions from the HCDR1 sequence set forth in SEQ ID NO:14; an HCDR2 having no more than three amino acid additions, deletions, or substitutions from the HCDR2 sequence set forth in SEQ ID NO:17; and an HCDR3 having no more than three amino acid additions, deletions, or substitutions from the HCDR3 sequence set forth in SEQ ID NO:20.

Preferred OSMR antigen binding proteins of third aspect include those comprising the light chain variable domain of a) and the heavy chain variable domain of d); those comprising the light chain variable domain of b) and the heavy chain variable domain of e); and those comprising the light chain variable domain of c) and the heavy chain variable domain of f).

OSMR antigen binding proteins comprising the light chain variable domain of a) and the heavy chain variable domain of d) can optionally contain a heavy chain variable domain that comprises an amino acid other than asparagine (for example, aspartic acid) at the position corresponding to position 73 in SEQ ID NO:9. In such embodiments, the heavy chain variable domain optionally comprises the amino acid sequence set forth in SEQ ID NO:53.

OSMR antigen binding proteins comprising the light chain variable domain of b) and the heavy chain variable domain of e) can optionally contain a heavy chain variable domain that comprises an amino acid other than asparagine (for example, aspartic acid) at the position corresponding to position 73 in SEQ ID NO: 10. In such embodiments, the heavy chain variable domain optionally comprises the amino acid sequence set forth in SEQ ID NO:54.

In a fourth aspect of the invention, the OSMR antigen binding protein of the first, second, or third aspect binds to human OSMR with an affinity of less than or equal to $1 \times 10^{-10}$ M.

In a fifth aspect of the invention, the OSMR antigen binding protein of the first, second, third, or fourth aspect inhibits binding of human OSM to human OSMR and/or human IL-31 to human OSMR.

In a sixth aspect of the invention, the OSMR antigen binding protein of the first, second, third, fourth, or fifth aspect reduces human OSM-mediated and/or human IL-31-mediated OSMR signaling in human OSMR-expressing cells.

In a seventh aspect of the invention, the OSMR antigen binding protein of the sixth aspect reduces cynomolgus monkey OSM-mediated and/or IL-31-mediated OSMR signaling in cynomolgus monkey OSMR-expressing cells.

In an eighth aspect of the invention, the OSMR antigen binding protein of the first, second, third, fourth, fifth, sixth or seventh aspect is an antibody, such as a human antibody. Preferred antibodies include those antibodies that comprise a light chain having the amino acid sequence set forth in SEQ ID NO:24 and a heavy chain having the amino acid sequence set forth in SEQ ID NO:6; those that comprise a light chain having the amino acid sequence set forth in SEQ ID:25 and a heavy chain having the amino acid sequence set forth in SEQ ID NO:7; and those that comprise a light chain having the amino acid sequence set forth in SEQ ID:26 and a heavy chain having the amino acid sequence set forth in SEQ ID NO:8. Additional antibodies include those antibodies that comprise a light chain having the amino acid sequence set forth in SEQ ID NO:24 and a heavy chain having the amino acid sequence set forth in SEQ ID NO:50; those that comprise a light chain having the amino acid sequence set forth in SEQ ID:25 and a heavy chain having the amino acid sequence set forth in SEQ ID NO:51; and those that comprise a light chain having the amino acid sequence set forth in SEQ ID:26 and a heavy chain having the amino acid sequence set forth in SEQ ID NO:52.

In a ninth aspect, the invention provides nucleic acids or isolated nucleic acids encoding one or more polypeptide components of a OSMR antigen binding protein, e.g., an antibody light chain or antibody heavy chain. In preferred embodiments the nucleic acid encodes a polypeptide comprising:

a) a light chain variable domain having at least 95% identity to the amino acid sequence set forth in SEQ ID NO:27, SEQ ID NO:28, or SEQ ID NO:29;

b) a heavy chain variable domain having at least 95% identity to the amino acid sequence set forth in SEQ ID NO:9, SEQ ID NO:10, or SEQ ID NO:11;

c) a light chain variable domain having no more than five amino acid additions, deletions or substitutions from the amino acid sequence set forth in SEQ ID NO:27, SEQ ID NO:28, or SEQ ID NO:29;

d) a heavy chain variable domain having no more than five amino acid additions, deletions or substitutions from the amino acid sequence set forth in SEQ ID NO:9, SEQ ID NO:10, or SEQ ID NO:11;

e) a light chain variable domain comprising:
  i) an LCDR1 having no more than three amino acid additions, deletions, or substitutions from the LCDR1 sequence set forth in SEQ ID NO:30; an LCDR2 having no more than three amino acid additions, deletions, or substitutions from the LCDR2 sequence set forth in SEQ ID NO:33; and an LCDR3 having no more than three amino acid additions, deletions, or substitutions from the LCDR3 sequence set forth in SEQ ID NO:36;
  ii) an LCDR1 having no more than three amino acid additions, deletions, or substitutions from the LCDR1 sequence set forth in SEQ ID NO:31; an LCDR2 having no more than three amino acid additions, deletions, or substitutions from the LCDR2 sequence set forth in SEQ ID NO:34; and an LCDR3 having no more than three amino acid additions, deletions, or substitutions from the LCDR3 sequence set forth in SEQ ID NO:37; or
  iii) an LCDR1 having no more than three amino acid additions, deletions, or substitutions from the LCDR1 sequence set forth in SEQ ID NO:32; an LCDR2 having no more than three amino acid additions, deletions, or substitutions from the LCDR2 sequence set forth in SEQ ID NO:35; and an LCDR3 having no more than three amino acid additions, deletions, or substitutions from the LCDR3 sequence set forth in SEQ ID NO:38; or f) a heavy chain variable domain comprising:
  i) an HCDR1 having no more than three amino acid additions, deletions, or substitutions from the HCDR1 sequence set forth in SEQ ID NO: 12; an HCDR2 having no more than three amino acid additions, deletions, or substitutions from the HCDR2 sequence set forth in SEQ ID NO:15; and an HCDR3 having no more than three amino acid additions, deletions, or substitutions from the HCDR3 sequence set forth in SEQ ID NO:18;
  ii) an HCDR1 having no more than three amino acid additions, deletions, or substitutions from the HCDR1 sequence set forth in SEQ ID NO:13; an HCDR2 having no more than three amino acid additions, deletions, or substitutions from the HCDR2 sequence set forth in SEQ ID NO:16; and an HCDR3 having no more than three amino acid additions, deletions, or substitutions from the HCDR3 sequence set forth in SEQ ID NO: 19; or
  iii) an HCDR1 having no more than three amino acid additions, deletions, or substitutions from the HCDR1 sequence set forth in SEQ ID NO: 14; an HCDR2 having no more than three amino acid additions, deletions, or substitutions from the HCDR2 sequence set forth in SEQ ID NO: 17; and an HCDR3 having no more than three amino acid additions, deletions, or substitutions from the HCDR3 sequence set forth in SEQ ID NO:20.

In certain embodiments, the nucleic acid or isolated nucleic acid encodes a polypeptide that comprises the amino acid sequence set forth in SEQ ID NO:53 or SEQ ID NO:54.

In certain embodiments, the nucleic acid or isolated nucleic acid encodes a polypeptide that comprises the amino acid sequence set forth in SEQ ID NO:50, SEQ ID NO:51, or SEQ ID NO:52.

In certain embodiments of the ninth aspect, the nucleic acid or isolated nucleic acid encodes an antibody light chain and is at least 80%, at least 90%, at least 95%, or is 100% identical to the nucleotide sequence set forth in SEQ ID NO:21, SEQ ID NO:22, or SEQ ID NO:23. In other embodiments of the ninth aspect, the nucleic acid or isolated nucleic acid encodes an antibody heavy chain and is at least 80%, at least 90%, at least 95%, or is 100% identical to the nucleotide sequence set forth in SEQ ID NO:3, SEQ ID NO:4, or SEQ ID NO:5.

In certain embodiments, the heavy chain is encoded by a nucleic acid comprising a nucleotide sequence set forth in SEQ ID NO:47, SEQ ID NO:48, or SEQ ID NO:49.

In a tenth aspect, the invention provides an expression vector comprising one or more nucleic acids or isolated nucleic acids of the eighth aspect. In certain embodiments, the expression vector encodes an antibody light chain, an antibody heavy chain, or both an antibody light chain and a heavy chain.

In an eleventh aspect, the invention provides a recombinant host cell comprising one or more nucleic acids or isolated nucleic acids of the ninth aspect operably linked to a promoter, including recombinant host cells comprising one or more expression vectors of the tenth aspect of the invention. In preferred embodiments, the recombinant host cell secretes an antibody that binds OSMR. Preferred host cells are mammalian host cells, including CHO cell lines.

In a twelfth aspect, the invention provides methods of treating an autoimmune disorder, an inflammatory disorder, or a disorder associated with extracellular matrix deposition or remodeling, said method comprising administering a therapeutically effective amount of an OSMR antigen binding protein of any one of the first, second, third, fourth, fifth, sixth, sixth, seventh, or eighth aspects to a patient in need thereof. In preferred embodiments, the OSMR antigen binding protein is an antibody comprising a light chain variable domain amino acid sequence as set forth in SEQ ID NO:27 and a heavy chain variable domain amino acid sequence as set forth in SEQ ID NO:9 (e.g., Ab1), an antibody comprising a light chain variable domain amino acid sequence as set forth in SEQ ID NO:28 and a heavy chain variable domain amino acid sequence as set forth in SEQ ID NO: 10 (e.g., Ab2), or an antibody comprising a light chain variable domain amino acid sequence as set forth in SEQ ID NO:29 and a heavy chain variable domain amino acid sequence as set forth in SEQ ID NO:11 (e.g., Ab3). In some embodiments, the OSMR antigen binding protein is an antibody comprising a light chain variable domain amino acid sequence as set forth in SEQ ID NO:27 and a heavy chain variable domain amino acid sequence as set forth in SEQ ID NO:53, or an antibody comprising a light chain variable domain amino acid sequence as set forth in SEQ ID NO:28 and a heavy chain variable domain amino acid sequence as set forth in SEQ ID NO:54. In preferred embodiments, the OSMR antigen binding protein inhibits binding of OSM to OSMR or IL-31 to OSMR. In particularly preferred embodiments, the autoimmune disorder, inflammatory disorder, or disorder associated with extracellular matrix deposition or remodeling is fibrosis, cartilage degradation, arthritis, rheumatoid arthritis, scleroderma, scleroderma-associated interstitial lung disease, idiopathic pulmonary fibrosis, cirrhosis, psoriasis, atopic dermatitis, systemic cutaneous amyloidosis, primary cutaneous amyloidosis, inflammation, pruritic inflammation, prurigo nodularis, and pain.

In a thirteenth aspect, the invention provides a method of making an OSMR antigen binding protein of any one of the first, second, third, fourth, fifth, sixth, sixth, seventh, or eighth aspects by culturing a recombinant host cell of the eleventh aspect and isolating the OSMR antigen binding protein from said culture.

In a fourteenth aspect, the invention provides OSMR antigen binding proteins of any one of the first, second, third, fourth, fifth, sixth, sixth, seventh, or eighth aspects that cross-compete with an antibody selected from the group consisting of:

a) an antibody comprising a light chain comprising the amino acid sequence set forth in SEQ ID:24 and a heavy chain comprising the amino acid sequence set forth in SEQ ID NO:6;

b) an antibody comprising a light chain comprising the amino acid sequence set forth in SEQ ID:25 and a heavy chain comprising the amino acid sequence set forth in SEQ ID NO:7; and c) an antibody comprising a light chain comprising the amino acid sequence set forth in SEQ ID:26 and a heavy chain comprising the amino acid sequence set forth in SEQ ID NO:8.

DETAILED DESCRIPTION

The section headings used herein are for organizational purposes only and are not to be construed as limiting the subject matter described. All references cited within the body of this specification are expressly incorporated by reference in their entirety.

Standard techniques may be used for recombinant DNA, oligonucleotide synthesis, tissue culture and transformation, protein purification, etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manuel*, 3$^{rd}$ ed., Cold Spring Harbor Laboratory Press, cold Spring Harbor, N.Y., which is incorporated herein by reference for any purpose. Unless specific definitions are provided, the nomenclature used in connection with, and the laboratory procedures and techniques of, analytic chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

OSMR

The antigen binding proteins described herein bind to OSMR. OSM and IL-31 signal through OSMR. OSMR is a member of the type I cytokine receptor family. OSMR heterodimerizes with glycoprotein 130 (also known as gp130, interleukin 6 signal transducer (IL6ST), IL6-beta, or CD130) to form the type II OSMR. OSMR also heterodimerizes with IL-31 receptor A (IL31RA) to form the IL-31 receptor and, thus, transduces OSM- and IL-31-induced signaling events. In exemplary embodiments, an OSMR antigen binding protein binds OSMR and prevents OSM- and/or IL-31-mediated signaling in cells expressing OSMR.

Human OSMR sequences are known in the art. In various aspects, human OSMR protein sequences are provided in GenBank Accession Nos. AAI25210, AAI25211, NP_003990, and EAW55976. An exemplary human OSMR amino acid sequence (SEQ ID NO: 1) is provided in Table 1. The protein is made up of several domains: Amino acids 1-27 correspond to the signal sequence which may be cleaved during processing of the protein in mammalian cells; amino acids 28-740 correspond to the extracellular domain; and amino acids 741-761 correspond to the transmembrane domain. In preferred embodiments, the antigen binding proteins described herein bind to the extracellular domain of OSMR and prevent the interaction of OSM and/or IL-31 with OSMR.

Human OSM sequences are known in the art. In various aspects, human OSM protein sequences are provided in GenBank Accession Nos. CAG30420, CAG46504, NP_065391, P13725, AAC05173, EAW59864, and AAH11589. An exemplary human OSM amino acid sequence (SEQ ID NO: 39) is provided in Table 1. Amino acids 1-25 correspond to the signal sequence; amino acids 26-220 correspond to the mature protein; and amino acids 221-252 correspond to the propeptide sequence.

Human IL-31 sequences are known in the art. In various aspects, human IL-31 protein sequences are provided in GenBank Accession Nos. NP_001014358, AAS86448, AAI32999, AAI33001, Q6EBC2, and EAW98310. An exemplary human IL-31 amino acid sequence (SEQ ID NO: 41) is provided in Table 1. Amino acids 1-23 correspond to the putative signal sequence.

Human IL31RA sequences are known in the art. In various aspects, human IL31RA protein sequences are provided in GenBank Accession Nos. AAS86447, NP_001229567, and CBL94051. An exemplary human IL31RA (v4, isoform 3) amino acid sequence (SEQ ID NO: 43) is provided in Table 1. Amino acids 1-32 correspond to the signal sequence; and amino acids 533-553 correspond to the transmembrane sequence.

Human gp130 sequences are known in the art. In various aspects, human gp130 protein sequences are provided in GenBank Accession Nos. AAI17403, AAI17405, EAW54936, NP_002175, ABK41905, and AAA59155. An exemplary human gp130 amino acid sequence (SEQ ID NO: 45) is provided in Table 1. The protein is made up of several domains: Amino acids 1-22 correspond to the signal sequence; amino acids 23-619 correspond to the extracellular domain; amino acids 620-641 correspond to the transmembrane domain; and amino acids 642-918 correspond to the cytoplasmic domain.

TABLE 1

Human OSMR amino acid sequence (SEQ ID NO: 1)
MALFAVFQTTFFLTLLSLRTYQSEVLAERLPLTPVSLKVSTNSTRQSLHL
QWTVHNLPYHQELKMVFQIQISRIETSNVIWVGNYSTTVKWNQVLHWSWE
SELPLECATHFVRIKSLVDDAKFPEPNFWSNWSSWEEVSVQDSTGQDILF
VFPKDKLVEEGTNVTICYVSRNIQNNVSCYLEGKQIHGEQLDPHVTAFNL
NSVPFIRNKGTNIYCEASQGNVSEGMKGIVLFVSKVLEEPKDFSCETEDF
KTLHCTWDPGTDTALGWSKQPSQSYTLFESFSGEKKLCTHKNWCNWQITQ TABLE 1-continued DSQETYNFTLIAENYLRKRSVNILFNLTHRVYLMNPFSVNFENVNATNAI
MTWKVHSIRNNFTYLCQIELHGEGKMMQYNVSIKVNGEYPLSELEPATEY
MARVRCADASHFWKWSEWSGQNFTTLEAAPSEAPDVWRIVSLEPGNHTVT
LFWKPLSKLHANGKILFYNVVVENLDKPSSSELHSIPAPANSTKLILDRC
SYQICVIANNSVGASPASVIVISADPENKEVEEERIAGTEGGFSLSWKPQ
PGDVIGYVVDWCDHTQDVLGDFQWKNVGPNTTSTVISTDAFRPGVRYDFR
IYGLSTKRIACLLEKKTGYSQELAPSDNPHVLVDTLTSHSFTLSWKDYST
ESQPGFIQGYHVYLKSKARQCHPRFEKAVLSDGSECCKYKIDNPEEKALI
VDNLKPESFYEFFITPFTSAGEGPSATFTKVTTPDEHSSMLIHILLPMVF
CVLLIMVMCYLKSQWIKETCYPDIPDPYKSSILSLIKFKENPHLIIMNVS
DCIPDAIEVVSKPEGTKIQFLGTRKSLTETELTKPNYLYLLPTEKNHSGP
GPCICFENLTYNQAASDSGSCGHVPVSPKAPSMLGLMTSPENVLKALEKN
YMNSLGEIPAGETSLNYVSQLASPMFGDKDSLPTNPVEAPHCSEYKMQMA
VSLRLALPPPTENSSLSSITLLDPGEHYC Human OSM amino acid sequence (SEQ ID NO: 39)
MGVLLTQRTLLSLVLALLFPSMASMAAIGSCSKEYRVLLGQLQKQTDLMQ
DTSRLLDPYIRIQGLDVPKLREHCRERPGAFPSEETLRGLGRRGFLQTLN
ATLGCVLHRLADLEQRLPKAQDLERSGLNIEDLEKLQMARPNILGLRNNI
YCMAQLLDNSDTAEPTKAGRGASQPPTPTPASDAFQRKLEGCRFLHGYHR
FMHSVGRVFSKWGESPNRSRRHSPHQALRKGVRRTRPSRKGKRLMTRGQL
PR Human IL-31 amino acid sequence (SEQ ID NO: 41)
MASHSGPSTSVLFLFCCLGGWLASHTLPVRLLRPSDDVQKIVEELQSLSK
MLLKDVEEEKGVLVSQNYTLPCLSPDAQPPNNIHSPAIRAYLKTIRQLDN
KSVIDEIIEHLDKLIFQDAPETNISVPTDTHECKRFILTISQQFSECMDL
ALKSLTSGAQQATT Human IL31RA amino acid sequence (SEQ ID NO: 43)
MKLSPQPSCVNLGMMWTWALWMLPSLCKFSLAALPAKPENISCVYYYRKN
LTCTWSPGKETSYTQYTVKRTYAFGEKHDNCTTNSSTSENRASCSFFLPR
ITIPDNYTIEVEAENGDGVIKSHMTYWRLENIAKTEPPKIFRVKPVLGLR
RMIQIEWIKPELAPVSSDLKYTLRFRTVNSTSWMEVNFAKNRKDKNQTYN
LTGLQPFTEYVIALRCAVKESKFWSDWSQEKMGMTEEEAPCGLELWRVLK
PAEADGRRPVRLLWKKARGAPVLEKTLGYNIWYYPESNTNLTETMNTTNQ
QLELHLGGESFWVSMISYNSLGKSPVATLRIPAIQEKSFQCIEVMQACVA
EDQLVVKWQSSALDVNTWMIEWFPDVDSEPTTLSWESVSQATNWTIQQDK
LKPFWCYNISVYPMLHDKVGEPYSIQAYAKEGVPSEGPETKVENIGVKTV
TITWKEIPKSERKGIICNYTIFYQAEGGKGFSKTVNSSILQYGLESLKRK
TSYIVQVMASTSAGGTNGTSINFKTLSFSVFEIILITSLIGGGLLILIIL
TVAYGLKKPNKLTHLCWPTVPNPAESSIATWHGDDFKDKLNLKESDDSVN
TEDRILKPCSTPSDKLVIDKLVVNFGNVLQEIFTDEARTGQENNLGGEKN
GTRILSSCPTSI Human gp130 amino acid sequence (SEQ ID NO: 45)
MLTLQTWLVQALFIFLTTESTGELLDPCGYISPESPVVQLHSNFTAVCVL
KEKCMDYFHVNANYIVWKTNHFTIPKEQYTIINRTASSVTFTDIASLNIQ
LTCNILTFGQLEQNVYGITIISGLPPEKPKNLSCIVNEGKKMRCEWDGGR
ETHLETNFTLKSEWATHKFADCKAKRDTPTSCTVDYSTVYFVNIEVWVEA
ENALGKVTSDHINFDPVYKVKPNPPHNLSVINSEELSSILKLTWTNPSIK
SVIILKYNIQYRTKDASTWSQIPPEDTASTRSSFTVQDLKPFTEYVFRIR
CMKEDGKGYWSDWSEEASGITYEDRPSKAPSFWYKIDPSHTQGYRTVQLV
WKTLPPFEANGKILDYEVTLTRWKSHLQNYTVNATKLTVNLTNDRYLATL
TVRNLVGKSDAAVLTIPACDFQATHPVMDLKAFPKDNMLWVEWTTPRESV
KKYILEWCVLSDKAPCITDWQQEDGTVHRTYLRGNLAESKCYLITVTPVY
ADGPGSPESIKAYLKQAPPSKGPTVRTKKVGKNEAVLEWDQLPVDVQNGF
IRNYTIFYRTIIGNETAVNVDSSHTEYTLSSLTSDTLYMVRMAAYTDEGG
KDGPEFTFTTPKFAQGEIEAIVVPVCLAFLLTTLLGVLFCFNKRDLIKKH
IWPNVPDPSKSHIAQWSPHTPPRHNFNSKDQMYSDSNFTDVSVVEIVAND
KKPFPEDLKSLDLFKKEKINTEGHSSGIGGSSCMSSSRPSISSSDENESS
QNTSSTVQYSTVVHSGYRHQVPSVQVFSRSESTQPLLDSEERPEDLQLVD
HVDGGDGILPRQQYFKQNCSQHESSPDISHFERSKQVSSVNEEDFVRLKQ
QISDHISQSCGSGQMKMFQEVSAADAFGPGTEGQVERFETVGMEAATDEG
MPKSYLPQTVRQGGYMPQ In particular embodiments of the present invention, antigen binding proteins described herein bind both human and cynomolgus monkey OSMR with high affinity, including those that bind with high affinity and block interaction of cynomolgus monkey OSM and/or IL-31 to cynomolgus monkey OSMR. These characteristics allow informative toxicology studies in non-human primates.

A Rhesus macaque (*Macaca mulatta*) OSMR protein sequence is known in the art and is provided in GenBank Accession No. XP_001083745. An exemplary cynomolgus monkey (*Macaca fascicularis*) OSMR amino acid sequence (SEQ ID NO:2) is provided in Table 2. The protein is made up of several domains: Amino acids 1-27 correspond to the signal sequence which may be cleaved during processing of the protein in mammalian cells; amino acids 28-737 correspond to the extracellular domain; and amino acids 738-757 correspond to the transmembrane domain. In preferred embodiments, the antigen binding proteins described herein bind to the extracellular domain of OSMR and prevent the interaction of OSM and/or IL-31 with OSMR.

A Rhesus macaque (*Macaca mulatta*) OSM protein sequence is known in the art and is provided in GenBank Accession No. NP_001181403. An exemplary cynomolgus monkey (*Macaca fascicularis*) OSM amino acid sequence (SEQ ID NO:40) is provided in Table 2. Amino acids 1-196 correspond to the mature cynomolgus OSM.

A Rhesus macaque (*Macaca mulatta*) IL-31 protein sequence is known in the art and is provided in GenBank Accession No. XP_001096743. An exemplary cynomolgus monkey (*Macaca fascicularis*) IL-31 amino acid sequence (SEQ ID NO:42) is provided in Table 2. This sequence represents the mature cynomolgus monkey IL-31.

An exemplary cynomolgus monkey (*Macaca fascicularis*) IL31RA amino acid sequence (SEQ ID NO: 44) is provided in Table 2. Amino acids 1-19 correspond to the signal sequence; and amino acids 520-540 correspond to the transmembrane domain.

A Rhesus macaque (*Macaca mulatta*) gp130 protein sequence is known in the art and is provided in GenBank Accession No. NP_001252920. An exemplary cynomolgus monkey (*Macaca fascicularis*) gp130 amino acid sequence (SEQ ID NO: 46) is provided in Table 2. The protein is made up of several domains: Amino acids 1-22 correspond to the signal sequence; amino acids 23-619 correspond to the extracellular domain; amino acids 620-641 correspond to the transmembrane domain; and amino acids 642-918 correspond to the cytoplasmic domain.

TABLE 2

```
Cynomolgus monkey OSMR amino acid sequence
(SEQ ID NO: 2)
MALFVVFQTTFFLILLSLRTYQSEVLAERLPLTPVSLKVSTNSIHQSLHL
QWTVHNLPYHQELKMVFQIQISRIETSNVVWVGNYSTPVKWNQVLHWSWE
SELPLECATHFVRIKSVIDDASFPEPNFWSNWSSWEEVSVQDYLGRGTLF
VFPKDKLVEEGSNVTICYVSRNIQNNVSCYLEGKQIHGEQLDPHVTAFNL
NSVPFIRNRGTNIYCEASQGNVSKGIEGIVLFVSKVLEEPKDFSCESQDF
KTLHCTWDPGTDTALGWSKQPSQSYTLFESFSGEKKLCTHKNWCNWQITQ
DSQEMYNFTLIAENYLRKRSVNILFNLTHRVYLMNPFSVNFENVNATNAI
MTWKVHSMRNNFTYLCQIELHGEGKMMQYDVSINVNGEYFLSELEPATEY
MARVRCADASHFWKWTEWSGQNFTTLEAAPSEAPDVWRSVNSEPGNHTVT
LFWKPLSKLHANGKILFYNVVVENLDKPSRSELRSIPAPANSTKLILDRC
SYQICVTANNSVGASPASIIVISADPENKEVEEERIAGTEGGFSLSWKPQ
PGDVIGYVVDWCDHPQDVLQWKNVGPNTTSTVISTDAFRPGVRYDPRIYG
LSTKRIACLLEKKTGYSQELAPSDNPHYLVDMLTSHSFTLSWKDYSTESQ
PGFIQGYHVYLKSKARQCHPRFQKAVLSDGSECCRYKIDNPEEKALIVDN
LKPESFYEFFVTPFTSAGEGPNATFTKVTTPDEHSSMLIRILLPMVFCVL
LIMIVCYLKSQWIKETCYPDIPDPYKSSILSLIKFKENPHLTIMNVSDCI
PDAIEVVSKPEGTKIQLLGTRKSLTETELTKPNYLYLLPTEKNHSGPGPC
ICFENFTYNQAASDAGSCGHVPVPPKAPPSMLGLMTSPENVLKALEKNYM
NSLGEVPAGETSLNYVSQLASPMSGDKDSLPTNPVEPPHCSEYKMQMAVP
LRLALPPPTENSSLSSITLLDPGEHYR Cynomolgus monkey OSM amino acid sequence
(SEQ ID NO: 40)
AAMGSCSKEYRMLLGQLQKQTDLMQDTSRLLDPYIRIQGLDIPKLREHCR
ESPGAFPSEETLRGLGRRGFLQTLNATLGRILHRLADLEQHLPKAQDLER
SGLNIEDLEKLQMARPNVLGLRNNVYCMAQLLDNSDMTEPTKAGRGTPQP
PTPTPTSDVFQRKLEGCSFLRGYHRFMHSVGRVFSKWGESPNRSRR Cynomolgus monkey IL-31 amino acid sequence
(SEQ ID NO: 42)
TLPVHFLQPSDIQKIVEELQSLSKMLLKDVKEDKGVLVSQNYTLPCLTPD
AQPPPNIIHSPAIRAYLKTIRQLDNKSVIDEIIEHLDKLIFQDAPETNISV
PTDTHECKRFILTISQQFSECMDLALKSLTSGAQQATT
```

TABLE 2-continued

```
Cynomolgus monkey IL31RA amino acid sequence
(SEQ ID NO: 44)
MMWTWALWMFPLLCKFGLAALPAKPENISCVYYYRKNLTCTWSPGKETSY
TQYTAKRTYAFGKKHDNCTTSSSTSENRASCSFFLPRITIPDNYTIEVEA
ENGDGVIKSDMTCWRLEDIAKTEPPEIFSVKPVLGIKRMIRIEWIKPELA
PVSSDLKYALRFRTVNSTSWMEVNFAKNRKDTNQTYNLMGLQAFTEYVVA
LRCAVKESKFWSDWSQEKMGMTEEEAPCGLELWRVLKPTEVDGRRPVRLL
WKKARGAPVLEKTLGYNIWYFPENNTNLTETVNTTNQQLELHLGGESYWV
SMISYNSLGKSPVTTLRIPAIQEKSFRCIEVMQACLAEDQLVVKWQSSAL
DVNTWMIEWFPDMDSEHPTLSWESVSQATNWTIQQDKLKPFWCYNISVYP
MLHDKVGEPYSIQAYAKEGIPSKGPETKVENIGVKTVTITWKEIPKSERK
GIICNYTIFYQAEGGTGFSKTVNSSILQYGLESLKRKTSYTVRVMASTSA
GGINGTSINFKTLSFSVPHILITSLIGGGLLILIILTVAYGLKKPNKLTH
LCWPSVPNPAESSIATWRGDDFKDKLNLKESDDSVNTEDRILKPCSTPSD
KLVIDKSVVNFGNVLQEMFTDEARTGQENNLGGEKNENRILSSCPTSI Cynomolgus monkey gp130 amino acid sequence
(SEQ ID NO: 46)
MLTLQTWVVQALFIFLTTESIGELLDPCGYISPESPVVQLHSNFTAVCVL
KEKCMDYFHVNANYIVWKTNHFTIPKEQYTIINRTASSVTFTDISSLNIQ
LTCNILTFGQLEQNVYGITIISGLPPEKPKNLSCIVNEGKKMRCEWNRGR
ETHLETNFTLKSEWATHKFADCKAKRDTPTSCTVDYSTVYFVNIEVWVEA
ENALGKVTSDHINFDPVYKVKPNPPHNLSVINSEELSSILKLTWTNPSIK
SVIRLKYNIQYRTKDASTWSQIPPEDTASTRSSFTVQDLKPFTEYVFRIC
CMKEDGKGYWSDWSEEANGITYEDRPSKAPSFWYKIDPSHAQGYRTVQLM
WKTLPPFEANGKILDYEVTLTRWKSHLQNYTVNDTKLTVNLTNDRYVATL
TARNLVGKSDAAVLTIPACDFQATHPVMDLKAFPKDNMLWVEWTTPRESV
KKYILEWCVLSDKAPCIADWQQEDGTVHRTHLRGNLAESKCYLITVTPVY
ADGPGSPESIKAYLKQAPPSKGPTVRTKKVGKNEAVLEWDQLPVDVQNGF
IRNYTIFYRTIIGNETAVNVDSSHTEYTLSSLTSDTLYMVRMAAYTDEGG
KDGPEFTFTTPKFAQGEIEAIVVPVCLAFLLTTLLGVLFCFNKRDLIKKH
IWPNVPDPSKSHIAQWSPHTPPRHNFSSKDQMYSDGNFTDVSVVEIEAND
KKPFPEDLKSLDLFKKEKINTEGHSSGIGGSSCMSSSRPSISSSDENESS
QNTSSTVQYSTVVHSGYRHQVPSVQVFSRSESTQPLLDSEERPEDLQLVD
HVDGSDDILPRQQYFKQNCSQHESSPDISHFERSKQVSSVNEEDFVRLKQ
QISDHISQSCGSGEMKMFQEVSAADPFGPGTEGQVERFETIGMEAAIDEG
MPKSYLPQTVRQGGYMPQ
```

OSMR Antigen Binding Proteins

The present invention provides antigen binding proteins that specifically bind OSMR. Embodiments of antigen binding proteins comprise peptides and/or polypeptides that specifically bind OSMR. Such peptides or polypeptides may optionally include one or more port-translational modifications. Embodiments of antigen binding proteins include antibodies and fragments thereof, as variously defined herein, that specifically bind OSMR. These include antibodies that specifically bind human OSMR, including those that inhibit OSM and/or IL-31 from binding and/or activating OSMR.

The antigen binding proteins of the invention specifically bind to OSMR. "Specifically binds" as used herein means that the antigen binding protein preferentially binds OSMR over other proteins. In some embodiments "specifically binds" means the OSMR antigen binding protein has a higher affinity for OSMR than for other proteins. OSMR antigen binding proteins that specifically bind OSMR may have a binding affinity for human OSMR of less than or equal to $1 \times 10^{-7}$ M, less than or equal to $2 \times 10^{-7}$ M, less than or equal to $3 \times 10^{-7}$ M, less than or equal to $4 \times 10^{-7}$ M, less than or equal to $5 \times 10^{-7}$ M, less than or equal to $6 \times 10^{-7}$ M, less than or equal to $7 \times 10^{-7}$ M, less than or equal to $8 \times 10^{-7}$ M, less than or equal to $9 \times 10^{-7}$ M, less than or equal to $1 \times 10^{-8}$ M, less than or equal to $2 \times 10^{-8}$ M, less than or equal to $3 \times 10^{-8}$ M, less than or equal to $4 \times 10^{-8}$ M, less than or equal to $5 \times 10^{-8}$ M, less than or equal to $6 \times 10^{-8}$ M, less than or equal to $7 \times 10^{-8}$ M, less than or equal to $8 \times 10^{-8}$ M, less than or equal to $9 \times 10^{-8}$ M, less than or equal to $1 \times 10^{-9}$ M, less than or equal to $2 \times 10^{-9}$ M, less than or equal to $3 \times 10^{-9}$ M, less than or equal to $4 \times 10^{-9}$ M, less than or equal to $5 \times 10^{-9}$ M, less than or equal to $6 \times 10^{-9}$ M, less than or equal to $7 \times 10^{-9}$ M, less than or equal to $8 \times 10^{-9}$ M, less than or equal to $9 \times 10^{-9}$ M, less than or equal to $1 \times 10^{-10}$ M, less than or equal to $2 \times 10^{-10}$ M, less than or equal to $3 \times 10^{-10}$ M, less than or equal to $4 \times 10^{-10}$ M, less than or equal to $5 \times 10^{-10}$ M, less than or equal to $6 \times 10^{-10}$ M, less than or equal to $7 \times 10^{-10}$ M, less than or equal to $8 \times 10^{-10}$ M, less than or equal to $9 \times 10^{-10}$ M, less than or equal to $1 \times 10^{-11}$ M, less than or equal to $2 \times 10^{-11}$ M, less than or equal to $3 \times 10^{-11}$ M, less than or equal to $4 \times 10^{-11}$ M, less than or equal to $5 \times 10^{-11}$ M, less than or equal to $6 \times 10^{-11}$ M, less than or equal to $7 \times 10^{-11}$ M, less than or equal to $8 \times 10^{-11}$ M, less than or equal to $9 \times 10^{-11}$ M, less than or equal to $1 \times 10^{-12}$ M, less than or equal to $2 \times 10^{-12}$ M, less than or equal to $3 \times 10^{-12}$ M, less than or equal to $4 \times 10^{-12}$ M, less than or equal to $5 \times 10^{-12}$ M, less than or equal to $6 \times 10^{-12}$ M, less than or equal to $7 \times 10^{-12}$ M, less than or equal to $8 \times 10^{-12}$ M, or less than or equal to $9 \times 10^{-12}$ M.

Methods of measuring the binding affinity of an antigen binding protein are well known in the art. Methods in common use for affinity determination include Surface Plasmon Resonance (SPR) (Morton and Myszka "Kinetic analysis of macromolecular interactions using surface plasmon resonance biosensors" *Methods in Enzymology* (1998) 295, 268-294), Bio-Layer Interferometry, (Abdiche et al "Determining Kinetics and Affinities of Protein Interactions Using a Parallel Real-time Label-free Biosensor, the Octet" *Analytical Biochemistry* (2008) 377, 209-217), Kinetic Exclusion Assay (KinExA) (Darling and Brault "Kinetic exclusion assay technology: characterization of molecular interactions" *Assay and Drug Dev Tech* (2004) 2, 647-657), isothermal calorimetry (Pierce et al "Isothermal Titration Calorimetry of Protein-Protein Interactions" *Methods* (1999) 19, 213-221) and analytical ultracentrifugation (Lebowitz et al "Modern analytical ultracentrifugation in protein science: A tutorial review" *Protein Science* (2002), 11:2067-2079). Example 5 provides exemplary methods of affinity determination.

It is understood that when reference is made to the various embodiments of the OSMR-binding antibodies herein, that it also encompasses OSMR-binding fragments thereof. An OSMR-binding fragment comprises any of the antibody fragments or domains described herein that retains the ability to specifically bind to OSMR. The OSMR-binding fragment may be in any of the scaffolds described herein.

In certain therapeutic embodiments, an OSMR antigen binding protein inhibits binding of OSM and/or IL-31 to OSMR and/or inhibits one or more biological activities associated with the binding of OSM and/or IL-31 to OSMR, e.g., OSM- and/or IL-31-mediated signaling. Such antigen binding proteins are said to be "neutralizing." In certain embodiments, the neutralizing OSMR antigen binding protein specifically binds OSMR and inhibits binding of OSM and/or IL-31 to OSMR from anywhere between 10% to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more. For example, OSMR antigen binding proteins may be tested for neutralizing ability by determining the ability of the antigen binding protein to block binding of OSM and/or IL-31 to OSMR, see, e.g., the human OSMR and cynomolgus OSMR blocking assays of Examples 2 and 3, respectively. Alternatively, OSMR antigen binding proteins may be tested for neutralizing ability in an assay that measures the effect of the presence of the OSMR antigen binding protein in an assay measuring OSM- and/or IL-31-mediated biological function. For example, the ability of OSM to induce a biological response, such as stimulation of plasminogen activator activity in cultured bovine aortic endothelial cells, regulation of IL-6 expression in human endothelial cells, and stimulation of LDL uptake and up-regulation of cell surface LDL receptors in HepG2 cells. Alternatively, the ability of IL-31 to induce inflammation in the skin.

Embodiments of antigen binding proteins comprise a scaffold structure, as variously defined herein, with one or more complementarity determining regions (CDRs). Embodiments further include antigen binding proteins comprising a scaffold structure with one or more antibody variable domains, either heavy or light. Embodiments include antibodies that comprise a light chain variable domain selected from the group consisting of Ab1 Light Chain Variable Domain (LCv), Ab2 LCv, and Ab3 LCv (SEQ ID NOS:27-29, respectively) and/or a heavy chain variable domain selected from the group consisting of Ab1 Heavy Chain Variable Domain (HCv), Ab2 HCv, and Ab3 HCv (SEQ ID NOS:9-11, respectively), and fragments, derivatives, muteins, and variants thereof.

An exemplary heavy chain variable domain variant of SEQ ID NO:9 contains an amino acid other than asparagine (for example, aspartic acid) at the position corresponding to position 73 in SEQ ID NO:9. The amino acid sequence set forth in SEQ ID NO:53 is an example of a heavy chain variable domain variant of SEQ ID NO:9.

An exemplary heavy chain variable domain variant of SEQ ID NO: 10 contains an amino acid other than asparagine (for example, aspartic acid) at the position corresponding to position 73 in SEQ ID NO:10. The amino acid sequence set forth in SEQ ID NO:54 is an example of a heavy chain variable domain variant of SEQ ID NO: 10.

An exemplary light chain comprising Ab1 LCv is a light chain comprising the amino acid sequence set forth in SEQ ID NO:24.

An exemplary light chain comprising Ab2 LCv is a light chain comprising the amino acid sequence set forth in SEQ ID NO:25.

An exemplary light chain comprising Ab3 LCv is a light chain comprising the amino acid sequence set forth in SEQ ID NO:26.

An exemplary heavy chain comprising Ab1 HCv is a heavy chain comprising the amino acid sequence set forth in SEQ ID NO:6.

An exemplary heavy chain comprising a variant of Ab1 HCv is a heavy chain comprising the amino acid sequence set forth in SEQ ID NO:50.

An exemplary heavy chain comprising Ab2 HCv is a heavy chain comprising the amino acid sequence set forth in SEQ ID NO:7.

An exemplary heavy chain comprising a variant of Ab2 HCv is a heavy chain comprising the amino acid sequence set forth in SEQ ID NO:51.

An exemplary heavy chain comprising Ab3 HCv is a heavy chain comprising the amino acid sequence set forth in SEQ ID NO:8.

An exemplary heavy chain comprising a variant of Ab3 HCv is a heavy chain comprising the amino acid sequence set forth in SEQ ID NO:52.

Additional examples of scaffolds that are envisioned include, but are not limited to, fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDZ domains, TEM-1 beta-lactamase, thioredoxin, staphylococcal nuclease, PHD-finger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ldl receptor domains, gamma-crystallin, ubiquitin, transferrin, and or C-type lectin-like domains. Non-antibody scaffolds and their use as therapeutics are reviewed in Gebauer and Skerra, *Curr. Opin. Chem. Biol.*, 13:245-255 (2009) and Binz et al., Nat. Biotech., 23(10):1257-68 (2005), which are incorporated herein by reference in its entirety.

Aspects of the invention include antibodies comprising the following variable domains: Ab1 LCv/Ab1 HCv (SEQ ID NO:27/SEQ ID NO:9), Ab2 LCv/Ab2 HCv (SEQ ID NO:28/SEQ ID NO: 10), Ab3 LCv/Ab3 HCv (SEQ ID NO:29/SEQ ID NO: 11), and combinations thereof, as well as fragments, derivatives, muteins and variants thereof.

Also included are antibodies comprising the following variable domains: SEQ ID NO:27/SEQ ID NO:53; and SEQ ID NO:28/SEQ ID NO:54.

Exemplary antibodies of the invention include Ab1 (SEQ ID NO:24/SEQ ID NO:6), Ab2 (SEQ ID NO:25/SEQ ID NO:7), and Ab3 (SEQ ID NO:26/SEQ ID NO:8).

Additional exemplary antibodies include: SEQ ID NO:24/SEQ ID NO:50; SEQ ID NO:25/SEQ ID NO:51; and SEQ ID NO:26/SEQ ID NO:52.

Typically, each variable domain of an antibody light or heavy chain comprises three CDRs. The heavy chain variable domain comprises a heavy chain CDR1 (HCDR1), a heavy chain CDR2 (HCDR2), and a heavy chain CDR3 (HCDR3). The light chain variable domain comprises a light chain CDR1 (LCDR1), a light chain CDR2 (LCDR2), and a light chain CDR3 (LCDR3). In certain embodiments, an antigen binding protein comprises one or more CDRs contained within the preferred variable domains described herein.

Examples of such CDRs include, but are not limited to:
the CDRs of Ab1 LCv: LCDR1 (SEQ ID NO:30), LCDR2 (SEQ ID NO:33), and LCDR3 (SEQ ID NO:36);
the CDRs of Ab2 LCv: LCDR1 (SEQ ID NO:31), LCDR2 (SEQ ID NO:34), and LCDR3 (SEQ ID NO:37);
the CDRs of Ab3 LCv: LCDR1 (SEQ ID NO:32), LCDR2 (SEQ ID NO:35), and LCDR3 (SEQ ID NO:38);
the CDRs of Ab1 HCv: HCDR1 (SEQ ID NO:12), HCDR2 (SEQ ID NO:15), and HCDR3 (SEQ ID NO:18);
the CDRs of Ab2 HCv: HCDR1 (SEQ ID NO:13), HCDR2 (SEQ ID NO:16), and HCDR3 (SEQ ID NO:19); and
the CDRs of Ab3 HCv: HCDR1 (SEQ ID NO:14), HCDR2 (SEQ ID NO:17), and HCDR3 (SEQ ID NO:20).

In some embodiments, the antigen binding protein comprises: A) a polypeptide, e.g., a light chain, that comprises an LCDR1 having an amino acid sequence selected from the group consisting of SEQ ID NOS:30, 31, and 32; an LCDR2 having an amino acid sequence selected from the group consisting of SEQ ID NOS:33, 34, and 35; and/or an LCDR3 having an amino acid sequence selected from the group consisting of SEQ ID NOS:36, 37, and 38; and/or B) a polypeptide, e.g., a heavy chain, that comprises an HCDR1 having an amino acid sequence selected from the group consisting of SEQ ID NOS:12, 13, and 14; an HCDR2 having an amino acid sequence selected from the group consisting of SEQ ID NOS:15, 16, and 17; and/or an HCDR3 having an amino acid sequence selected from the group consisting of SEQ ID NOS:18, 19, and 20.

In further embodiments, the antigen binding protein comprise A) a light chain amino acid sequence that comprises a LCDR1, LCDR2, and LCDR3 of any of Ab1 LCv, Ab2 LCv, and Ab3 LCv and B) a heavy chain amino acid sequence that comprises a HCDR1, HCDR2, and HCDR3 of any of Ab1 HCv, Ab2 HCv, and Ab3 HCv.

In certain embodiments, the CDRs include no more than one, no more than two, no more than three, no more than four, no more than five, or no more than six amino acid additions, deletions, or substitutions from an exemplary CDR set forth herein.

Aspects of the invention include antibodies comprising a light chain variable domain selected from the group consisting of SEQ ID NOS:27, 28, and 29. Aspects of the invention include antibodies comprising a heavy chain variable domain selected from the group consisting of SEQ ID NOS:9, 10, and 11. Further aspects of the invention include antibodies comprising A) a light chain variable domain selected from the group consisting of SEQ ID NOS:27, 28, and 29, and B) a heavy chain variable domain selected from the group consisting of SEQ ID NOS:9, 10, and 11.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant region, e.g., a human alpha-, delta-, epsilon-, gamma-, or mu-type heavy chain constant region. In one embodiment the light or heavy chain constant region is a fragment, derivative, variant, or mutein of a naturally occurring constant region.

Aspects of the invention include antibodies comprising a light chain variable region selected from the group consisting of SEQ ID NOS:27, 28, and 29 having no more than one, no more than two, no more than three, no more than four, no more than five, no more than six, no more than seven, no more than eight, no more than nine, or no more than ten amino acid additions, deletions, or substitutions. Aspects of the invention include antibodies comprising a heavy chain variable region selected from the group consisting of SEQ ID NOS:9, 10, and 11 having no more than one, no more than two, no more than three, no more than four, no more than five, no more than six, no more than seven, no more than eight, no more than nine, or no more than ten amino acid additions, deletions, or substitutions. Further aspects of the invention include antibodies comprising A) comprising a light chain variable region selected from the group consisting of SEQ ID NOS:27, 28, and 29 having no more than one, no more than two, no more than three, no more than four, no more than five, no more than six, no more than seven, no more than eight, no more than nine, or no more than ten amino acid additions, deletions, or substitutions, and B) a heavy chain variable region selected from the group consisting of SEQ ID NOS:9, 10, and 11 having no more than one, no more than two, no more than three, no more than four, no more than five, no more than six, no more than seven, no more than eight, no more than nine, or no more than ten amino acid additions, deletions, or substitutions.

In one variation, the antigen binding protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a light chain variable region amino acid sequence selected from the group consisting of SEQ ID NOS:27, 28, and 29. In another variation, the antigen binding protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a heavy chain variable region amino acid sequence selected from the group consisting of SEQ ID NOS:9, 10, and 11. In yet a further embodiment, the antigen binding protein comprises A) an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a light chain variable region amino acid sequence selected from the group consisting of SEQ ID NOS:27, 28, and 29, and B) an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a heavy chain variable region amino acid sequence selected from the group consisting of SEQ ID NOS:9, 10, and 11.

OSMR antigen binding proteins comprising a heavy chain variable domain having the above-defined sequence relatedness to SEQ ID NO:9 can optionally contain an amino acid other than asparagine (for example, aspartic acid) at the position corresponding to position 73 in SEQ ID NO:9. In such embodiments, the heavy chain variable domain optionally comprises the amino acid sequence set forth in SEQ ID NO:53.

OSMR antigen binding proteins comprising a heavy chain variable domain having the above-defined sequence relatedness to SEQ ID NO: 10 can optionally contain an amino acid other than asparagine (for example, aspartic acid) at the position corresponding to position 73 in SEQ ID NO: 10. In such embodiments, the heavy chain variable domain optionally comprises the amino acid sequence set forth in SEQ ID NO:54.

In certain embodiments, the antigen binding protein comprises a light chain and/or heavy chain CDR3. In some embodiments, the antigen binding protein comprises an amino acid sequence selected from the group of sequences set forth in SEQ ID NOS:36, 37, 38, 18, 19, and 20. In certain embodiments, the amino acid sequence includes no more than one, no more than two, no more than three, no more than four, no more than five, or no more than six amino acid additions, deletions, or substitutions from the exemplary sequence set forth in SEQ ID NOS:36, 37, 38, 18, 19, and 20. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS:36, 37, 38, 18, 19, and 20.

In certain embodiments, the antigen binding protein comprises a light chain and/or heavy chain CDR2. In some embodiments, the antigen binding protein comprises an amino acid sequence selected from the group of sequences set forth in SEQ ID NOS:33, 34, 35, 15, 16, and 17. In certain embodiments, the amino acid sequence includes no more than one, no more than two, no more than three, no more than four, no more than five, or no more than six amino acid additions, deletions, or substitutions from the exemplary sequence set forth in SEQ ID NOS:33, 34, 35, 15, 16, and 17. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS:33, 34, 35, 15, 16, and 17.

In certain embodiments, the antigen binding protein comprises a light chain and/or heavy chain CDR1. In some embodiments, the antigen binding protein comprises an amino acid sequence selected from the group of sequences set forth in SEQ ID NOS:30, 31, 32, 12, 13, and 14. In certain embodiments, the amino acid sequence includes no more than one, no more than two, no more than three, no more than four, no more than five, or no more than six amino acid additions, deletions, or substitutions from the exemplary sequence set forth in SEQ ID NOS:30, 31, 32, 12, 13, and 14. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS:30, 31, 32, 12, 13, and 14.

The antigen binding proteins of the invention comprise the scaffolds of traditional antibodies, including human and monoclonal antibodies, bispecific antibodies, diabodies, minibodies, domain antibodies, synthetic antibodies (sometimes referred to herein as "antibody mimetics"), chimeric antibodies, antibody fusions (sometimes referred to as "antibody conjugates"), and fragments of each, respectively. The above described CDRs, including various combinations of the CDRs, may be grafted into any of the following scaffolds.

As used herein, the term "antibody" refers to the various forms of monomeric or multimeric proteins comprising one or more polypeptide chains that specifically binds to an antigen, as variously described herein. In certain embodiments, antibodies are produced by recombinant DNA techniques. In additional embodiments, antibodies are produced by enzymatic or chemical cleavage of naturally occurring antibodies. In another aspect, the antibody is selected from the group consisting of: a) a human antibody; b) a humanized antibody; c) a chimeric antibody; d) a monoclonal antibody; e) a polyclonal antibody; f) a recombinant antibody; g) an antigen-binding fragment; h) a single chain antibody; i) a diabody; j) a triabody, k) a tetrabody, l) a Fab fragment; m) a F(ab')$_2$ fragment, n) an IgA antibody, o) an IgD antibody, p) an IgE antibody, q) an IgG1 antibody, r) an IgG2 antibody, s) an IgG3 antibody, t) an IgG4 antibody, and u) an IgM antibody.

A variable region or domain comprises at least three heavy or light chain CDRs embedded within a framework region (designated framework regions FR1, FR2, FR3, and FR4). Kabat et al., 1991, *Sequences of Proteins of Immunological Interest*, Public Health Service N.I.H., Bethesda, Md. Traditional antibody structural units typically comprise a tetramer. Each tetramer is typically composed of two identical pairs of polypeptide chains, each pair having one "light" and one "heavy" chain. The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to IgM1 and IgM2. Embodiments of the invention include all such classes and subclasses of antibodies that incorporate a variable domain or CDR of the antigen binding proteins, as described herein.

Some naturally occurring antibodies, such as those found in camels and llamas, are dimers consisting of two heavy chains and include no light chains. The invention encompasses dimeric antibodies of two heavy chains, or fragments thereof, that can bind to OSMR.

The variable regions of the heavy and light chains typically exhibit the same general structure of relatively conserved framework regions (FR) joined by three hypervariable regions, i.e., the complementarity determining regions or CDRs. The CDRs are primarily responsible for antigen recognition and binding. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3, and FR4. The assignment of amino acids to each domain is in accordance with the definitions of Kabat.

CDRs constitute the major surface contact points for antigen binding. The CDR3 or the light chain and, particularly, CDR3 of the heavy chain may constitute the most important determinants in antigen binding within the light and heavy chain variable regions. In some antibodies, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen.

Naturally occurring antibodies typically include a signal sequence, which directs the antibody into the cellular pathway for protein secretion and which is typically not present in the mature antibody. A polynucleotide encoding an antibody of the invention may encode a naturally occurring a signal sequence or a heterologous signal sequence as described below.

In one embodiment, the antigen binding protein is an antibody comprising from one to six of the exemplary CDRs described herein. The antibodies of the invention may be of any type including IgM, IgG (including IgG1, IgG2, IgG3, IgG4), IgD, IgA, or IgE antibody. In a specific embodiment the antigen binding protein is an IgG type antibody, e.g., a IgG1 antibody.

In some embodiments, for example when the antigen binding protein is an antibody with complete heavy and light chains, the CDRs are all from the same species, e.g., human. Alternatively, for example in embodiments wherein the antigen binding protein contains less than six CDRs from the sequences outlined above, additional CDRs may be either from other species or may be different human CDRs than those depicted in the exemplary sequences. For example, HCDR3 and LCDR3 regions from the appropriate sequences identified herein may be used with HCDR1, HCDR2, LCDR1, and LCDR2 being optionally selected from alternate species or different human antibody sequences, or combinations thereof. For example, the CDRs of the invention can replace the CDR regions of commercially relevant chimeric or humanized antibodies.

Specific embodiments utilize scaffold components of the antigen binding proteins that are human components. In some embodiments, however, the scaffold components can be a mixture from different species. As such, if the antigen binding protein is an antibody, such antibody may be a chimeric antibody and/or humanized antibody. In general, both "chimeric antibodies" and humanized antibodies" refer to antibodies that combine regions from more than one species. For example, "chimeric antibodies" traditionally comprise variable region(s) from a mouse (or rat, in some cases) and the constant region(s) from a human.

"Humanized antibodies" generally refer to non-human antibodies that have had the variable domain framework regions swapped for sequences found in human antibodies. Generally, in a humanized antibody, the entire antibody, except one or more CDRs, is encoded by a polynucleotide of human origin or is identical to such an antibody except within one or more CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones 1986, *Nature* 321:522-525, Verhoeyen et al., 1988, *Science* 239:1534-1536. Humanized antibodies can also be generated using mice with a genetically engineered immune system (Roque et al., 2004, Biotechnol. Prog. 20:639-654). In the exemplary embodiments described herein, the identified CDRs are human, and thus both humanized and chimeric antibodies in this context include some non-human CDRs; for example, humanized antibodies may be generated that comprise the HCDR3 and LCDR3 regions, with one or more of the other CDR regions being of a different species origin.

In one embodiment, the OSMR antigen binding protein is a multispecific antibody, and notably a bispecfic antibody, also sometimes referred to as "diabodies." These are antibodies that bind to two or more different antigens or different epitopes on a single antigen. In certain embodiments, a bispecific antibody binds OSMR and an antigen on a human effector cell (e.g., T cell). Such antibodies are useful in targeting an effector cell response against OSMR expressing cells, such as an OSMR-expressing tumor cell. In preferred embodiments, the human effector cell antigen is CD3. U.S. Pat. No. 7,235,641. Methods of making bispecific antibodies are known in the art. One such method involves engineering the Fc portion of the heavy chains such as to create "knobs" and "holes" which facilitate heterodimer formation of the heavy chains when co-expressed in a cell. U.S. Pat. No. 7,695,963. Another method also involves engineering the Fc portion of the heavy chain but uses electrostatic steering to encourage heterodimer formation while discouraging homodimer formation of the heavy chains when co-expressed in a cell. WO 09/089,004, which is incorporated herein by reference in its entirety.

In one embodiment, the OSMR antigen binding protein is a minibody. Minibodies are minimized antibody-like proteins comprising a scFv joined to a CH3 domain (Hu et al., 1996, Cancer Res. 56:3055-3061).

In one embodiment, the OSMR antigen binding protein is a domain antibody; see, for example U.S. Pat. No. 6,248,516. Domain antibodies (dAbs) are functional binding domains of antibodies, corresponding to the variable regions of either the heavy (VH) or light (VL) chains of human antibodies. dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609.

In one embodiment, the OSMR antigen binding protein is an antibody fragment, that is a fragment of any of the antibodies outlined herein that retain binding specificity to OSMR. In various embodiments, the antibody binding proteins comprise, but are not limited to, a F(ab), F(ab'), F(ab')2, Fv, or a single chain Fv fragments. At a minimum, an antibody, as meant herein, comprises a polypeptide that can bind specifically to OSMR comprising all or part of a light or heavy chain variable region, such as one or more CDRs.

Further examples of OSMR-binding antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, *Nature* 341:544-546) which consists of a single variable, (v) isolated CDR regions, (vi) F(ab')₂ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, *Science* 242:423-426, Huston et al., 1988, *Proc. Natl. Acad. Sci. U.S.A.* 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448). The antibody fragments may be modified. For example, the molecules may be stabilized by the incorporation of disulphide bridges linking the VH and VL domains (Reiter et al., 1996, *Nature Biotech.* 14:1239-1245). Aspects of the invention include embodiments wherein the non-CDR components of these fragments are human sequences.

In one embodiment, the OSMR antigen binding protein is a fully human antibody. In this embodiment, as outlined above, specific structures comprise complete heavy and light chains depicted comprising the CDR regions. Additional embodiments utilize one or more of the CDRs of the invention, with the other CDRs, framework regions, J and D regions, constant regions, etc., coming from other human antibodies. For example, the CDRs of the invention can replace the CDRs of any number of human antibodies, particularly commercially relevant antibodies Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein (including but not limited to scFvs comprising the variable domain combinations of Ab1 LCv/Ab1 HCv (SEQ ID NO:27/SEQ ID NO:9), Ab2 LCv/Ab2 HCv (SEQ ID NO:28/SEQ ID NO:10), and Ab3 LCv/Ab3 HCv (SEQ ID NO:29/SEQ ID NO: 11), and combinations thereof are encompassed by the present invention. Exemplary single chain antibodies include the following variable domain combinations: SEQ ID NO:27/SEQ ID NO:53; and SEQ ID NO:28/SEQ ID NO:54.

In one embodiment, the OSMR antigen binding protein is an antibody fusion protein (sometimes referred to herein as an "antibody conjugate"). The conjugate partner can be proteinaceous or non-proteinaceous; the latter generally being generated using functional groups on the antigen binding protein and on the conjugate partner. In certain embodiments, the antibody is conjugated to a non-proteinaceous chemical (drug) to form an antibody drug conjugate.

In one embodiment, the OSMR antigen binding protein is an antibody analog, sometimes referred to as "synthetic antibodies." For example, a variety of work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, *Proteins: Structure, Function, and Bioinformatics*, Volume 53, Issue 1:121-129. Roque et al., 2004, *Biotechnol. Prog.* 20:639-654. In addition, peptide antibody mimetics ("PAMs") can be used, as well as work based on antibody mimetics utilizing fibronection components as a scaffold.

By "protein," as used herein, is meant at least two covalently attached amino acids, which includes proteins, polypeptides, oligopeptides and peptides. In some embodiments, the two or more covalently attached amino acids are attached by a peptide bond. The protein may be made up of naturally occurring amino acids and peptide bonds, for example when the protein is made recombinantly using expression systems and host cells, as outlined below. Alternatively, the protein may include synthetic amino acids (e.g., homophenylalanine, citrulline, ornithine, and norleucine), or peptidomimetic structures, i.e., "peptide or protein analogs", such as peptoids (see, Simon et al., 1992, *Proc. Natl. Acad. Sci. U.S.A.* 89:9367, incorporated by reference herein), which can be resistant to proteases or other physiological and/or storage conditions. Such synthetic amino acids may be incorporated in particular when the antigen binding protein is synthesized in vitro by conventional methods well known in the art. In addition, any combination of peptidomimetic, synthetic and naturally occurring residues/structures can be used. "Amino acid" also includes imino acid residues such as proline and hydroxyproline. The amino acid "R group" or "side chain" may be in either the (L)- or the (S)-configuration. In a specific embodiment, the amino acids are in the (L)- or (S)-configuration.

In certain aspects, the invention provides recombinant antigen binding proteins that bind OSMR and, in some embodiments, a recombinant human OSMR or portion thereof. In this context, a "recombinant protein" is a protein made using recombinant techniques using any techniques and methods known in the art, i.e., through the expression of a recombinant nucleic acid as described herein. Methods and techniques for the production of recombinant proteins are well known in the art. Embodiments of the invention include recombinant antigen binding proteins that bind wild-type OSMR and variants thereof.

"Consisting essentially of" means that the amino acid sequence can vary by about 1, 2, 3, 4, 5, 6, 7, 8, 9, 10, 11, 12, 13, 14, or 15% relative to the recited SEQ ID NO: sequence and still retain biological activity, as described herein.

In some embodiments, the antigen binding proteins of the invention are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antigen binding protein in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 80%, and more typically with preferably increasing homologies or identities of at least 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities, such as OSMR binding.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as Table 3.

TABLE 3

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 3. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the antigen binding protein proteins as needed. Alternatively, the variant may be designed such that the biological activity of the antigen binding protein is altered. For example, glycosylation sites may be altered or removed as discussed herein.

Other derivatives of OSMR antibodies within the scope of this invention include covalent or aggregative conjugates of OSMR antibodies, or fragments thereof, with other proteins or polypeptides, such as by expression of recombinant fusion proteins comprising heterologous polypeptides fused to the N-terminus or C-terminus of a OSMR antibody polypeptide. For example, the conjugated peptide may be a heterologous signal (or leader) polypeptide, e.g., the yeast alpha-factor leader, or a peptide such as an epitope tag. OSMR antibody-containing fusion proteins can comprise peptides added to facilitate purification or identification of the OSMR antibody (e.g., poly-His). An OSMR antibody polypeptide also can be linked to the FLAG peptide as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

One embodiment of the present invention is directed to a dimer comprising two fusion proteins created by fusing an OSMR binding fragment of an OSMR antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a OSMR antibody may be substituted for the variable portion of an antibody heavy and/or light chain.

Another method for preparing oligomeric OSMR antibody derivatives involves use of a leucine zipper. Leucine zipper domains are peptides that promote oligomerization of the proteins in which they are found. Leucine zippers were originally identified in several DNA-binding proteins (Landschulz et al., Science 240:1759-64, 1988), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, *Semin. Immunol.* 6:267-78. In one approach, recombinant fusion proteins comprising OSMR antibody fragment or derivative fused to a leucine zipper peptide are expressed in suitable host cells, and the soluble oligomeric OSMR antibody fragments or derivatives that form are recovered from the culture supernatant.

Covalent modifications of antigen binding proteins are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for cross-linking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antigen binding protein included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Another type of covalent modification of the antigen binding protein comprises linking the antigen binding protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antigen binding protein to facilitate the addition of polymers such as PEG.

In some embodiments, the covalent modification of the antigen binding proteins of the invention comprises the addition of one or more labels.

The term "labeling group" means any detectable label. Examples of suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla*, *Ptilosarcus*, or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

The exemplary antigen binding proteins described herein have properties based on the distinct epitope on OSMR bound by the antigen binding protein. The term "epitope" means the amino acids of a target molecule that are contacted by an antigen binding protein, e.g., an antibody, when the antigen binding protein is bound to the target molecule. An epitope can be contiguous or non-contiguous (e.g., (i) in a single-chain polypeptide, amino acid residues that are not contiguous to one another in the polypeptide sequence but that within the context of the target molecule are bound by the antigen binding protein, or (ii) in a multimeric receptor comprising two or more individual components, e.g., OSMR and gp130 or OSMR and IL-31 receptor A, amino acid residues are present on one or more of the individual components but are still bound by the antigen binding protein. Epitope determinants can include chemically active surface groupings of molecules such as amino acids, sugar side chains, phosphoryl or sulfonyl groups, and can have specific three dimensional structural characteristics, and/or specific charge characteristics. Generally, antigen binding proteins specific for a particular target molecule will preferentially recognize an epitope on the target molecule in a complex mixture of proteins and/or macromolecules.

Methods of characterizing the epitope bound by an antigen binding protein are well known in the art, including, but not limited to, binning (cross-competition) (Miller et al "Epitope binning of murine monoclonal antibodies by a multiplexed pairing assay" *J Immunol Methods* (2011) 365, 118-25), peptide mapping (e.g., PEPSPOT™) (Albert et al "The B-cell Epitope of the Monoclonal Anti-Factor VIII Antibody ESH8 Characterized by Peptide Array Analysis" 2008 *Thromb. Haemost.* 99, 634-7), mutagenesis methods such as chimeras (Song et al "Epitope Mapping of Ibalizumab, a Humanized Anti-CD4 Monoclonal Antibody with Anti-HIV-1 Activity in Infected Patients" *J. Virol.* (2010) 84, 6935-6942), alanine scanning (Cunningham and Wells "High-resolution epitope mapping of HGH-receptor interactions by alanine-scanning mutagenesis" *Science* (1989) 244, 1081-1085), arginine scanning (Lim et al "A diversity of antibody epitopes can induce signaling through the erythropoietin receptor" *Biochemistry* (2010) 49, 3797-3804), HD exchange methods (Coates et al "Epitope mapping by amide hydrogen/deuterium exchange coupled with immobilization of antibody, on-line proteolysis, liquid chromatography and mass spectrometry" *Rapid Commun. Mass Spectrom.* (2009) 23 639-647), NMR cross saturation methods (Morgan et al "Precise epitope mapping of malaria parasite inhibitory antibodies by TROSY NMR cross-saturation" *Biochemistry* (2005) 44, 518-23), and crystallography (Gerhardt et al "Structure of IL-17A in complex with a potent, fully human neutralizing antibody" *J. Mol. Biol* (2009) 394, 905-21). The methods vary in the level of detail they provide as to the amino acids comprising the epitope. Example 4 provides an exemplary method of epitope binning.

Antigen binding proteins of the present invention include those that have an overlapping epitope with an exemplary antigen binding protein described herein, e.g., Ab1, Ab2, or Ab3. In certain embodiments, the antigen binding protein has an identical epitope as to the exemplary antigen binding proteins. In other embodiments, the antigen binding protein binds only a subset of the same amino acids as the exemplary antigen binding protein.

In certain embodiments, the OSMR antigen binding protein has an identical or overlapping epitope as Ab1, Ab2, or Ab3, and comprises a) a light chain variable domain having at least 90% identity, at least 95% identity, or is identical to the amino acid sequence set forth in SEQ ID NO:27, SEQ ID NO:28, or SEQ ID NO:29; b) a heavy chain variable domain having at least 90% identity, at least 95% identity, or is identical to the amino acid sequence set forth in SEQ ID NO:9, SEQ ID NO:10, or SEQ ID NO:11; or c) the light chain variable domain of a) and the heavy chain variable domain of b).

In certain embodiments, the OSMR antigen binding protein has an identical or overlapping epitope as Ab1, Ab2, or Ab3, and comprises a light chain variable domain having at least 90%, at least 95%, or is identical to the amino acid sequence set forth in SEQ ID NO:27 and a heavy chain variable domain having at least 90%, at least 95%, or is identical to the amino acid sequence set forth in SEQ ID NO:9; those comprising a light chain variable domain having at least 90%, at least 95%, or is identical to the amino acid sequence set forth in SEQ ID NO:28 and a heavy chain variable domain having at least 90%, at least 95%, or is identical to the amino acid sequence set forth in SEQ ID NO: 10; and those comprising a light chain variable domain having at least 90%, at least 95%, or is identical to the amino acid sequence set forth in SEQ ID NO:29 and a heavy chain variable domain having at least 90%, at least 95%, or is identical to the amino acid sequence set forth in SEQ ID NO: 11.

In certain embodiments, the OSMR antigen binding protein has an identical or overlapping epitope as Ab1, Ab2, or Ab3, and comprises a) a light chain variable domain having no more than ten or no more than five amino acid additions, deletions or substitutions from the amino acid sequence set forth in SEQ ID NO:27, SEQ ID NO:28, or SEQ ID NO:29; b) a heavy chain variable domain having no more than ten or no more than five amino acid additions, deletions or substitutions from the amino acid sequence set forth in SEQ ID NO:9, SEQ ID NO: 10, or SEQ ID NO: 11; or c) the light chain variable domain of a) and the heavy chain variable domain of b).

In certain embodiments, the OSMR antigen binding protein has an identical or overlapping epitope as Ab1, Ab2, or Ab3, and comprises a light chain variable domain having no more than ten or no more than five amino acid additions, deletions or substitutions from the amino acid sequence set forth in SEQ ID NO:27 and a heavy chain variable domain having no more than ten or no more than five amino acid additions, deletions or substitutions from the amino acid sequence set forth in SEQ ID NO:9; those comprising a light chain variable domain having no more than ten or no more than five amino acid additions, deletions or substitutions from the amino acid sequence set forth in SEQ ID NO:28 and a heavy chain variable domain having no more than ten or no more than five amino acid additions, deletions or substitutions from the amino acid sequence set forth in SEQ ID NO: 10; and those comprising a light chain variable domain having no more than ten or no more than five amino acid additions, deletions or substitutions from the amino acid sequence set forth in SEQ ID NO:29 and a heavy chain variable domain having no more than ten or no more than five amino acid additions, deletions or substitutions from the amino acid sequence set forth in SEQ ID NO: 11.

An exemplary heavy chain variable domain variant of SEQ ID NO:9 contains an amino acid other than asparagine (for example, aspartic acid) at the position corresponding to position 73 in SEQ ID NO:9. The amino acid sequence set forth in SEQ ID NO:53 is an example of a heavy chain variable domain variant of SEQ ID NO:9.

An exemplary heavy chain variable domain variant of SEQ ID NO: 10 contains an amino acid other than asparagine (for example, aspartic acid) at the position corresponding to position 73 in SEQ ID NO:10. The amino acid sequence set forth in SEQ ID NO:54 is an example of a heavy chain variable domain variant of SEQ ID NO: 10.

In certain embodiments, the OSMR antigen binding protein has an identical or overlapping epitope as Ab1, Ab2, or Ab3, and comprises a light chain variable domain comprising a) an LCDR1 having no more than three amino acid additions, deletions, or substitutions from the LCDR1 sequence set forth in SEQ ID NO:30; an LCDR2 having no more than three amino acid additions, deletions, or substitutions from the LCDR2 sequence set forth in SEQ ID NO:33; and an LCDR3 having no more than three amino acid additions, deletions, or substitutions from the LCDR3 sequence set forth in SEQ ID NO:36; b) an LCDR1 having no more than three amino acid additions, deletions, or substitutions from the LCDR1 sequence set forth in SEQ ID NO:31; an LCDR2 having no more than three amino acid additions, deletions, or substitutions from the LCDR2 sequence set forth in SEQ ID NO:34; and an LCDR3 having no more than three amino acid additions, deletions, or substitutions from the LCDR3 sequence set forth in SEQ ID NO:37; or c) an LCDR1 having no more than three amino acid additions, deletions, or substitutions from the LCDR1 sequence set forth in SEQ ID NO:32; an LCDR2 having no more than three amino acid additions, deletions, or substitutions from the LCDR2 sequence set forth in SEQ ID NO:35; and an LCDR3 having no more than three amino acid additions, deletions, or substitutions from the LCDR3 sequence set forth in SEQ ID NO:38; and a heavy chain variable domain comprising d) an HCDR1 having no more than three amino acid additions, deletions, or substitutions from the HCDR1 sequence set forth in SEQ ID NO: 12; an HCDR2 having no more than three amino acid additions, deletions, or substitutions from the HCDR2 sequence set forth in SEQ ID NO:15; and an HCDR3 having no more than three amino acid additions, deletions, or substitutions from the HCDR3 sequence set forth in SEQ ID NO:18; e) an HCDR1 having no more than three amino acid additions, deletions, or substitutions from the HCDR1 sequence set forth in SEQ ID NO:13; an HCDR2 having no more than three amino acid additions, deletions, or substitutions from the HCDR2 sequence set forth in SEQ ID NO:16; and an HCDR3 having no more than three amino acid additions, deletions, or substitutions from the HCDR3 sequence set forth in SEQ ID NO: 19; or f) an HCDR1 having no more than three amino acid additions, deletions, or substitutions from the HCDR1 sequence set forth in SEQ ID NO:14; an HCDR2 having no more than three amino acid additions, deletions, or substitutions from the HCDR2 sequence set forth in SEQ ID NO:17; and an HCDR3 having no more than three amino acid additions, deletions, or substitutions from the HCDR3 sequence set forth in SEQ ID NO:20.

Preferred OSMR antigen binding proteins described immediately above include those comprising the light chain variable domain of a) and the heavy chain variable domain of d); those comprising the light chain variable domain of b) and the heavy chain variable domain of e); and those comprising the light chain variable domain of c) and the heavy chain variable domain of f).

OSMR antigen binding proteins comprising the light chain variable domain of a) and the heavy chain variable domain of d) can optionally contain a heavy chain variable domain that comprises an amino acid other than asparagine (for example, aspartic acid) at the position corresponding to position 73 in SEQ ID NO:9. In such embodiments, the heavy chain variable domain optionally comprises the amino acid sequence set forth in SEQ ID NO:53.

OSMR antigen binding proteins comprising the light chain variable domain of b) and the heavy chain variable domain of e) can optionally contain a heavy chain variable domain that comprises an amino acid other than asparagine (for example, aspartic acid) at the position corresponding to position 73 in SEQ ID NO: 10. In such embodiments, the heavy chain variable domain optionally comprises the amino acid sequence set forth in SEQ ID NO:54.

Antigen binding proteins that have an identical epitope or overlapping epitope will often cross-compete for binding to the antigen. Thus, in certain embodiments, an antigen binding protein of the invention cross-competes with Ab1, Ab2, or Ab3. To "cross-compete" or "cross-competition" means the antigen binding proteins compete for the same epitope or binding site on a target. Such competition can be determined by an assay in which the reference antigen binding protein (e.g., antibody or antigen-binding portion thereof) prevents or inhibits specific binding of a test antigen binding protein, and vice versa. Numerous types of competitive binding assays can be used to determine if a test molecule competes with a reference molecule for binding. Examples of assays that can be employed include solid phase direct or indirect radioimmunoassay (RIA), solid phase direct or indirect enzyme immunoassay (EIA), sandwich competition assay (see, e.g., Stahli et al. (1983) *Methods in Enzymology* 9:242-253), solid phase direct biotin-avidin EIA (see, e.g., Kirkland et al., (1986) *J. Immunol.* 137:3614-9), solid phase direct labeled assay, solid phase direct labeled sandwich assay, Luminex (Jia et al. "A novel method of Multiplexed Competitive Antibody Binning for the characterization of monoclonal antibodies" *J. Immunological Methods* (2004) 288, 91-98) and surface plasmon resonance (Song et al. "Epitope Mapping of Ibalizumab, a Humanized Anti-CD4 Monoclonal Antibody with Anti-HIV-1 Activity in Infected Patients" *J. Virol.* (2010) 84, 6935-42). An exemplary method of determining cross-competition is described in Example 5. Usually, when a competing antigen binding protein is present in excess, it will inhibit binding of a reference antigen binding protein to a common antigen by at least 50%, 55%, 60%, 65%, 70%, or 75%. In some instances, binding is inhibited by at least 80%, 85%, 90%, 95%, 96%, 97%, 98%, 99%, or more.

Polynucleotides Encoding OSMR Antigen Binding Proteins

Encompassed within the invention are nucleic acids or isolated nucleic acids encoding OSMR antigen binding proteins, including antibodies, as defined herein. Preferred nucleic acids include those that encode the exemplary light and heavy chains described herein.

An exemplary nucleic acid encoding Ab1 LC is a nucleic acid comprising the sequence set forth in SEQ ID NO:21.

An exemplary nucleic acid encoding Ab2 LC is a nucleic acid comprising the sequence set forth in SEQ ID NO:22.

An exemplary nucleic acid encoding Ab3 LC is a nucleic acid comprising the sequence set forth in SEQ ID NO:23.

An exemplary nucleic acid encoding Ab1 HC is a nucleic acid comprising the sequence set forth in SEQ ID NO:3.

An exemplary nucleic acid encoding Ab2 HC is a nucleic acid comprising the sequence set forth in SEQ ID NO:4.

An exemplary nucleic acid encoding Ab3 HC is a nucleic acid comprising the sequence set forth in SEQ ID NO:5.

An exemplary nucleic acid encoding a variant Ab1 HC is a nucleic acid comprising the sequence set forth in SEQ ID NO:47.

An exemplary nucleic acid encoding a variant Ab2 HC is a nucleic acid comprising the sequence set forth in SEQ ID NO:48.

An exemplary nucleic acid encoding a variant Ab3 HC is a nucleic acid comprising the sequence set forth in SEQ ID NO:49.

Aspects of the invention include polynucleotide variants (e.g., due to degeneracy) that encode the amino acid sequences described herein.

Aspects of the invention include a variety of embodiments including, but not limited to, the following exemplary embodiments.

An isolated nucleic acid comprising a polynucleotide, wherein said polynucleotide encodes one or more polypeptides comprising an amino acid sequence selected from the group consisting of:

A. 1. a light chain variable domain sequence that is at least 90% identical to a light chain variable domain sequence set forth in SEQ ID NOS:27-29;
  2. a heavy chain variable domain sequence that is at least 90% identical to a heavy chain variable domain sequence set forth in SEQ ID NOS:9-11;
  3. a light chain variable domain of (1) and a heavy chain variable domain of (2); and B. a light chain variable domain comprising a CDR1, CDR2, CDR3 and/or a heavy chain variable domain comprising a CDR1, CDR2, CDR3 that are the same or differ by no more than a total of three amino acid additions, substitutions, and/or deletions in each CDR from the following sequences:

1. a light chain CDR1 (SEQ ID NO:30), CDR2 (SEQ ID NO:33), CDR3 (SEQ ID NO:36) or a heavy chain CDR1 (SEQ ID NO:12), CDR2 (SEQ ID NO:15), CDR3 (SEQ ID NO:18) of Ab1;
2. a light chain CDR1 (SEQ ID NO:31), CDR2 (SEQ ID NO:34), CDR3 (SEQ ID NO:37) or a heavy chain CDR1 (SEQ ID NO:13), CDR2 (SEQ ID NO:16), CDR3 (SEQ ID NO:19) of Ab2; and
3. a light chain CDR1 (SEQ ID NO:32), CDR2 (SEQ ID NO:35), CDR3 (SEQ ID NO:38) or a heavy chain CDR1 (SEQ ID NO:14), CDR2 (SEQ ID NO:17), CDR3 (SEQ ID NO:20) of Ab3.

In some embodiments, the nucleic acid encodes a polypeptide that comprises the amino acid sequence set forth in SEQ ID NO:53 or SEQ ID NO:54.

In some embodiments, the nucleic acid encodes a polypeptide that comprises the amino acid sequence set forth in SEQ ID NO:50, SEQ ID NO:51, or SEQ ID NO:52.

In preferred embodiments, the polypeptide encoded by the nucleic acid or isolated nucleic acid is a component of an antigen binding protein that binds OSMR.

Nucleotide sequences corresponding to the amino acid sequences described herein, to be used as probes or primers for the isolation of nucleic acids or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding an OSMR antigen binding proteins or a desired combination of OSMR antigen binding protein polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

In some embodiments, nucleic acids of the invention are isolated nucleic acids. An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual*, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids or isolated nucleic acids that hybridize under moderately stringent conditions, and more preferably highly stringent conditions, to nucleic acids encoding OSMR antigen binding proteins as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH.sub.2 PO.sub.4, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10.degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6 ($\log_{10}$ [Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

The variants according to the invention are ordinarily prepared by site specific mutagenesis of nucleotides in the DNA encoding the antigen binding protein, using cassette or PCR mutagenesis or other techniques well known in the art, to produce DNA encoding the variant, and thereafter expressing the recombinant DNA in cell culture as outlined herein. However, antigen binding protein fragments comprising variant CDRs having up to about 100-150 residues may be prepared by in vitro synthesis using established techniques. The variants typically exhibit the same qualitative biological activity as the naturally occurring analogue, e.g., binding to OSMR, although variants can also be selected which have modified characteristics as will be more fully outlined below.

As will be appreciated by those in the art, due to the degeneracy of the genetic code, an extremely large number of nucleic acids may be made, all of which encode the CDRs (and heavy and light chains or other components of the antigen binding protein) of the present invention. Thus, having identified a particular amino acid sequence, those skilled in the art could make any number of different nucleic acids, by simply modifying the sequence of one or more codons in a way which does not change the amino acid sequence of the encoded protein.

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the OSMR antigen binding protein coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the OSMR antigen binding protein from the host cell. Affinity purification can be accomplished, for example, by column chromatography using antibodies against the tag as an affinity matrix. Optionally, the tag can subsequently be removed from the purified OSMR antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thyrnidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein antibody that binds to OSMR polypeptide. As a result, increased quantities of a polypeptide such as an OSMR antigen binding protein are synthesized from the amplified DNA.

A ribosome-binding site is usually necessary for translation initiation of rnRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the OSMR antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an OSMR antigen binding protein of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist et al., 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318: 533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science*

253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising an OSMR antigen binding protein of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-fetoprotein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The vector may contain one or more elements that facilitate expression when the vector is integrated into the host cell genome. Examples include an EASE element (Aldrich et al. 2003 *Biotechnol Prog.* 19:1433-38) and a matrix attachment region (MAR). MARs mediate structural organization of the chromatin and may insulate the integrated vactor from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an OSMR antigen binding sequence has been inserted into the proper site of the vector, the completed vector may be inserted into a suitable host cell for amplification and/or polypeptide expression. The transformation of an expression vector for an OSMR antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an OSMR antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention. In general, host cells are transformed with a recombinant expression vector that comprises DNA encoding a desired anti-OSMR antibody polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., 1998, *Cytotechnology* 28: 31), HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces strains, Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods. The polypeptide can also be produced by operably linking the nucleic acid or isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, *Bio/Technology* 6:47 (1988). Cell-free translation systems could also be employed to produce polypeptides using RNAs derived from nucleic acid constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, New York, 1985). A host cell that comprises a nucleic acid or an isolated nucleic acid of the invention, preferably operably linked to at least one expression control sequence, is a "recombinant host cell".

In certain embodiments, cell lines may be selected through determining which cell lines have high expression levels and constitutively produce antigen binding proteins with OSMR binding properties. In another embodiment, a cell line from the B cell lineage that does not make its own antibody but has a capacity to make and secrete a heterologous antibody can be selected.

Cell-Depleting OSMR Antigen Binding Proteins

In preferred embodiments, the OSMR antigen binding protein binds OSMR and inhibits OSM and/or IL-31 binding, thereby reducing OSM- and/or IL-31-mediated signaling in OSMR-expressing cells. In certain embodiments, however, the OSMR antigen binding protein binds OSMR and targets an OSMR-expressing cell for depletion. In various aspects, the OSMR antigen binding protein inhibits OSM and/or IL-31 binding and targets the OSMR cell for depletion.

Cell-depleting OSMR antigen binding proteins are particularly useful for treating diseases or disorders associated with over expression of OSMR, e.g., an autoimmune disease, inflammatory disease, a disease or disorder associated with extracellular matrix deposition or remodeling, or an OSMR-expressing tumor. Methods of targeting cells with antigen binding proteins, e.g. antibodies, are well known in the art. Exemplary embodiments are discussed below.

Antibody Drug Conjugates

Embodiments of the invention include antibody drug conjugates (ADCs). Generally the ADC comprises an antibody conjugated to a chemotherapeutic agent, e.g., a cytotoxic agent, a cytostatic agent, a toxin, or a radioactive agent. A linker molecule can be used to conjugate the drug to the antibody. A wide variety of linkers and drugs useful in ADC technology are known in the art and may be used in embodiments of the present invention. (See US20090028856; US2009/0274713; US2007/0031402; WO2005/084390; WO2009/099728; U.S. Pat. Nos. 5,208,020; 5,416,064; 5,475,092; 5,585,499; 6,436,931; 6,372,738; and 6,340,701, all incorporated herein by reference).

Linkers

In certain embodiments, the ADC comprises a linker made up of one or more linker components. Exemplary linker components include 6-maleimidocaproyl, maleimidopropanoyl, valine-citrulline, alanine-phenylalanine, p-aminobenzyloxycarbonyl, and those resulting from conjugation with linker reagents, including, but not limited to, N-succinimidyl 4-(2-pyridylthio) pentanoate ("SPP"), N-succinimidyl 4-(N-maleimidomethyl) cyclohexane-1 carboxylate ("SMCC," also referred to herein also as "MCC"), and N-succinimidyl (4-iodo-acetyl) aminobenzoate ("SIAB").

Linkers may be a "cleavable" linker or a "non-cleavable" linker (Ducry and Stump, *Bioconjugate Chem.* 2010, 21, 5-13; incorporated herein by reference in its entirety) Cleavable linkers are designed to release the drug when subjected to certain environment factors, e.g., when internalized into the target cell. Cleavable linkers include acid labile linkers, protease sensitive linkers, photolabile linkers, dimethyl linker or disulfide-containing linkers. Non-cleavable linkers tend to remain covalently associated with at least one amino acid of the antibody and the drug upon internalization by and degradation within the target cell. An exemplary non-cleavable linker is MCC.

Drugs

In certain embodiments, the antibody is conjugated to a chemotherapeutic agent. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above. Other chemotherapeutic agents that can be used with the present invention are disclosed in US Publication No. 20080171040 or US Publication No. 20080305044, each of which is incorporated herein in its entirety by reference.

It is contemplated that an antibody may be conjugated to two or more different chemotherapeutic agents or a pharmaceutical composition may comprise a mixture of antibodies wherein the antibody component is identical except for being conjugated to a different chemotherapeutic agent. Such embodiments may be useful for targeting multiple biological pathways with a target cell.

In preferred embodiments, the ADC comprises an antibody conjugated to one or more maytansinoid molecules, which are mitotic inhibitors that act by inhibiting tubulin polymerization. Maytansinoids, including various modifications, are described in U.S. Pat. Nos. 3,896,111; 4,151,042; 4,137,230; 4,248,870; 4,256,746; 4,260,608; 4,265,814; 4,294,757; 4,307,016; 4,308,268; 4,309,428; 4,313,946; 4,315,929; 4,317,821; 4,322,348; 4,331,598; 4,361,650; 4,364,866; 4,424,219; 4,450,254; 4,362,663; 4,371,533; and WO 2009/099728. Maytansinoid drug moieties may be isolated from natural sources, produced using recombinant technology, or prepared synthetically. Exemplary maytansinoids include C-19-dechloro (U.S. Pat. No. 4,256,746), C-20-hydroxy (or C-20-demethyl)+/– C-19-dechloro (U.S. Pat. Nos. 4,307,016 and 4,361,650), C-20-demethoxy (or C-20-acyloxy (—OCOR), +/– dechrolo (U.S. Pat. No. 4,294,757), C-9-SH (U.S. Pat. No. 4,424,219), C-14-alkoxymethyl (demethoxy/CH2OR) (U.S. Pat. No. 4,331,598), C-14-hydroxymethyl or acyloxymethyl (CH2OH or CH2OAc) (U.S. Pat. No. 4,450,254), C-15-hydroxy/acyloxy (U.S. Pat. No. 4,364,866), C-15-methoxy (U.S. Pat. Nos. 4,313,946 and 4,315,929), C-18-N-demethyl (U.S. Pat. Nos. 4,362,663 and 4,322,348), and 4,5-deoxy (U.S. Pat. No. 4,371,533).

Various positions on maytansinoid compounds may be used as the linkage position, depending upon the type of link desired. For example, for forming an ester linkage, the C-3 position having a hydroxyl group, the C-14 position modified with hydrozymethyl, the C-15 position modified with a hydroxyl a group, and the C-20 position having a hydroxyl group are all suitable (U.S. Pat. Nos. 5,208,020, RE39151, and 6,913,748; US Patent Appl. Pub. Nos. 20060167245 and 20070037972, and WO 2009099728).

Preferred maytansinoids include those known in the art as DM1, DM3, and DM4 (US Pat. Appl. Pub. Nos. 2009030924 and 20050276812, incorporated herein by reference).

ADCs containing maytansinoids, methods of making such ADCs, and their therapeutic use are disclosed in U.S. Pat. Nos. 5,208,020 and 5,416,064, US Pat. Appl. Pub. No. 20050276812, and WO 2009099728 (all incorporated by reference herein). Linkers that are useful for making maytansinoid ADCs are know in the art (U.S. Pat. No. 5,208,020 and US Pat. Appl. Pub. Nos. 2005016993 and 20090274713; all incorporated herein by reference). Maytansinoid ADCs comprising an SMCC linker may be prepared as disclosed in US Pat. Publ. No. 2005/0276812.

Effector Function-Enhanced Antibodies

One of the functions of the Fc portion of an antibody is to communicate to the immune system when the antibody binds its target. This is considered "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fc with proteins of the complement system, e.g., C1q.

The IgG subclasses vary in their ability to mediate effector functions. For example, IgG1 is much superior to IgG2 and IgG4 at mediating ADCC and CDC. Thus, in embodiments wherein a cell expressing OSMR is targeted for destruction, an anti-OSMR IgG1 antibody would be preferred.

The effector function of an antibody can be increased, or decreased, by introducing one or more mutations into the Fc. Embodiments of the invention include antigen binding proteins, e.g., antibodies, having an Fc engineered to increase effector function (U.S. Pat. No. 7,317,091 and Strohl, Curr. Opin. Biotech., 20:685-691, 2009; both incorporated herein by reference in its entirety). Exemplary IgG1 Fc molecules having increased effector function include (based on the Kabat numbering scheme) those have the following substitutions:

S239D/I332E
S239D/A330S/I332E
S239D/A330L/I332E
S298A/D333A/K334A
P247I/A339D
P247I/A339Q
D280H/K290S
D280H/K290S/S298D
D280H/K290S/S298V
F243L/R292P/Y300L
F243L/R292P/Y300L/P396L
F243L/R292P/Y300L/V305I/P396L
G236A/S239D/I332E
K326A/E333A
K326W/E333S

K290E/S298G/T299A
K290N/S298G/T299A
K290E/S298G/T299A/K326E
K290N/S298G/T299A/K326E

Further embodiments of the invention include antigen binding proteins, e.g., antibodies, having an Fc engineered to decrease effector function. Exemplary Fc molecules having decreased effector function include (based on the Kabat numbering scheme) those have the following substitutions:

N297A (IgG1)
L234A/L235A (IgG1)
V234A/G237A (IgG2)
L235A/G237A/E318A (IgG4)
H268Q/V309L/A330S/A331S (IgG2)
C220S/C226S/C229S/P238S (IgG1)
C226S/C229S/E233P/L234V/L235A (IgG1)
L234F/L235E/P331S (IgG1)
S267E/L328F (IgG1)

Another method of increasing effector function of IgG Fc-containing proteins is by reducing the fucosylation of the Fc. Removal of the core fucose from the biantennary complex-type oligosachharides attached to the Fc greatly increased ADCC effector function without altering antigen binding or CDC effector function. Several ways are known for reducing or abolishing fucosylation of Fc-containing molecules, e.g., antibodies. These include recombinant expression in certain mammalian cell lines including a FUT8 knockout cell line, variant CHO line Lec13, rat hybridoma cell line YB2/0, a cell line comprising a small interfering RNA specifically against the FUT8 gene, and a cell line coexpressing β-1,4-N-acetylglucosaminyltransferase III and Golgi α-mannosidase II. Alternatively, the Fc-containing molecule may be expressed in a non-mammalian cell such as a plant cell, yeast, or prokaryotic cell, e.g., E. coli. Thus, in certain embodiments of the invention, a composition comprises an antibody, e.g., Ab1, Ab2, or Ab3 having reduced fucosylation or lacking fucosylation altogether.

Pharmaceutical Compositions

In some embodiments, the invention provides a pharmaceutical composition comprising a therapeutically effective amount of one or a plurality of the antigen binding proteins of the invention together with a pharmaceutically effective diluents, carrier, solubilizer, emulsifier, preservative, and/or adjuvant. In certain embodiments, the antigen binding protein is an antibody. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of an OSMR antigen binding protein, e.g., an OSMR-binding antibody, are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18$^{th}$ Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, OSMR antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the OSMR antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired OSMR antigen binding protein in a pharmaceutically acceptable vehicle. A particularly suitable vehicle for parenteral injection is sterile distilled water in which the OSMR antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, OSMR antigen binding proteins are advantageously formulated as a dry, inhalable powder. In specific embodiments, OSMR antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. OSMR antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the OSMR antigen binding protein. Diluents, flavorings, low melting point waxes, vegetable oils, lubricants, suspending agents, tablet disintegrating agents, and binders may also be employed.

Additional pharmaceutical compositions will be evident to those skilled in the art, including formulations involving OSMR antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(-)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering OSMR antigen binding protein formulations, which can be used as pharmaceutical compositions, as described in international patent application WO 06138181A2 (PCT/US2006/022599), which is incorporated by reference in its entirety herein.

As discussed above, certain embodiments provide OSMR antigen binding proteins protein compositions, particularly pharmaceutical OSMR antigen binding protein compositions that comprise, in addition to the OSMR antigen binding protein, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in OSMR antigen binding protein formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the OSMR antigen binding protein formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of OSMR antigen binding protein formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the OSMR antigen binding protein formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (.about. 18 to 24 months). An important point to note is that preservative effectiveness should be demonstrated in the final formulation containing the active drug and all excipient components.

OSMR antigen binding protein formulations generally will be designed for specific routes and methods of administration, for specific administration dosages and frequencies of administration, for specific treatments of specific diseases, with ranges of bioavailability and persistence, among other things. Formulations thus may be designed in accordance with the invention for delivery by any suitable route, including but not limited to orally, aurally, opthalmically, rectally, and vaginally, and by parenteral routes, including intravenous and intra-arterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an OSMR antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the OSMR antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of an OSMR antigen binding protein preferably results in a decrease in severity of disease symptoms, in an increase in frequency or duration of disease symptom-free periods, or in a prevention of impairment or disability due to the disease affliction.

Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163, all incorporated by reference herein.

Methods of Diagnosing or Treating a OSMR-Associated Disease or Disorder

The OSMR antigen binding proteins of the invention are particularly useful for detecting OSMR in a biological sample. In certain embodiments, a biological sample obtained from a patient is contacted with a OSMR antigen binding protein. Binding of the OSMR antigen binding protein to OSMR is then detected to determine the presence or relative amount of OSMR in the sample. Such methods may be useful in diagnosing or determining patients that are amenable to treatment with an OSMR antigen binding protein.

In certain embodiments, an OSMR antigen binding protein of the invention is used to diagnose, detect, or treat an autoimmune disorder, inflammatory disorder, or disorder associated with extracellular matrix deposition or remodeling.

In treating these disorders, the OSMR antigen binding protein may target OSMR-expressing cells of the immune system for destruction and/or may block the interaction of OSMR with OSM and/or IL-31.

Diseases or disorders that are associated with OSMR-mediated signaling are particularly amenable to treatment with one or more OSMR antigen binding proteins disclosed herein. Such disorders include, but are not limited to, inflammation, pain, pruritis, prurigo nodularis, dermatitis, asthma, autoimmune disease, paraneoplastic autroimmune diseases, cartilage inflammation, fibrosis (including, but not limited to, pulmonary fibrosis and skin fibrosis), fibrotic disease, chronic obstructive pulmonary disease (COPD), interstitial pneumonitis, abnormal collagen deposition, systemic cutaneous amyloidosis, primary cutaneous amyloidosis, Behcet's disease, nasal polyposis, liver cirrhosis, cartilage degradation, bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, scleroderma-associated interstitial lung disease, vasculitis, myolitis, polymyolitis, dermatomyolitis, polyarteritis nodossa, Wegener's granulomatosis, arteritis, ploymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophogitis, eosinophilic bronchitis, bronchitis, Guillain-Barre disease, Type I diabetes mellitus, thyroiditis (e.g., Graves' disease), Addison's disease, Reynaud's phenomenon, autoimmune hepatitis, GVHD, transplantation rejection, kidney damage, cardiovascular disease, infection, sepsis, HIV infection, trauma, kidney allograft nephropathy, IgA nephropathy, diabetic nephropathy, diabetic retinopathy, macular degeneration, biliary atresia, congestive heart failure, atherosclerosis, restenosis, radiation-induced fibrosis, chemotherapy-induced fibrosis, burns, surgical trauma, glomerulosclerosis, and the like.

In preferred embodiments, the autoimmune disorder, inflammatory disorder, or disorder associated with extracellular matrix deposition or remodeling is fibrosis, cartilage degradation, arthritis, rheumatoid arthritis, scleroderma, scleroderma-associated interstitial lung disease, idiopathic pulmonary fibrosis, cirrhosis, psoriasis, atopic dermatitis, systemic cutaneous amyloidosis, primary cutaneous amyloidosis, inflammation, pruritic inflammation, prurigo nodularis, and pain.

In certain embodiments, an OSMR antigen binding protein of the invention is used to diagnose, detect, or treat a cancer or tumorigenic disorder. In treating a cancer or tumorigenic disorder, the OSMR antigen binding protein may target OSMR-expressing cells for destruction and/or may block the interaction of OSM and/or IL-31 with OSMR, thereby reducing OSMR mediated signaling. It is contemplated that the OSMR antigen binding proteins that block OSM- and/or IL-31-mediated signaling would be useful in promoting improved survival in cancer patients. Cancer or tumorigenic disorders that may be diagnosed, detected or treated with an OSMR antigen binding protein include, but are not limited to, solid tumors generally, lung cancer, ovarian cancer, breast cancer, prostate cancer, endometrial cancer, renal cancer, esophageal cancer, pancreatic cancer, squamous cell carcinoma, uveal melanoma, cervical cancer, colorectal cancer, bladder, brain, pancreatic, head, neck, liver, leukemia, lymphoma and Hodgkin's disease, multiple myeloma, melanoma, gastric cancer, astrocytic cancer, stomach, and pulmonary adenocarcinoma.

The antigen binding proteins may be used to inhibit tumor growth, progression, and/or metastasis. Such inhibition can be monitored using various methods. For instance, inhibition can result in reduced tumor size and/or a decrease in metabolic activity within a tumor. Both of these parameters can be measured by MRI or PET scans, for example. Inhibition can also be monitored by biopsy to ascertain the level of necrosis, tumor cell death, and the level of vascularity within the tumor. The extent of metastasis can be monitored using known methods.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

EXAMPLES

The following examples, both actual and prophetic, are provided for the purpose of illustrating specific embodiments or features of the present invention and are not intended to limit its scope.

Example 1: Production of Anti-OSMR Antibodies Using the XENOMOUSE® Platform

Fully human antibodies directed against human OSMR were generated using XENOMOUSE® technology (as described in U.S. Pat. Nos. 6,114,598; 6,162,963; 6,833,268; 7,049,426; 7,064,244, which are incorporated herein by reference in their entirety; and in Green et al., *Nature Genetics* 7:13-21, 1994; Mendez et al., *Nature Genetics* 15:146-56; 1997; Green et al., *J. Ex. Med.* 188:483-95, 1998; and Kellermann et al., *Current Opinion in Biotechnology*, 13:593-7, 2002).

To produce antibodies to OSMR, two different strains of XENOMOUSE® animals, i.e., XMG2-KL and XMG4-KL mice, were immunized with human OSMR-Fc soluble proteins (prepared by Amgen, Seattle, Wash.). A suitable amount of immunogen (i.e., ten Ctg/mouse of soluble human OSMR-Fc protein) was used for initial immunization of XENOMOUSE® animals according to the methods disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. Following the initial immunization, subsequent boost immunizations of immunogen (five ag/mouse of soluble human OSMR-Fc protein) were administered on a schedule and for the duration necessary to induce a suitable titer of anti-OSMR antibody in the mice.

Sera were collected at approximately four weeks after the first injection and specific titers were determined by ELISA. The protocol used to titer the XENOMOUSE® animals was as follows: Costar 3368 medium binding plates were coated with neutravadin @8 µg/mL (50 µL/well) and incubated at 4° C. in 1×PBS/0.05% azide overnight. Plates were washed using TiterTek 3-cycle wash with RO water. Plates were blocked using 250 µL of 1×PBS/1% milk and incubated for at least 30 minutes at RT. Block was washed off using TiterTek 3-cycle wash with RO water. One then captured biotinylated huOSMR-FNFH (prepared by Amgen, Seattle, Wash.) at 2 µg/mL in 1×PBS/1% milk/10 mM Ca2+(assay diluent) 50 µl/well and incubated for 1 hr at RT. One then washed using TiterTek 3-cycle wash with RO water. For the primary antibody, sera was titrated 1:3 in duplicate from 1:100. This was done in assay diluent 50 µL/well and incubated for 1 hr at RT. One then washed using TiterTek 3-cycle wash with RO water. The secondary antibody was goat anti Human IgG Fc HRP @ 400 ng/mL in assay diluent at 50 µL/well. This was incubated for 1 hr at RT. This was then washed using TiterTek 3-cycle wash with RO water and patted dry on paper towels. For the substrate, one-step TMB solution (Neogen, Lexington, Ky.) was used (50 µL/well) and the substrate was allowed to develop for 30 min at RT.

Animals exhibiting suitable titers were identified. Five XMG2KL animals were identified with a specific IgG immune response to OSMR. Spleens and draining lymph nodes were harvested from these animals and pooled together for hybridoma generation. Five XMG4KL animals with specific immune responses were similarly harvested and advanced as a separate fusion screening campaign. Enriched B cells from immune animals were fused to non-secretory myeloma P3×63Ag8.653 cells ((American Type Culture Collection CRL-1580; Kearney et al, *J. Immunol.* 123: 1548-50, 1979) to generate hybridomas using standard techniques (Kohler et al., *Nature* 256, 495-7, 1975).

Hybridomas were then plated at high density (multiple different hybridoma clones per well) onto 96-well tissue culture plates and grown for four weeks. Hybridoma line supernatants were screened for binding to full length human and cynomolgus OSMR expressed on transiently transfected 293T cells by Fluorometric Microvolume Assay Technology (FMAT) (Applied Biosystems, Foster City, Calif.). Briefly, in 384-well FMAT plates, 40 μl mixture of 3,000 OSMR 293T transfected cells and 15,000 parental 293T cells were combined with 15 μL of hybridoma supernatant and 10 μL of anti-human light chain (hukappa/hulambda) Alexa647 (Invitrogen, Carlsbad, Calif.) labeled secondary antibody (1.0 μg/mL final concentration). Plates were then incubated for three hours at room temperature and fluorescence was read using the FMAT reader. These screens identified 885 hybridoma lines which bind to both human and cynomologous OSMR.

Example 2: Human OSMR-Blocking Assays

The ability of OSMR antibodies to block signaling through human OSMR was determined using two assays with either human oncostatin M (OSM) or human interleukin 31 (IL-31) as the ligand. In combination, the assays were used to determine if the antibodies could inhibit signaling of OSMR triggered through the binding of OSM and/or IL-31.

In the first screen, antibodies were evaluated for their ability to block the signaling of OSM through OSMR. Stimulation of primary normal human lung fibroblasts with OSM induces phosphorylation of STAT3 and its subsequent translocation to the nucleus. Cells were seeded at 3000 cells per well in Costar 384-well plates and allowed to adhere overnight. Cells were pre-treated with antibody supernatants for twenty minutes, and then stimulated with 80 pM human OSM for 30 minutes. Cells were then washed 3× in PBS, fixed with a 3.5% formaldehyde solution, washed (3× in PBST) and permeabilized with a 0.5% Triton X-100 solution. Cells were then stained with an anti-phosphoSTAT3 antibody for an hour, washed and stained with an AlexaFluor conjugated antibody (all contained within the HitKit from Cellomics). Plates were covered and read on the ArrayScan instrument using the Cellomics proprietary algorithm to generate a Nuclear Intensity value and a Cytoplasmic Intensity value. Results were reported as the difference between these two values, and were further normalized to control data containing maximally stimulated cells and media-treated cells (POC).

In the second assay, antibodies were evaluated for their ability to inhibit a proliferative signal of IL-31 through OSMR in a stable cell line that overexpressed human IL-31RA4 and OSMR. BaF3 cells were stably transfected with two plasmids: pcDNA3.1+huOSMRb (NeoR) and pcDNA3.1+huIL31RA4 (ZeoR). In the absence of murine 11-3, this cell line is only able to proliferate in response to human IL-31 and, therefore, could be used to specifically evaluate the blocking ability of anti-OSMR antibodies. BaF3 cells were plated in 96-well plates at a density of 20,000 cells per well. Antibodies and ligand (huIL-31, Peprotech) were added to the wells to a final volume of 100 μL, and plates were incubated for 72 hours in 5% CO2, 37 C humidified chamber. Following incubation, 20 μL of Alamar Blue was added to each well and plates were returned to the incubator. Plates were read on a Molecular Devices Vmax Plate reader (570-600 nm) at various timepoints post-addition of Alamar Blue.

The results of the two assays are presented in Table 4 below. Over 3000 hybridoma supernatants were screened for blocking ability in these two assays; the top 200 blockers were further tested in a 4-point titration, with 14 being chosen for production of recombinant protein and further testing. The IC50 for three exemplary antibodies (antibodies 1-3) is shown for both assays. Some antibodies inhibited OSM-induced STAT3 translocation more completely than they inhibited IL-31-induced proliferation, and vice versa. All three antibodies, however, were potent inhibitors of OSM- and IL-31 mediated signaling.

TABLE 4

| IC50 | Ab1 | Ab2 | Ab3 |
|---|---|---|---|
| OSM | 157 pM | 252 pM | 1.35 nM |
| IL-31 | 35.2 pM | 27.6 pM | 780 pM |

Example 3: Cynomolgus OSMR Blocking Assays

The ability of OSMR antibodies to block signaling through cynomolgus OSMR was explored using two assays with either human OSM or human IL-31 as the ligand.

In the first screen, antibodies were evaluated for their ability to block the signaling of OSM through cynomolgus OSMR by using a primary kidney epithelial cell line. Stimulation of these cells with cynomolgus (cyno) OSM induces phosphorylation of STAT3 and its subsequent translocation to the nucleus. Cells were seeded at 3000 cells per well in Costar 384-well plates and allowed to adhere overnight. Cells were pre-treated with antibody supernatants for twenty minutes, and then stimulated with 80 pM cyno OSM for 30 minutes. Cells were then washed 3× in PBS, fixed with a 3.5% formaldehyde solution, washed (3× in PBST) and permeabilized with a 0.5% Triton X-100 solution. Cells were then stained with an anti-phosphoSTAT3 antibody for an hour, washed and stained with an AlexaFluor conjugated antibody (all contained within the HitKit from Cellomics). Plates were covered and read on the ArrayScan instrument using the Cellomics proprietary algorithm to generate a Nuclear Intensity value and a Cytoplasmic Intensity value. Results were reported as the difference between these two values, and were further normalized to control data containing maximally stimulated cells and media-treated cells (POC).

In the second assay, antibodies were evaluated for their ability to inhibit a proliferative signal of IL-31 through cynomolgus OSMR in a stable cell line that overexpressed cyno IL-31RA and OSMR. Similarly to Example 2, BaF3 cells were plated in 96-well plates at a density of 20,000 cells per well. Antibodies and ligand (cynomolgus IL-31, in-house, i.e., Amgen, Seattle, Wash.) were added to the wells to a final volume of 100 μL, and plates were incubated for 72 hours in 5% C02, 37C humidified chamber. Following incubation, 20 μL of Alamar Blue was added to each well and plates were returned to the incubator. Plates were read on Molecular Devices Vmax Plate reader (570-600 nm) at various timepoints post-addition of Alamar Blue.

The results of the two assays are presented in Table 5 below with the IC50 for each antibody shown for both assays. The results confirm that each of antibodies 1, 2, and 3 are potent inhibitors of OSM- and IL-31 mediated signaling.

TABLE 5

| IC50 | Ab1 | Ab2 | Ab3 |
|---|---|---|---|
| OSM | 1.26 nM | 518 pM | 1.24 nM |
| IL-31 | 225 pM | 29.3 pM | 6.87 nM |

Example 4: Epitope Binning of Anti-OSMR Antibodies

Antibody competition studies were performed to characterize the epitopes of the anti-OSMR xenomouse antibodies. Antibodies that compete with each other can be thought of as binding the same site on the target. In these experiments, OSMR or irrelevant antibodies were captured onto streptavidin-coated Luminex beads pre-bound to a capture antibody (biotinylated monovalent mouse anti-human IgG Fc antibody). OSMR antigen or buffer (no antigen) was added to wells, and a probe antibody was added to each well and detected with a PE-labeled monovalent mouse anti-human IgG Fc antibody. Mean fluorescence intensity of each well was measured. For a full reference, see Jia et al., *J. Immunol. Methods* 288: 91-8, 2004. Detection of fluorescence in a given well indicated that the probe antibody was able to bind to OSMR, even in the presence of the other OSMR antibody, demonstrating that they are binding to separate epitopes. A minimum of three bins were found as shown in Table 6 below.

TABLE 6

| Bin 1 | Ab4 |
|---|---|
| Bin 2 | Ab1, Ab2, Ab3, Ab5, Ab6, Ab7, Ab8, Ab9, Ab10, Ab11, Ab12, and Ab13 |
| Bin 3 | Ab14 |

Example 5: Affinity Determination of Anti-OSMR Antibodies

The affinities of anti-OSMR antibodies were determined. Kinetic rate constant determinations were performed to investigate the interaction of antibodies 1-3 (Abs 1-3) to human OSMR.

Biosensor analysis was conducted at 25° C. in a HBS-EP+(1×) buffer system (10 mM HEPES pH 7.4, 150 mM NaCl, 3.0 mM EDTA, 0.05% Surfactant P20) using a Biacore 3000 optical biosensor equipped with a CM5 sensor chip. All reagents were kept at 8° C. prior to injection. Goat anti-human IgG (Jackson ImmunoResearch, #109-005-098) was immobilized (~3000 RU) to the sensor chip via standard amine coupling to Flow Cells 1 and 2 and then blocked with ethanolamine. hOSMR.FH was prepared in running buffer at 150 nM and diluted 3-fold to 0.617 nM. Antibodies 1-3 were diluted (0.25 to 0.5 µg/mL) in running buffer. The antibodies were injected (15 µL) over Flow Cell 2 at a flow rate of 10 µL/min. About 50 RU of antibody was captured. The surface was allowed to stabilize (90 s) and then each concentration (150, 50.0, 16.7, 5.56, 1.85 and 0.617) of hOSMR was passed over Flow Cells 1 and 2 at a flow rate of 50 µL/min to observe the association (5 min) and dissociation (5 min). Samples were run in duplicate and in random order.

Buffer analyte blanks (0 nM hOSMR) were injected before, in-between, and after sample injections. Antibodies were injected (15 µL) over Flow Cell 2 at a flow rate of 10 µL/min. About 50 RU of antibody was captured. The surface was allowed to stabilize (90 s) and then each concentration (150 nM) of hOSMR was passed over Flow Cells 1 and 2 at a flow rate of 50 µL/min to observe the association (5 min) and dissociation (1-2 hr). The samples were run in triplicate.

Buffer analyte blanks (0 nM hOSMR) were injected before and after the sample injections. The surface was regenerated at a flow rate of 50 L/min with two injections of 10 mM glycine (pH 1.5, 50 µL). This was followed by a buffer blank injection (15 s).

Data was analyzed with Scrubber 2.0 software as follows. Data from Flow Cell 2 was subtracted from the data from Flow Cell 1 (blank reference). The reference subtracted data (2-1) was then subtracted (double referenced) from the nearest 0 nM concentration data. The double referenced long dissociation data was fit to a 1:1 binding model to determine the dissociation rate constant (kd). This dissociation rate constant was used as a fixed parameter to fit the double referenced short dissociation data to a 1:1 binding model in order to determine the association rate constant (ka) and the equilibrium dissociation constant (Kd).

The reagents were well-behaved under the experimental conditions and the data (see Table 7 below) fit fairly well to a 1:1 binding model.

TABLE 7

| Antibody | Antigen | $k_a$ (1/Ms) | $k_d$ (1/s) | $K_d$ (pM) |
|---|---|---|---|---|
| Ab1 | huOSMR | $4.47 \times 10^5$ | $9.95 \times 10^{-5}$ | 221 |
| Ab2 | huOSMR | $5.50 \times 10^5$ | $1.81 \times 10^{-5}$ | 32.7 |
| Ab3 | huOSMR | $9.47 \times 10^4$ | $1.02 \times 10^{-4}$ | 1080 |

Example 6: Anti-OSMR Antibodies

Fully human antibodies directed against human OSMR were generated using XENOMOUSE® technology described above in Example 1. Each of antibodies 1, 2, and 3 were demonstrated to be potent inhibitors of OSM- and/or IL-31-mediated signaling. Sequences of antibodies 1, 2, and 3 (i.e., Ab1, Ab2, and Ab3) were determined and are set forth in Table 8 below.

TABLE 8

| Description | SEQ ID NO | Sequence |
|---|---|---|
| Ab1-Heavy Chain nucleotide | 3 | caggtgcagctggtgcagtctggggctgaggtgaagaagcctggggc ctcagtgaaggtctcctgcaaggcttctggatacaccttcaccagtt atgatatcaactgggtgcgacaggccactggacaggggcttgagtgg atgggatggatgaaccctaatagtggtaacacagactatgcacagaa gttccagggcagagtcaccatgaccaggaacatttccataagcacgg cctacattgagctgagcagcctgagatctgaggacacggccgtttat tactgtgcgagagatatggtggctgcgaatacggattactacttcta ctacggtatggacgtctggggccaagggaccacggtcaccgtctcct |

TABLE 8-continued

| Description | SEQ ID NO | Sequence |
|---|---|---|
| | | cagctagcaccaagggcccatcggtcttccccctggcgccctgctcc aggagcacctccgagagcacagcggccctgggctgcctggtcaagga ctacttccccgaaccggtgacggtgtcgtggaactcaggcgctctga ccagcggcgtgcacaccttcccagctgtcctacagtcctcaggactc tactccctcagcagcgtggtgaccgtgccctccagcaacttcggcac ccagacctacacctgcaacgtagatcacaagcccagcaacaccaagg tggacaagacagttgagcgcaaatgttgtgtcgagtgcccaccgtgc ccagcaccacctgtggcaggaccgtcagtcttcctcttccccccaaa acccaaggacaccctcatgatctcccggacccctgaggtcacgtgcg tggtggtggacgtgagccacgaagaccccgaggtccagttcaactgg tacgtggacggcgtggaggtgcataatgccaagacaaagccacggga ggagcagttcaacagcacgttccgtgtggtcagcgtcctcaccgttg tgcaccaggactggctgaacggcaaggagtacaagtgcaaggtctcc aacaaaggcctcccagcccccatcgagaaaaccatctccaaaaccaa agggcagccccgagaaccacaggtgtacaccctgcccccatcccggg aggagatgaccaagaaccaggtcagcctgacctgcctggtcaaaggc ttctaccccagcgacatcgccgtggagtgggagagcaatgggcagcc ggagaacaactacaagaccacacctcccatgctggactccgacggct ccttcttcctctacagcaagctcaccgtggacaagagcaggtggcag caggggaacgtcttctcatgctccgtgatgcatgaggctctgcacaa ccactacacgcagaagagcctctccctgtctccgggtaaa |
| Ab2-Heavy Chain nucleotide | 4 | caggtgcagctggtgcagtctggggctgaggtgaagaagcctggggc ctcagtgaaggtctcctgcaaggcttctggatacaccttcaccagtt atgaaatcaactgggtgcgacaggccactggacaagggcttgagtgg atgggatggatgaaccctaacagtggttacacagtctatgcacagaa gttccagggcagagtcaccatgaccaggaacacctccataagcacag cctacatggaaatgagcagcctgagatctgaggacacggccgtgtat tactgtgcgagagatatagtggctgcgaatacggattactacttcta ttatggtatggacgtctggggccaagggaccacggtcaccgtctcct cagctagcaccaagggcccatcggtcttccccctggcgccctgctcc aggagcacctccgagagcacagcggccctgggctgcctggtcaagga ctacttccccgaaccggtgacggtgtcgtggaactcaggcgctctga ccagcggcgtgcacaccttcccagctgtcctacagtcctcaggactc tactccctcagcagcgtggtgaccgtgccctccagcaacttcggcac ccagacctacacctgcaacgtagatcacaagcccagcaacaccaagg tggacaagacagttgagcgcaaatgttgtgtcgagtgcccaccgtgc ccagcaccacctgtggcaggaccgtcagtcttcctcttccccccaaa acccaaggacaccctcatgatctcccggacccctgaggtcacgtgcg tggtggtggacgtgagccacgaagaccccgaggtccagttcaactgg tacgtggacggcgtggaggtgcataatgccaagacaaagccacggga ggagcagttcaacagcacgttccgtgtggtcagcgtcctcaccgttg tgcaccaggactggctgaacggcaaggagtacaagtgcaaggtctcc aacaaaggcctcccagcccccatcgagaaaaccatctccaaaaccaa agggcagccccgagaaccacaggtgtacaccctgcccccatcccggg aggagatgaccaagaaccaggtcagcctgacctgcctggtcaaaggc ttctaccccagcgacatcgccgtggagtgggagagcaatgggcagcc ggagaacaactacaagaccacacctcccatgctggactccgacggct ccttcttcctctacagcaagctcaccgtggacaagagcaggtggcag caggggaacgtcttctcatgctccgtgatgcatgaggctctgcacaa ccactacacgcagaagagcctctccctgtctccgggtaaa |
| Ab3-Heavy Chain nucleotide | 5 | caggttcatctggtgcagtctggagctgaggtgaagaagcctggggc ctcagtgaaggtctcctgcaaggcttctggttacacctttaccagct atggtatcagctgggtgcgacaggcccctggacaagggcttgagtgg atgggatggctcagcacttacagtggtaacacaaactatgcacagaa gctccagggcagagtcaccatgaccacagacacatccacgagcacag cctacatggagctgaggagcctgagatctgacgacacggccgtgtat tactgtgcgagagggaacttctactactacggtatggacgtctgggg ccaggggaccacggtcaccgtctcctcagctagcaccaagggcccat cggtcttccccctggcgccctgctccaggagcacctccgagagcaca gcggccctgggctgcctggtcaaggactacttccccgaaccggtgac ggtgtcgtggaactcaggcgctctgaccagcggcgtgcacaccttcc cagctgtcctacagtcctcaggactctactccctcagcagcgtggtg accgtgccctccagcaacttcggcacccagacctacacctgcaacgt agatcacaagcccagcaacaccaaggtggacaagacagttgagcgca aatgttgtgtcgagtgcccaccgtgcccagcaccacctgtggcagga ccgtcagtcttcctcttccccccaaaacccaaggacaccctcatgat ctcccggacccctgaggtcacgtgcgtggtggtggacgtgagccacg aagaccccgaggtccagttcaactggtacgtggacggcgtggaggtg cataatgccaagacaaagccacgggaggagcagttcaacagcacgtt ccgtgtggtcagcgtcctcaccgttgtgcaccaggactggctgaacg gcaaggagtacaagtgcaaggtctccaacaaaggcctcccagccccc atcgagaaaaccatctccaaaaccaaagggcagccccgagaaccaca ggtgtacaccctgcccccatcccgggaggagatgaccaagaaccagg tcagcctgacctgcctggtcaaaggcttctaccccagcgacatcgcc |

TABLE 8-continued

| Description | SEQ ID NO | Sequence |
|---|---|---|
| | | gtggagtgggagagcaatgggcagccggagaacaactacaagaccac<br>acctcccatgctggactccgacggctccttcttcctctacagcaagc<br>tcaccgtggacaagagcaggtggcagcaggggaacgtcttctcatgc<br>tccgtgatgcatgaggctctgcacaaccactacacgcagaagagcct<br>ctccctgtctccgggtaaa |
| Ab1-<br>Heavy Chain<br>protein | 6 | QVQLVQSGAEVKKPGASVKVSCKASGYTFTSYDINWVRQATGQGLEW<br>MGWMNPNSGNTDYAQKFQGRVTMTRNISISTAYIELSSLRSEDTAVY<br>YCARDMVAANTDYYFYYGMDVWGQGTTVTVSSASTKGPSVFPLAPCs<br>RSTSESTAALGCLVKDYFPEPVTVSWNSGALTSGVHTFPAVLQSSGL<br>YSLSSVVTVPSSNFGTQTYTCNVDHKPSNTKVDKTVERKCCVECPPC<br>PAPPVAGPSVFLFPPKPKDTLMISRTPEVTCVVVDVSHEDPEVQFNW<br>YVDGVEVHNAKTKPREEQFNSTFRVVSVLTVVHQDWLNGKEYKCKVS<br>NKGLPAPIEKTISKTKGQPREPQVYTLPPSREEMTKNQVSLTCLVKG<br>FYPSDIAVEWESNGQPENNYKTTPPMLDSDGSFFLYSKLTVDKSRWQ<br>QGNVFSCSVMHEALHNHYTQKSLSLSPGK |
| Ab2*<br>Heavy Chain<br>protein | 7 | QVQLVQSGAEVKKPGASVKVSCKASGYTFTSYEINWVRQATGQGLEW<br>MGWMNPNSGYTGYAQKFQGRVTMTRNTSISTAYMEMSSLRSEDTAVY<br>YCARDIVAANTDYYFYYGMDVWGQGTTVTVSSASTKGPSVFPLAPCS<br>RSTSESTAALGCLVKDYFPEPVTVSWNSGALTSGVHTFPAVLQSSGL<br>YSLSSVVTVPSSNFGTQTYTCNVDHKPSNTKVDKTVERKCCVECPPC<br>PAPPVAGPSVFLFPPKPKDTLMISRTPEVTCVVVDVSHEDPEVQFNW<br>YVDGVEVHNAKTKPREEQFNSTFRVVSVLTVVHQDWLNGKEYKCKVS<br>NKGLPAPIEKTISKTKGQPREPQVYTLPPSREEMTKNQVSLTCLVKG<br>FYPSDIAVEWESNGQPENNYKTTPPMLDSDGSFFLYSKLTVDKSRWQ<br>QGNVFSCSVMHEALHNHYTQKSLSLSPGK |
| Ab3-<br>Heavy Chain<br>protein | 8 | QVHLVQSGAEVKKPGASVKVSCKASGYTFTSYGISWVRQAPGQGLEW<br>MGWLSTYSGNTNYAQKLQGRVTMTTDTSTSTAYMELRSLRSDDTAVY<br>YCARGNFYYYGMDVWGQGTTVTVSSASTKGPSVFPLAPCSRSTSEST<br>AALGCLVKDYFPEPVTVSWNSGALTSGVHTFPAVLQSSGLYSLSSVV<br>TVPSSNFGTQTYTCNVDHKPSNTKVDKTVERKCCVECPPCPAPPVAG<br>PSVFLFPPKPKDTLMISRTPEVTCVVVDVSHEDPEVQFNWYVDGVEV<br>HNAKTKPREEQFNSTFRVVSVLTVVHQDWLNGKEYKCKVSNKGLPAP<br>IEKTISKTKGQPREPQVYTLPPSREEMTKNQVSLTCLVKGFYPSDIA<br>VEWESNGQPENNYKTTPPMLDSDGSFFLYSKLTVDKSRWQQGNVFSC<br>SVMHEALHNHYTQKSLSLSPGK |
| Ab1-<br>Heavy Chain<br>Variable<br>Region | 9 | QVQLVQSGAEVKKPGASVKVSCKASGYTFTSYDINWVRQATGQGLEW<br>MGWMNPNSGNTDYAQKFQGRVTMTRNISISTAYIELSSLRSEDTAVY<br>YCARDMVAANTDYYFYYGMDVWGQGTTVTVSS |
| Ab2-<br>Heavy Chain<br>Variable<br>Region | 10 | QVQLVQSGAEVKKPGASVKVSCKASGYTFTSYEINWVRQATGQGLEW<br>MGWMNPNSGYTGYAQKFQGRVTMTRNTSISTAYMEMSSLRSEDTAVY<br>YCARDIVAANTDYYFYYGMDVWGQGTTVTVSS |
| Ab3-<br>Heavy Chain<br>Variable Region | 11 | QVHLVQSGAEVKKPGASVKVSCKASGYTFTSYGISWVRQAPGQGLEW<br>MGWLSTYSGNTNYAQKLQGRVTMTTDTSTSTAYMELRSLRSDDTAVY<br>YCARGNFYYYGMDVWGQGTTVTVSS |
| Ab1-<br>Heavy Chain CDR1 | 12 | SYDIN |
| Ab2-<br>Heavy Chain CDR1 | 13 | SYEIN |
| Ab3-<br>Heavy Chain CDR1 | 14 | SYGIS |
| Ab1-<br>Heavy Chain CDR2 | 15 | WMNPNSGNTDYAQKFQG |
| Ab2-<br>Heavy Chain CDR2 | 16 | WMGWMNPNSGYTGYAQKFQG |
| Ab3-<br>Heavy Chain CDR2 | 17 | WLSTYSGNTNYAQKLQG |
| Ab1-<br>Heavy Chain CDR3 | 18 | DMVAANTDYYFYYGMDV |
| Ab2-<br>Heavy Chain CDR3 | 19 | DIVAANTDYYFYYGMDV |

TABLE 8-continued

| Description | SEQ ID NO | Sequence |
|---|---|---|
| Ab3- Heavy Chain CDR3 | 20 | GNFYYYGMDV |
| Ab1- Light Chain nucleotide | 21 | cagtctgtgctgactcagccaccctcagcatctgggaccccgggca gagggtcaccatctcttgttctggaagcagctccaacgtcggaagta atactgtaagctggtaccaacagctcccaggaacggcccccaaactc ctcatctatactaataatcggcggcctccggggtccctgaccgatt ctctggctccaagtctggcacctcagcctcctggccatcagtgggc tccagtctgaggatgaggctgattatttctgtgcagcgttagatgac agtctgaatggtgtggtattcggcggagggaccaaactgaccgtcct aggccaaccgaaagcggcgccctcggtcactctgttcccgccctcct ctgaggagcttcaagccaacaaggccacactggtgtgtctcataagt gacttctacccgggagccgtgacagtggcctggaaggcagatagcag ccccgtcaaggcgggagtggagaccaccacacctccaaacaaagca acaacaagtacgcggccagcagctatctgagcctgacgcctgagcag tggaagtcccacagaagctacagctgccaggtcacgcatgaagggag caccgtggagaagacagtggcccctacagaatgttca |
| Ab2- Light Chain nucleotide | 22 | cagtctgtgctgactcagccaccctcagcgtctgggaccccgggca gagggtcaccatctcttgttctggaagcaactccaacatcggaagta atactgtcaactggtaccaccagctcccaggaacggcccccaaactc ctcatctataatattaataagcggccctcaggggtccctgaccgatt ctctggctccaagtctggcctccagcctcctggccatcagtgggc tccagtctgaggatgaggctgattattactgttcaacatgggatgac agcctggatggtgtggtattcggcggagggaccaagctgaccgtcct aggccaaccgaaagcggcgccctcggtcactctgttcccgccctcct ctgaggagcttcaagccaacaaggccacactggtgtgtctcataagt gacttctacccgggagccgtgacagtggcctggaaggcagatagcag ccccgtcaaggcgggagtggagaccaccacacctccaaacaaagca acaacaagtacgcggccagcagctatctgagcctgacgcctgagcag tggaagtcccacagaagctacagctgccaggtcacgcatgaagggag caccgtggagaagacagtggcccctacagaatgttca |
| Ab3- Light Chain nucleotide | 23 | gaaattgtgttgacgcagtctccaggcaccctgtctttgtctccagg ggaaagagccaccctctcctgcagggccagtcagagtgttagcagca gctacttagcctggtaccagcagaaacctggccaggctcccaggctc ctcatctttggtgcttccagcagggccactggcatcccagacaggtt cagtggcagtgggtctgggacagacttcactctcaccatcagcagac tggagcctgaagattttgcagtgtattactgtcagcagtatggtagc tcgcctccgatcaccttcggccaagggacacgactggagattaaacg tacggtggctgcaccatctgtcttcatcttcccgccatctgatgagc agttgaaatctggaactgcctctgttgtgtgcctgctgaataacttc tatcccagagaggccaaagtacagtggaaggtggataacgccctcca atcgggtaactcccaggagagtgtcacagagcaggacagcaaggaca gcacctacagcctcagcagcaccctgacgctgagcaaagcagactac gagaaacacaaagtctacgcctgcgaagtcacccatcagggcctgag ctcgcccgtcacaaagagcttcaacaggggagagtgt |
| Ab1- Light Chain protein | 24 | QSVLTQPPSASGTPGQRVTISCSGSSSNVGSNTVSWYQQLPGTAPKL LIYTNNRRPSGVPDRFSGSKSGTSASLAISGLQSEDEADYFCAALDD SLNGVVFGGGTKLTVLGQPKAAPSVTLFPPSSEELQANKATLVCLIS DFYPGAVTVAWKADSSPVKAGVETTTPSKQSNNKYAASSYLSLTPEQ WKSHRSYSCQVTHEGSTVEKTVAPTECS |
| Ab2- Light Chain protein | 25 | QSVLTQPPSASGTPGQRVTISCSGSNSNIGSNTVNWYHQLPGTAPKL LIYNINKRPSGVPDRFSGSKSGSSASLAISGLQSEDEADYYCSTWDD SLDGVVFGGGTKLTVLGQPKAAPSVTLFPPSSEELQANKATLVCLIS DFYPGAVTVAWKADSSPVKAGVETTTPSKQSNNKYAASSYLSLTPEQ WKSHRSYSCQVTHEGSTVEKTVAPTECS |
| Ab3- Light Chain protein | 26 | EIVLTQSPGTLSLSPGERATLSCRASQSVSSSYLAWYQQKPGQAPRL LIFGASSRATGIPDRFSGSGSGTDFTLTISRLEPEDFAVYYCQQYGS SPPITFGQGTRLEIKRTVAAPSVFIFPPSDEQLKSGTASVVCLLNNF YPREAKVQWKVDNALQSGNSQESVTEQDSKDSTYSLSSTLTLSKADY EKHKVYACEVTHQGLSSPVTKSFNRGEC |
| Ab1- Light Chain Variable | 27 | QSVLTQPPSASGTPGQRVTISCSGSSSNVGSNTVSWYQQLPGTAPKL LIYTNNRRPSGVPDRFSGSKSGTSASLAISGLQSEDEADYFCAALDD SLNGVVFGGGTKLTVLG |
| Ab2- Light Chain Variable | 28 | QSVLTQPPSASGTPGQRVTISCSGSNSNIGSNTVNWYHQLPGTAPKL LIYNINKRPSGVPDRFSGSKSGSSASLAISGLQSEDEADYYCSTWDD SLDGVVFGGGTKLTVLG |
| Ab3- | 29 | EIVLTQSPGTLSLSPGERATLSCRASQSVSSSYLAWYQQKPGQAPRL |

TABLE 8-continued

| Description | SEQ ID NO | Sequence |
|---|---|---|
| Light Chain Variable | | LIFGASSRATGIPDRFSGSGSGTDFTLTISRLEPEDFAVYYCQQYGS SPPITFGQGTRLEIKR |
| Ab1-Light Chain CDR1 | 30 | SGSSSNVGSNTVS |
| Ab2-Light Chain CDR1 | 31 | SGSNSNIGSNTVN |
| Ab3-Light Chain CDR1 | 32 | RASQSVSSSYLA |
| Ab1-Light Chain CDR2 | 33 | TNNRRPS |
| Ab2-Light Chain CDR2 | 34 | NINKRPS |
| Ab3-Light Chain CDR2 | 35 | GASSRAT |
| Ab1-Light Chain CDR3 | 36 | AALDDSLNGVV |
| Ab2-Light Chain CDR3 | 37 | STWDDSLDGVV |
| Ab-Light Chain CDR3 | 38 | QQYGSSPPIT |

Example 7: Modified Anti-OSMR Antibodies

Modified versions of Ab1, Ab2, and Ab3 were generated. For all three modified forms of the antibodies, the lysine at the C terminus of the heavy chain was removed. For Ab1 and Ab2, the glycosylation site at position 73 was removed by substituting the asparagine at position 73 with an aspartic acid. These variants are referred to as Ab1-N73D and Ab2-N73D. The sequences of the modified antibodies are set forth in Table 9 below (the modified nucleotides and amino acids are underlined).

TABLE 9

| Description | SEQ ID NO | Sequence |
|---|---|---|
| Ab1 version 2-Heavy Chain nucleotide (N73D IC-terminal lysine deleted) | 47 | caggtgcagctggtgcagtctggggctgaggtgaagaagcctggggc ctcagtgaaggtctcctgcaaggcttctggatacaccttcaccagtt atgatatcaactgggtgcgacaggcccactggacaggggcttgagtgg atgggatggatgaaccctaatagtggtaacacagactatgcacagaa gttccagggcagagtcaccatgaccagggacatttccataagcacgg cctacattgagctgagcagcctgagatctgaggacacggccgtttat tactgtgcgagagatatggtggctgcgaatacggattactacttcta ctacggtatggacgtctggggccaagggaccacggtcaccgtctcct cagctagcaccaagggcccatcggtcttcccccctggcgccctgctcc aggagcacctccgagagcacagcggccctgggctgcctggtcaagga ctacttccccgaaccggtgacggtgtcgtggaactcaggcgctctga ccagcggcgtgcacaccttcccagctgtcctacagtcctcaggactc tactccctcagcagcgtggtgaccgtgccctccagcaacttcggcac ccagacctacacctgcaacgtagatcacaagcccagcaacaccaagg tggacaagacagttgagcgcaaatgttgtgtcgagtgcccaccgtgc ccagcaccacctgtggcaggaccgtcagtcttcctcttcccccaaa acccaaggacaccctcatgatctcccggacccctgaggtcacgtgcg tggtggtggacgtgagccacgaagacccgaggtccagttcaactgg tacgtggacggcgtggaggtgcataatgccaagacaaagccacggga ggagcagttcaacagcacgttccgtgtggtcagcgtcctcaccgttg tgcaccaggactggctgaacggcaaggagtacaagtgcaaggtctcc aacaaaggcctcccagcccccatcgagaaaaccatctccaaaaccaa agggcagccccgagaaccacaggtgtacaccctgcccccatcccggg aggagatgaccaagaaccaggtcagcctgacctgcctggtcaaaggc ttctaccccagcgacatcgccgtggagtgggagagcaatgggcagcc ggagaacaactacaagaccacacctcccatgctggactccgacggct ccttcttcctctacagcaagctcaccgtggacaagagcaggtggcag caggggaacgtcttctcatgctccgtgatgcatgaggctctgcacaa ccactacacgcagaagagcctctccctgtctccgggt |

TABLE 9-continued

| Description | SEQ ID NO | Sequence |
|---|---|---|
| Ab2 version 2-<br>Heavy Chain<br>nucleotide<br>(N73D IC-terminal<br>lysine deleted) | 48 | caggtgcagctggtgcagtctggggctgaggtgaagaagcctggggc<br>ctcagtgaaggtctcctgcaaggcttctggatacacccttcaccagtt<br>atgaaatcaactgggtgcgacaggccactggacaagggcttgagtgg<br>atgggatggatgaaccctaacagtggttacacaggctatgcacagaa<br>gttccagggcagagtcaccatgaccagggacacctccataagcacag<br>cctacatggaaatgagcagcctgagatctgaggacacggccgtgtat<br>tactgtgcgagagatatagtggctgcgaatacggattactacttcta<br>ttatggtatggacgtctggggccaagggaccacggtcaccgtctcct<br>cagctagcaccaagggcccatcggtcttccccctggcgccctgctcc<br>aggagcacctccgagagcacagcggccctgggctgcctggtcaagga<br>ctacttccccgaaccggtgacggtgtcgtggaactcaggcgctctga<br>ccagcggcgtgcacaccttcccagctgtcctacagtcctcaggactc<br>tactccctcagcagcgtggtgaccgtgccctccagcaacttcggcac<br>ccagacctacacctgcaacgtagatcacaagcccagcaacaccaagg<br>tggacaagacagttgagcgcaaatgttgtgtcgagtgcccaccgtgc<br>ccagcaccacctgtggcaggaccgtcagtcttcctcttcccccccaaa<br>acccaaggacaccctcatgatctcccggacccctgaggtcacgtgcg<br>tggtggtggacgtgagccacgaagaccccgaggtccagttcaactgg<br>tacgtggacggcgtggaggtgcataatgccaagacaaagccacggga<br>ggagcagttcaacagcacgttccgtgtggtcagcgtcctcaccgttg<br>tgcaccaggactggctgaacggcaaggagtacaagtgcaaggtctcc<br>aacaaaggcctcccagcccccatcgagaaaaccatctccaaaaccaa<br>agggcagccccgagaaccacaggtgtacaccctgcccccatcccggg<br>aggagatgaccaagaaccaggtcagcctgacctgcctggtcaaaggc<br>ttctaccccagcgacatcgccgtggagtgggagagcaatgggcagcc<br>ggagaacaactacaagaccacacctcccatgctggactccgacggct<br>ccttcttcctctacagcaagctcaccgtggacaagagcaggtggcag<br>caggggaacgtcttctcatgctccgtgatgcatgaggctctgcacaa<br>ccactacacgcagaagagcctctccctgtctccgggt |
| Ab3-<br>Heavy Chain<br>nucleotide<br>(C-terminal lysine<br>deleted) | 49 | caggttcatctggtgcagtctggagctgaggtgaagaagcctggggc<br>ctcagtgaaggtctcctgcaaggcttctggttacacctttaccagct<br>atggtatcagctgggtgcgacaggcccctggacaagggcttgagtgg<br>atgggatggctcagcacttacagtggtaacacaaactatgcacagaa<br>gctccagggcagagtcaccatgaccacagacacatccacgagcacag<br>cctacatggagctgaggagcctgagatctgacgacacggccgtgtat<br>tactgtgcgagagggaacttctactactacggtatggacgtctgggg<br>ccaggggaccacggtcaccgtctcctcagctagcaccaagggcccat<br>cggtcttccccctggcgccctgctccaggagcacctccgagagcaca<br>gcggccctgggctgcctggtcaaggactacttccccgaaccggtgac<br>ggtgtcgtggaactcaggcgctctgaccagcggcgtgcacaccttcc<br>cagctgtcctacagtcctcaggactctactccctcagcagcgtggtg<br>accgtgccctccagcaacttcggcacccagacctacacctgcaacgt<br>agatcacaagcccagcaacaccaaggtggacaagacagttgagcgca<br>aatgttgtgtcgagtgcccaccgtgcccagcaccacctgtggcagga<br>ccgtcagtcttcctcttccccccaaaacccaaggacaccctcatgat<br>ctcccggacccctgaggtcacgtgcgtggtggtggacgtgagccacg<br>aagaccccgaggtccagttcaactggtacgtggacggcgtggaggtg<br>cataatgccaagacaaagccacgggaggagcagttcaacagcacgtt<br>ccgtgtggtcagcgtcctcaccgttgtgcaccaggactggctgaacg<br>gcaaggagtacaagtgcaaggtctccaacaaaggcctcccagccccc<br>atcgagaaaaccatctccaaaaccaaagggcagccccgagaaccaca<br>ggtgtacaccctgcccccatcccgggaggagatgaccaagaaccagg<br>tcagcctgacctgcctggtcaaaggcttctaccccagcgacatcgcc<br>gtggagtgggagagcaatgggcagccggagaacaactacaagaccac<br>acctcccatgctggactccgacggctccttcttcctctacagcaagc<br>tcaccgtggacaagagcaggtggcagcaggggaacgtcttctcatgc<br>tccgtgatgcatgaggctctgcacaaccactacacgcagaagagcct<br>ctccctgtctccgggt |
| Ab1 version 2-<br>Heavy Chain protein<br>(N73D/C-terminal<br>lysine deleted) | 50 | QVQLVQSGAEVKKPGASVKVSCKASGYTFTSYDINWVRQATGQGLEW<br>MGWMNPNSGNTDYAQKFQGRVTMTRDISISTAYIELSSLRSEDTAVY<br>YCARDMVAANTDYYFYYGMDVWGQGTTVTVSSASTKGPSVFPLAPCS<br>RSTSESTAALGCLVKDYFPEPVTVSWNSGALTSGVHTFPAVLQSSGL<br>YSLSSVVTVPSSNFGTQTYTCNVDHKPSNTKVDKTVERKCCVECPPC<br>PAPPVAGPSVFLFPPKPKDTLMISRTPEVTCVVVDVSHEDPEVQFNW<br>YVDGVEVHNAKTKPREEQFNSTFRVVSVLTVVHQDWLNGKEYKCKVS<br>NKGLPAPIEKTISKTKGQPREPQVYTLPPSREEMTKNQVSLTCLVKG<br>FYPSDIAVEWESNGQPENNYKTTPPMLDSDGSFFLYSKLTVDKSRWQ<br>QGNVFSCSVMHEALHNHYTQKSLSLSPG |
| Ab2 version 2-<br>Heavy Chain protein<br>(N73D IC-terminal<br>lysine deleted) | 51 | QVQLVQSGAEVKKPGASVKVSCKASGYTFTSYEINWVRQATGQGLEW<br>MGWMNPNSGYTGYAQKFQGRVTMTRDTSISTAYMEMSSLRSEDTAVY<br>YCARDIVAANTDYYFYYGMDVWGQGTTVTVSSASTKGPSVFPLAPCS<br>RSTSESTAALGCLVKDYFPEPVTVSWNSGALTSGVHTFPAVLQSSGL |

TABLE 9-continued

| Description | SEQ ID NO | Sequence |
|---|---|---|
| | | YSLSSVVTVPSSNFGTQTYTCNVDHKPSNTKVDKTVERKCCVECPPC PAPPVAGPSVFLFPPKPKDTLMISRTPEVTCVVVDVSHEDPEVQFNW YVDGVEVHNAKTKPREEQFNSTFRVVSVLTVVHQDWLNGKEYKCKVS NKGLPAPIEKTISKTKGQPREPQVYTLPPSREEMTKNQVSLTCLVKG FYPSDIAVEWESNGQPENNYKTTPPMLDSDGSFFLYSKLTVDKSRWQ QGNVFSCSVMHEALHNHYTQKSLSLSPG |
| Ab3 version 2-Heavy Chain protein (C-terminal lysine deleted) | 52 | QVHLVQSGAEVKKPGASVKVSCKASGYTFTSYGISWVRQAPGQGLEW MGWLSTYSGNTNYAQKLQGRVTMTTDTSTSTAYMELRSLRSDDTAVY YCARGNFYYYGMDVWGQGTTVTVSSASTKGPSVFPLAPCSRSTSEST AALGCLVKDYFPEPVTVSWNSGALTSGVHTFPAVLQSSGLYSLSSVV TVPSSNFGTQTYTCNVDHKPSNTKVDKTVERKCCVECPPCPAPPVAG PSVFLFPPKPKDTLMISRTPEVTCVVVDVSHEDPEVQFNWYVDGVEV HNAKTKPREEQFNSTFRVVSVLTVVHQDWLNGKEYKCKVSNKGLPAP IEKTISKTKGQPREPQVYTLPPSREEMTKNQVSLTCLVKGFYPSDIA VEWESNGQPENNYKTTPPMLDSDGSFFLYSKLTVDKSRWQQGNVFSC SVMHEALHNHYTQKSLSLSPG |
| Ab1 version-Heavy Chain Variable Region (N73D/C-terminal lysine deleted) | 53 | QVQLVQSGAEVKKPGASVKVSCKASGYTFTSYDINWVRQATGQGLEW MGWMNPNSGNTDYAQKFQGRVTMTRDISISTAYIELSSLRSEDTAVY YCARDMVAANTDYYFYYGMDVWGQGTTVTVSS |
| Ab2 version 2-Heavy Chain Variable Region (N73D/C-terminal lysine deleted) | 54 | QVQLVQSGAEVKKPGASVKVSCKASGYTFTSYEINWVRQATGQGLEW MGWMNPNSGYTGYAQKFQGRVTMTRDTSISTAYMEMSSLRSEDTAVY YCARDIVAANTDYYFYYGMDVWGQGTTVTVSS |

ELISA experiments were performed under various formats (Capture ELISA for avidity-less format; Sandwich ELISA for solution phase format; and Direct ELISA for solid state avidity format) using antibodies containing the variable regions of Ab1 or Ab2 (or the N73D variant of Ab1 or Ab2) with different Fc regions.

Ab1 and Ab2 each contain CH1, CH2, CH3 domains of human IgG2 origin. As used herein, the terms "Ab1" and "Ab1 IgG2 WT" refer to the same antibody. Similarly, the terms "Ab2" and "Ab2 IgG2 WT" refer to the same antibody.

Antibodies identified as "IgG4P agly/IgG1" contain the variable regions of Ab1 or Ab2 (or the N73D variant of Ab1 or Ab2) fused to the CH1 domain from human IgG4, the hinge from human IgG4 with a Ser to Pro mutation (at position 228) to reduce shuffling, the CH2 domain from human IgG4 with an Asn to Gln mutation (at position 297) to eliminate the N-linked glycosylation site, and the CH3 domain from human IgG. The "IgG4P agly/IgG1" framework is described in US published patent application number US 2012/0100140.

The ELISA results indicated that removal of glycosylation sites via the N73D substitution did not affect the binding of the modified antibodies to OSMR. See Table 10.

TABLE 10

| Antibody | Capture (EC50) nM | Sandwich (EC50) nM | Direct (EC50) nM |
|---|---|---|---|
| Ab1 IgG2 WT | 10.2 | 0.581 | 0.184 |
| Ab1 N73D IgG2 | 4.85 | 0.359 | 0.0728 |
| Ab1 N73D IgG4P agly/IgG1 | 2.86 | 0.05 | 0.0626 |
| Ab2 IgG2 WT | 3.63 | 0.366 | 0.182 |
| Ab2 N73D IgG2 | 5.49 | 0.343 | 0.179 |

TABLE 10-continued

| Antibody | Capture (EC50) nM | Sandwich (EC50) nM | Direct (EC50) nM |
|---|---|---|---|
| Ab2 N73D IgG4P agly/IgG1 | 1.61 | 0.064 | 0.0558 |

Binding studies were performed using the BIAcore method. Antibodies containing the variable regions of Ab1 or Ab2 (or the N73D variant of Ab1 or Ab2) with different Fc regions were immobilized on a CM4 chip (GE lifesciences) as per manufacturer's protocols. Soluble OSMR was used as the analyte. Removing the glycosylation site on Ab1 and Ab2 via the N73D substitution improved the binding affinities. For Ab1, the substitution improved Kon rate, whereas for Ab2 it improved Koff rate. See Table 11.

TABLE 11

| Antibody | Kon (M−1s−1) | Koff (1/s) | KD (M) |
|---|---|---|---|
| Ab1 IgG2 WT | 1.64E+05 | 1.50E−04 | 0.913E−9 |
| Ab1 N73D IgG2 | 2.49E+05 | 1.68E−04 | 0.675E−9 |
| Ab2 IgG2 WT | 1.88E+05 | 1.89E−04 | 1.01E−09 |
| Ab2 N73D IgG2 | 1.73E+05 | 4.99E−05 | 0.289E−9 |

The stability of Fab fragments was determined by assessing the thermal unfolding of antibodies. High melting temperature of Fab fragments correlates directly to increased stability. Removal of glycosylation sites on Ab2 via the N73D substitution did not affect the thermal stability of Fab fragments and showed minor effects on Ab1, as assessed by differential scanning fluorimery experiments. See Table 12.

TABLE 12

| Antibody | Fab Tm (Celsius) | Standard Error (Celsius) |
|---|---|---|
| Ab1 IgG2 WT | 73.24 | 0.0097 |
| Ab1 N73D IgG2 | 71.21 | 0.005 |
| Ab1 N73D IgG4P agly/IgG1 | 74.23 | 0.014 |
| Ab2 IgG2 WT | 76.71 | 0.0096 |
| Ab2 N73D IgG2 | 76.54 | 0.14 |
| Ab2 N73D IgG4P agly/IgG1 | 76.69 | 0.018 |

The ability of modified anti-OSMR antibodies to block signaling through human OSMR was assessed. The modified antibodies were evaluated for their ability to inhibit proliferation of a BaF_hu-IL31R/OSMR/gp130 cell line in the presence of IL31, OSM, or IL31 and OSM. The results are presented in Tables 13 and 14 below, with the IC50 for each antibody shown. The results confirm that the modified versions of Ab1 and Ab2 are potent inhibitors of OSM- and IL-31-mediated signaling.

TABLE 13

| Antibody | IL31 (IC50) | OSM (IC50) | IL31/OSM (IC50) |
|---|---|---|---|
| Ab2 | 0.3828 | 0.3528 | ~1.9 |
| Ab1 IgG2 WT | 0.6691 | 0.5298 | 4.004 |
| Ab1 N73D IgG2 | 0.7565 | 0.5226 | 3.702 |
| Ab1 N73D IgG4P agly/IgG1 | 0.4672 | 0.5657 | 3.080 |

TABLE 14

| Antibody | IL31 (IC50) | OSM (IC50) | IL31/OSM (IC50) |
|---|---|---|---|
| Ab2 | 0.4426 | 0.4019 | 1.8 |
| Ab2 IgG2 WT | 0.3671 | 0.4758 | 2.049 |
| Ab2 N73D IgG2 | 0.2191 | 0.1859 | 1.474 |
| Ab2 N73D IgG4P agly/IgG1 | 0.2838 | 0.2401 | 1.276 |

The disclosure has been described in terms of particular embodiments found or proposed to comprise specific modes for the practice of the disclosure. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed:

1. A method of treating pruritus, said method comprising systemically injecting a therapeutically effective amount of an anti-oncostatin M receptor (OSMR) monoclonal antibody to a human patient in need thereof,
   wherein systemically injecting the anti-OSMR monoclonal antibody results in a decrease in severity of pruritus, and
   wherein the anti-OSMR monoclonal antibody competes with an anti-OSMR antibody defined by a light chain variable domain of SEQ ID NO:28 and a heavy chain variable domain of SEQ ID NO:54.

2. The method of claim 1, wherein the anti-OSMR monoclonal antibody inhibits both OSM and IL-31 signaling.

3. The method of claim 1, wherein the anti-OSMR monoclonal antibody is injected intravenously.

4. The method of claim 1, wherein the anti-OSMR monoclonal antibody is injected subcutaneously.

5. The method of claim 1, wherein the therapeutically effective amount ranges from 0.1 µg/kg to 30 mg/kg.

6. The method of claim 1, wherein the therapeutically effective amount ranges from 1 µg/kg to 20 mg/kg.

7. The method of claim 1, wherein the therapeutically effective amount ranges from 10 µg/kg to 10 mg/kg.

8. The method of claim 1, wherein the anti-OSMR monoclonal antibody is a humanized antibody.

9. The method of claim 1, wherein the anti-OSMR monoclonal antibody is a human antibody.

10. The method of claim 1, wherein the anti-OSMR monoclonal antibody is a chimeric antibody.

11. The method of claim 1, wherein the anti-OSMR monoclonal antibody is an IgG1, IgG2, IgG4, or a hybrid antibody thereof.

12. The method of claim 1, wherein the anti-OSMR monoclonal antibody is aglycosylated.

* * * * *